US007659058B2

United States Patent
Deml

(10) Patent No.: US 7,659,058 B2
(45) Date of Patent: Feb. 9, 2010

(54) METHOD FOR IDENTIFYING TARGET EPITOPES OF THE T CELL MEDIATED IMMUNE RESPONSE AND FOR ASSAYING EPITOPE-SPECIFIC T CELLS

(75) Inventor: Ludwig Deml, Regenstauf (DE)

(73) Assignee: Lophius Biosciences GmbH, Regensburg (DE)

( * ) Notice: Subject to any disclaimer, the term of this patent is extended or adjusted under 35 U.S.C. 154(b) by 333 days.

(21) Appl. No.: 10/495,843

(22) PCT Filed: Nov. 20, 2002

(86) PCT No.: PCT/DE02/04270

§ 371 (c)(1),
(2), (4) Date: Dec. 9, 2004

(87) PCT Pub. No.: WO03/046212

PCT Pub. Date: Jun. 5, 2003

(65) Prior Publication Data

US 2005/0112576 A1 May 26, 2005

(30) Foreign Application Priority Data

Nov. 20, 2001 (DE) .................................. 101 56 863

(51) Int. Cl.
*C12Q 1/68* (2006.01)
*G01N 33/53* (2006.01)
*C12N 5/08* (2006.01)

(52) U.S. Cl. ........................... 435/6; 435/7.1; 435/372; 435/456

(58) Field of Classification Search .................. None
See application file for complete search history.

(56) References Cited

FOREIGN PATENT DOCUMENTS

| WO | WO 97/26325 | 7/1997 |
|---|---|---|
| WO | WO 00/57705 | 10/2000 |
| WO | WO 00/67761 | 11/2000 |
| WO | WO 01/32204 | 5/2001 |

OTHER PUBLICATIONS

Linette et al., 2000, J. Immunol. 164:3402-3412.*
den Haan et al., 2000, PNAS 97:12950-12952.*
Bishop and Hostager, "B lymphocyte activation by contact-mediated interactions with T lymphocytes," *Current Opinion in Immunology*, 13:278-285, 2001.
Clarke, "The critical role of CD40/CD40L in the CD4-dependent generation of $CD8^+T$ cell immunity," *Journal of Leukocyte Biology*, 67:607-614, 2000.
Cui et al., "Targeting transgene expression to antigen presenting cells (APC) differentiated in vivo from lentiviral transduced, engrafting human and mouse hematopoietic stem/progenitor cells," *Blood*, 98(11):214a, abstract, 2001.

(Continued)

*Primary Examiner*—Joseph Woitach
*Assistant Examiner*—Kelaginamane Hiriyanna
(74) *Attorney, Agent, or Firm*—Fulbright & Jaworski

(57) ABSTRACT

The present invention relates to a method for the detection of epitope-specific T-cells and target epitopes of reactive T-cells. Furthermore, the present invention relates to vectors comprising a first promoter which is specifically inducible by the epitope-specific contact with a T-cell in antigen-presenting cells, a nucleic acid which is functionally linked to this first promoter and which encodes a marker gene, a second promoter which is constitutive in antigen-presenting cells, and a nucleic acid which is functionally linked to said second promoter. Furthermore, the present invention relates to antigen-presenting cells which are transduced with the vectors according to the invention.

Figure 1:
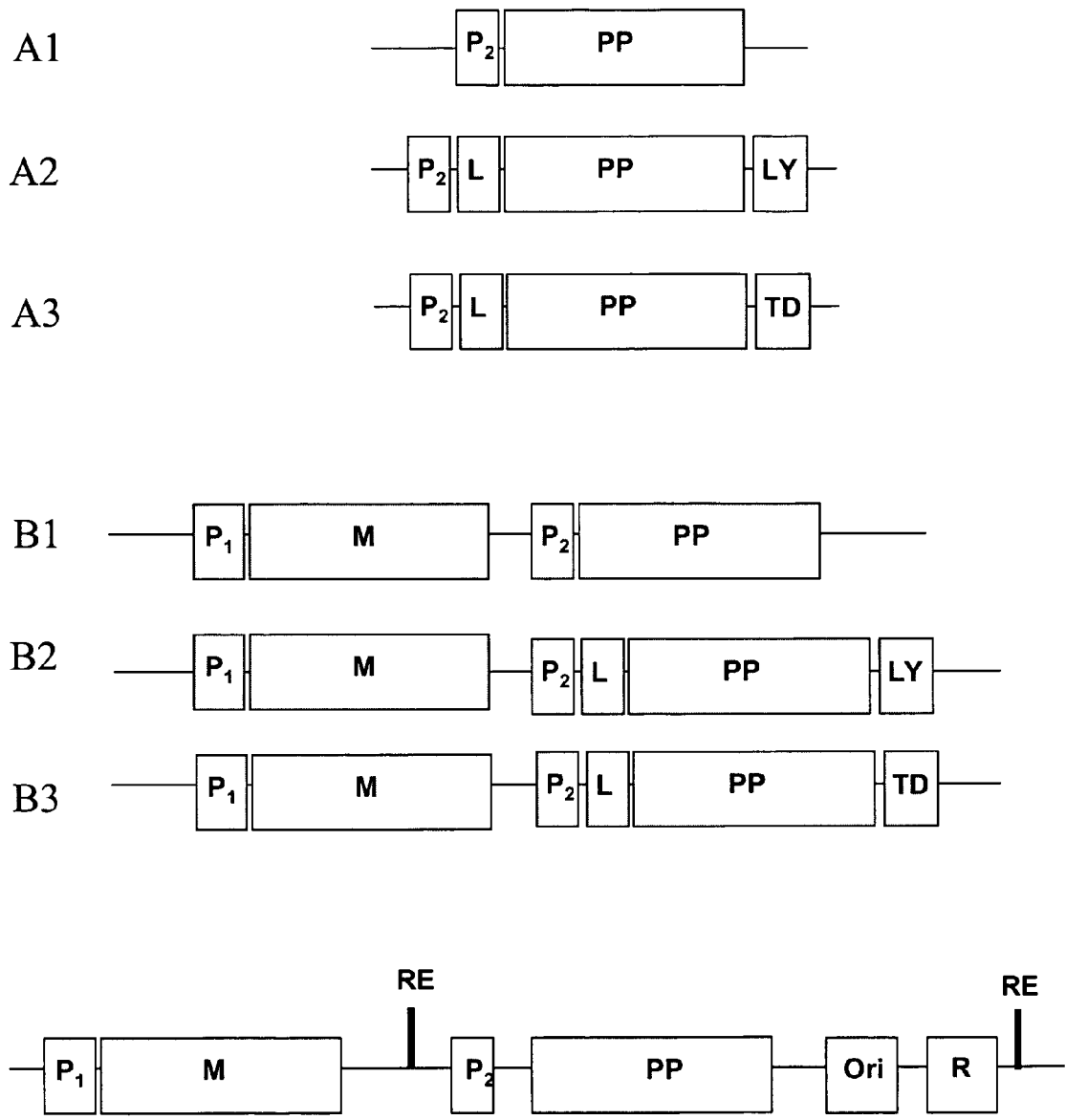

10 Claims, 14 Drawing Sheets accordingly A1-3; B1-3

OTHER PUBLICATIONS den Haan and Bevan, "A novel helper role for CD4 T cells," *Proc. Natl. Acad. Sci., USA*, 97(24):12950-12952, 2000.

Ohshima et al., "Expression and function of OX40 ligand on human dendritic cells," *Journal of Immunology*, 159:3838-3849, 1997.

Takayama et al., "Translation of dendritic cell progenitors with a retroviral vector encoding viral interleukin-10 and enhanced green fluorescent protein allows purification of potentially tolerogenic antigen-presenting cells," *Transplantation*, 68(12):1903-1909, 1999.

Weinberg et al., "OX-40: life beyond the effector T cell stage," *Immunology*, 10:471-480, 1998.

* cited by examiner

| | | | | | |
|---|---|---|---|---|---|
| ggcgggggat | ccggtacctg | gtgtctattg | atagaatacc | cttactttcc | aagttctgag | 60 |
| gccagccaca | acctcaaaga | aagaaataat | cttcaaagct | tatttacatc | tattcatttg | 120 |
| ttcattcatg | gaaaaattat | gtacgggaaa | aatgtgaagt | ggaaggaaag | gagacaagga | 180 |
| taccettctg | cttcttttct | ggtatgcaga | aaattaatca | tataattgtt | tattgaattt | 240 |
| gcctcaaagg | gttaaatgag | agaaagattg | caagtccatc | taacacagtg | tctgacacat | 300 |
| agtaaatgct | tccaaaaggt | agtttatttt | tatgcaatag | actacaacca | aggatctctc | 360 |
| ctttaccttc | tgcatgaccc | agtgtcctat | tttcttgttt | tgtcttttc | attcaagaat | 420 |
| gatctgtgtg | tgctttcttt | ctgaatctgt | gagaggggtt | caatgtttag | ttacatagta | 480 |
| aagtgcagat | aagaaccttg | ggccagcatt | tccctaaat | cttttctatg | atttaagaca | 540 |
| ccttggggaa | gggatatatg | agctgctaca | ttaacggatg | atgatttta | tctttaccaa | 600 |
| gtgacccaca | atttgttact | ggtgcaataa | gttaagaaaa | tagcatactt | ttatgactgt | 660 |
| catttcacag | tcactcaaat | cagaactgga | atgtcacaaa | acaactccc | tgttagccca | 720 |
| gaggaaaaaa | aaaagaaag | aaagtaaagg | ggaaattcag | attagtcaca | aagaagttcc | 780 |
| cccgcctgcc | tgcaaaagtt | gcagcgttaa | aactgagaga | gtccgctttg | ctctttcaat | 840 |
| cgccttttat | ctctggccct | gggacctttg | cctatttct | gattgatagg | ctttgttttg | 900 |
| tcttacctcc | ttctttctgg | gaaaactcag | ttttatcgca | cgttcccctt | ttccatatct | 960 |
| tcatcttccc | tctacccaga | ttgtgaagag | atctcccgcc | | | 1000 |

FIG. 7

```
ccggattggccgcctccagcaggccagagcagatgggaaatgtgtttcctccaactcgctcaac
actgtccctttcttgcaaggggaatttctccacctggactctccgagcttctgcttgtagggtc
ccgaggggctcctgccgggaaccatccagtgggtgggtggggcaggccagggaaggcccaggg
gtcccggggaaggtggccaggagggctgagcatgacactcagggttccactggggggttgggga
tcaggggcagatgctccaggagtgagggtggttgaggcttggctgaagcctgacccttcttag
gaagtgctggatgtggggaacccggggagtcctagtgatggggggctaggggtgctgagag
gaggggaaggagacaaagagagactaaagaaggaaaaggagagagacagggagagacagagagt
cagagagagacagagggaatcagagacagagagaaacagggagagagacagaaagagtgagagc
cagagacatacagagacagggagagacacagagatgcataaagagagggagtcagagatggaga
gagacagagataacggagccagagatagggagagtcagagacagagagaaagaaacacacagac
tgacacagataaaagagccagagacagggagaggcagagacaaagagagatacagagacagaga
taacagagccagagacagagagacagagacagagataacagagccagagacagggagagagtgt
cagagacagagacagacacagagataacagagccagagatagggagagtcagagacagagagaa
agagacacaagacagacatagataaaagagccagagacagggagaggcagagacaaagagagat
acagagacagagatagcagagccagagacagggagagagtgtcagagacagagagacagacaca
gagataacagagccagagatagggagagtcagagacagagagaaagagacagacagacatagat
aaaagagccagagacagggagagagacacagagacagagacatagagacagagataacagagcc
agagacagagtcagagacagagacagagagagccagacacagagacagagagagagtcacag
ccagagacagcgacagagataacagaagcagagagagggagaaagataacagagccagagacag
tcagagacagagatagagagacagagataacagagccagagacagatacagagacagagataac
ggagccagagatagggagagagagtcagagacagagagagatatatagacagagataacagagc
cagacatggggagagagagtcagaggcagagagagagaagacagatagagagacagagccagtg
ataacagagccagagacagggagagagagtcagagagagatacaatgagagacagagataacag
ccagagacagagttagacagagagatacagagacagagataacagagccagagacagggagaga
gaattagagacagagatagagagagacagagacagagataatacaggcacagaggcacgcatag
acataaattggcagagagagagaaagatctctttccacccactgcagaggcaatcaacagagac
agagaaagacgttaacggggagacacagagagcaaaggagactgagtcagcaagagacccacag
agataccgggaaagagcggcagagagggagaaccagggcgatggagagacagcagggagaaagg
aacctggagccgagcttggaaggccggaaacggaaaggagagcgaaaagcggagagagatccga
gtggagaaaattccgcagagtcacggggacgaggggaaaggctctgggctgggaaggggcgtgg
ccgcgggcggaggggcgtggccgcgggcggaggggcgtggcctccttttgtagccaagcagcta
taaaaagcggcgcgctgtgtcttcccgcagtctctcgtc
```

FIG. 8A

```
ggagccagagatagggagagtcagagacagagagaaagaaacacacagactgacacagataaaa
gagccagagacagggagaggcagagacaaagagagatacagagacagagataacagagccagag
acagagagacagagacagagataacagagccagagacagggagagagtgtcagagacagagaca
gacacagagataacagagccagagatagggagagtcagagacagagagaaagagacacaagaca
gacatagataaaagagccagagacagggagaggcagagacaaagagagatacagagacagagat
agcagagccagagacagggagagagtgtcagagacagagagacagacacagagataacagagcc
agagatagggagagtcagagacagagagaaagagacagacagacatagataaaagagccagaga
cagggagagagacacagagacagagacatagagacagagataacagagccagagacagagtcag
agacagagacagagagagccagacacagagacagagagagagtcacagccagagacagcgac
agagataacagaagcagagagagggagaaagataacagagccagagacagtcagagacagagat
agagagacagagataacagagccagagacagatacagagacagagataacggagccagagatag
ggagagagagtcagagacagagagagatatatagacagagataacagagccagacatggggaga
gagagtcagaggcagagagagagaagacagatagagagacagagccagtgataacagagccaga
gacagggagagagagtcagagagagatacaatgagagacagagataacagccagagacagagtt
agacagagagatacagagacagagataacagagccagagacagggagagagaattagagacaga
gatagagagacagagacagagataatacaggcacagaggcacgcatagacataaattggcag
agagagagaaagatctctttccacccactgcagaggcaatcaacagagacagagaaagacgtta
acggggagacacagagagcaaaggagactgagtcagcaagagacccacagagataccgggaaag
agcggcagagagggagaaccagggcgatggagagacagcagggagaaaggaacctggagccgag
cttggaaggccggaaacggaaaggagagcgaaaagcggagagagatccgagtggagaaaattcc
gcagagtcacggggacgaggggaaaggctctgggctgggaaggggcgtggccgcgggcggaggg
gcgtggccgcgggcggaggggcgtggcctccttttgtagccaagcagctataaaaagcggcgcg
ctgtgtcttcccgcagtctctcgtc
```

FIG. 8B

C cagccagagacagcgacagagataacagaagcagagagagggagaaagataacagagccagagacagtcagagacag
agatagagagacagagataacagagccagagacagatacagagacagagataacggagccagagatagggagagaga
gtcagagacagagagagatatatagacagagataacagagccagacatggggagagagagtcagaggcagagagaga
gaagacagatagagagacagagccagtgataacagagccagagacagggagagagagtcagagagagatacaatgag
agacagagataacagccagagacagagttagacagagagatacagagacagagataacagagccagagacagggaga
gagaattagagacagagatagagagagacagagacagagataatacaggcacagaggcacgcatagacataaattgg
cagagagagagaaagatctctttccacccactgcagaggcaatcaacagagacagagaaagacgttaacggggagac
acagagagcaaaggagactgagtcagcaagagacccacagagataccgggaaagagcggcagagagggagaaccagg
gcgatggagagacagcagggagaaaggaacctggagccgagcttggaaggccggaaacggaaaggagagcgaaaagc
ggagagagatccgagtggagaaaattccgcagagtcacggggacgaggggaaaggctctgggctgggaaggggcgtg
gccgcgggcggaggggcgtggccgcgggcggaggggcgtggcctccttttgtagccaagcagctataaaaagcggcg
cgctgtgtcttcccgcagtctctcgtc

D cccactgcagaggcaatcaacagagacagagaaagacgttaacggggagacacagagagcaaaggagactgagtcag
caagagacccacagagataccgggaaagagcggcagagagggagaaccagggcgatggagagacagcagggagaaag
gaacctggagccgagcttggaaggccggaaacggaaaggagagcgaaaagcggagagagatccgagtggagaaaatt
ccgcagagtcacggggacgaggggaaaggctctgggctgggaaggggcgtggccgcgggcggaggggcgtggccgcg
ggcggaggggcgtggcctccttttgtagccaagcagctataaaaagcggcgcgctgtgtcttcccgcagtctctcgt
c

FIG. 8C-D

SEQUENCE LISTING

<160> NUMBER OF SEQ ID NOS: 58

<210> SEQ ID NO 1
<211> LENGTH: 1000
<212> TYPE: DNA

<213> ORGANISM: Homo sapiens

<400> SEQUENCE: 1

```
ggcgggggat ccggtacctg gtgtctattg atagaatacc cttactttcc aagttctgag        60
gccagccaca acctcaaaga agaaataat cttcaaagct tatttacatc tattcatttg       120
ttcattcatg gaaaaattat gtacgggaaa aatgtgaagt ggaaggaaag gagacaagga       180
taccttctg cttcttttct ggtatgcaga aaattaatca tataattgtt tattgaattt       240
gcctcaaagg gttaaatgag agaaagattg caagtccatc taacacagtg tctgacacat       300
agtaaatgct tccaaaaggt agtttatttt tatgcaatag actacaacca aggatctctc       360
ctttaccttc tgcatgaccc agtgtcctat tttcttgttt tgtcttttc attcaagaat       420
gatctgtgtg tgctttcttt ctgaatctgt gagaggggtt caatgtttag ttacatagta       480
aagtgcagat aagaaccttg gccagcatt tcccctaaat cttttctatg atttaagaca       540
ccttgggggaa gggatatatg agctgctaca ttaacggatg atgattttta tctttaccaa       600
gtgacccaca atttgttact ggtgcaataa gttaagaaaa tagcatactt ttatgactgt       660
catttcacag tcactcaaat cagaactgga atgtcacaaa acaactccc tgttagccca       720
gaggaaaaaa aaaagaaag aaagtaaagg ggaaattcag attagtcaca aagaagttcc       780
cccgcctgcc tgcaaaagtt gcagcgttaa aactgagaga gtccgctttg ctctttcaat       840
cgcctttat ctctggccct gggacctttg cctattttct gattgatagg ctttgttttg       900
tcttacctcc ttctttctgg gaaaactcag ttttatcgca cgttccccctt ttccatatct       960
tcatcttccc tctacccaga ttgtgaagag atctcccgcc                           1000
```

<210> SEQ ID NO 2
<211> LENGTH: 2023
<212> TYPE: DNA
<213> ORGANISM: Homo sapiens

<400> SEQUENCE: 2

```
ccggattggc cgcctccagc aggccagagc agatgggaaa tgtgtttcct ccaactcgct        60
caacactgtc cctttcttgc aaggggaatt tctccacctg gactctccga gcttctgctt       120
gtagggtccc gaggggctcc tgccgggaac catccagtgg gtgggtgggg gcaggccagg       180
gaaggcccag gggtcccggg aaggtggcc aggagggctg agcatgacac tcagggttcc       240
actgggggt tggggatcag ggggcagatg ctccaggagt gagggtggtt gaggcttggc       300
tgaagcctga ccttcttag gaagtgctgg atgtggggga acccggggga gtcctagtga       360
tgggggcta gggggtgctg agaggagggg aaggagacaa agagagacta aagaaggaaa       420
aggagagaga cagggagaga cagagagtca gagagagaca gagggaatca gagacagaga       480
gaaacaggga gagagacaga aagagtgaga gccagagaca tacagagaca gggagagaca       540
cagagatgca taaagagagg gagtcagaga tggagagaga cagagataac ggagccagag       600
ataggggagag tcagagacag agagaaagaa acacacagac tgacacagat aaaagagcca       660
gagcagggga gaggcagaga caaagagaga tacagagaca gagataacag agccagagac       720
agagagacag agacagagat aacagagcca gagacaggga gagtgtca gagacagaga       780
cagacacaga gataacagag ccagagatag ggagagtcag agacagagag aaagagacac       840
aagacagaca tagataaaag agccagagac agggagaggc agagacaaag agatatacag       900
agacagagat agcagagcca gagacaggga gagtgtca gagacagaga gacagacaca       960
gagataacag agccagagat agggagagtc agagacagag agaaagagac agacagacat      1020
```

-continued

```
agataaaaga gccagagaca gggagagaga cacagagaca gagacataga gacagagata      1080
acagagccag agacagagtc agagacagag acagagagag ccagacacag agacagagag      1140
agagagtcac agccagagac agcgacagag ataacagaag cagagagagg gagaaagata      1200
acagagccag agacagtcag agacagagat agagagacag agataacaga gccagagaca      1260
gatacagaga cagagataac ggagccagag atagggagag agagtcagag acagagagag      1320
atatatagac agagataaca gagccagaca tggggagaga gagtcagagg cagagagaga      1380
gaagacagat agagagacag agccagtgat aacagagcca gagacaggga gagagagtca      1440
gagagagata caatgagaga cagagataac agccagagac agagttagac agagagatac      1500
agagacagag ataacagagc cagagacagg gagagagaat tagagacaga gatagagaga      1560
gacagagaca gagataatac aggcacagag gcacgcatag acataaattg gcagagagag      1620
agaaagatct ctttccaccc actgcagagg caatcaacag agacagagaa agacgttaac      1680
ggggagacac agagagcaaa ggagactgag tcagcaagag acccacagag ataccgggaa      1740
agagcggcag agagggagaa ccagggcgat ggagagacag cagggagaaa ggaacctgga      1800
gccgagcttg gaaggccgga aacggaaagg agagcgaaaa gcggagagag atccgagtgg      1860
agaaaattcc gcagagtcac ggggacgagg ggaaaggctc tgggctggga aggggcgtgg      1920
ccgcgggcgg aggggcgtgg ccgcgggcgg aggggcgtgg cctccttttg tagccaagca      1980
gctataaaaa gcggcgcgct gtgtcttccc gcagtctctc gtc                       2023
```

<210> SEQ ID NO 3
<211> LENGTH: 1433
<212> TYPE: DNA
<213> ORGANISM: Artificial Sequence
<220> FEATURE:
<223> OTHER INFORMATION: Synthetic Primer

<400> SEQUENCE: 3

```
ggagccagag atagggagag tcagagacag agagaaagaa acacacagac tgacacagat       60
aaaagagcca gagacaggga gaggcagaga caaagagaga tacagagaca gagataacag      120
agccagagac agagagacag agacagagat aacagagcca gagacaggga gagagtgtca      180
gagacagaga cagacacaga gataacagag ccagagatag ggagagtcag agacagagag      240
aaagagacac aagacagaca tagataaaag agccagagac agggagaggc agagacaaag      300
agagatacag agacagagat agcagagcca gagacaggga gagagtgtca gagacagaga      360
gacagacaca gagataacag agccagagat agggagagtc agagacagag agaaagagac      420
agacagacat agataaaaga gccagagaca gggagagaga cacagagaca gagacataga      480
gacagagata acagagccag agacagagtc agagacagag acagagagag ccagacacag      540
agacagagag agagagtcac agccagagac agcgacagag ataacagaag cagagagagg      600
gagaaagata acagagccag agacagtcag agacagagat agagagacag agataacaga      660
gccagagaca gatacagaga cagagataac ggagccagag atagggagag agagtcagag      720
acagagagag atatatagac agagataaca gagccagaca tggggagaga gagtcagagg      780
cagagagaga gaagacagat agagagacag agccagtgat aacagagcca gagacaggga      840
gagagagtca gagagagata caatgagaga cagagataac agccagagac agagttagac      900
agagagatac agagacagag ataacagagc cagagacagg gagagagaat tagagacaga      960
gatagagaga gacagagaca gagataatac aggcacagag gcacgcatag acataaattg     1020
```

| | |
|---|---:|
| gcagagagag agaaagatct ctttccaccc actgcagagg caatcaacag agacagagaa | 1080 |
| agacgttaac ggggagacac agagagcaaa ggagactgag tcagcaagag acccacagag | 1140 |
| ataccgggaa agagcggcag agagggagaa ccagggcgat ggagagacag cagggagaaa | 1200 |
| ggaacctgga gccgagcttg gaaggccgga aacggaaagg agagcgaaaa gcggagagag | 1260 |
| atccgagtgg agaaaattcc gcagagtcac ggggacgagg ggaaaggctc tgggctggga | 1320 |
| aggggcgtgg ccgcgggcgg aggggcgtgg ccgcgggcgg aggggcgtgg cctccttttg | 1380 |
| tagccaagca gctataaaaa gcggcgcgct gtgtcttccc gcagtctctc gtc | 1433 |

<210> SEQ ID NO 4
<211> LENGTH: 874
<212> TYPE: DNA
<213> ORGANISM: Artificial Sequence
<220> FEATURE:
<223> OTHER INFORMATION: Synthetic Primer

<400> SEQUENCE: 4

| | |
|---|---:|
| cagccagaga cagcgacaga gataacagaa gcagagagag ggagaaagat aacagagcca | 60 |
| gagacagtca gagacagaga tagagagaca gagataacag agccagagac agatacagag | 120 |
| acagagataa cggagccaga gatagggaga gagagtcaga gacagagaga gatatataga | 180 |
| cagagataac agagccagac atggggagag agagtcagag gcagagagag agaagacaga | 240 |
| tagagagaca gagccagtga taacagagcc agagacaggg agagagagtc agagagagat | 300 |
| acaatgagag acagagataa cagccagaga cagagttaga cagagagata cagagacaga | 360 |
| gataacagag ccagagacag ggagagagaa ttagagacag agatagagag agacagagac | 420 |
| agagataata caggcacaga ggcacgcata gacataaatt ggcagagaga gagaaagatc | 480 |
| tctttccacc cactgcagag gcaatcaaca gagacagaga aagacgttaa cggggagaca | 540 |
| cagagagcaa aggagactga gtcagcaaga gacccacaga gataccggga aagagcggca | 600 |
| gagagggaga accagggcga tggagagaca gcagggagaa aggaacctgg agccgagctt | 660 |
| ggaaggccgg aaacggaaag gagagcgaaa agcggagaga gatccgagtg gagaaaattc | 720 |
| cgcagagtca cggggacgag gggaaaggct ctgggctggg aaggggcgtg gccgcgggcg | 780 |
| gaggggcgtg gccgcgggcg gaggggcgtg gcctcctttt gtagccaagc agctataaaa | 840 |
| agcggcgcgc tgtgtcttcc cgcagtctct cgtc | 874 |

<210> SEQ ID NO 5
<211> LENGTH: 386
<212> TYPE: DNA
<213> ORGANISM: Artificial Sequence
<220> FEATURE:
<223> OTHER INFORMATION: Synthetic Primer

<400> SEQUENCE: 5

| | |
|---|---:|
| cccactgcag aggcaatcaa cagagacaga gaaagacgtt aacggggaga cacagagagc | 60 |
| aaaggagact gagtcagcaa gagacccaca gagataccgg gaaagagcgg cagagaggga | 120 |
| gaaccagggc gatggagaga cagcagggag aaaggaacct ggagccgagc ttggaaggcc | 180 |
| ggaaacggaa aggagagcga aaagcggaga gatccgagtg gagaaaaat tccgcagagt | 240 |
| cacggggacg aggggaaagg ctctgggctg gaaggggcg tggccgcggg cggaggggcg | 300 |
| tggccgcggg cggaggggcg tggcctcctt ttgtagccaa gcagctataa aaagcggcgc | 360 |
| gctgtgtctt cccgcagtct ctcgtc | 386 |

<210> SEQ ID NO 6
<211> LENGTH: 24
<212> TYPE: DNA
<213> ORGANISM: Artificial Sequence
<220> FEATURE:
<223> OTHER INFORMATION: Synthetic Primer

<400> SEQUENCE: 6
gctggttctt tccgcctcag aagc                                                24

<210> SEQ ID NO 7
<211> LENGTH: 23
<212> TYPE: DNA
<213> ORGANISM: Artificial Sequence
<220> FEATURE:
<223> OTHER INFORMATION: Synthetic Primer

<400> SEQUENCE: 7
cactgcattc tagttgtggt ttg                                                 23

<210> SEQ ID NO 8
<211> LENGTH: 32
<212> TYPE: DNA
<213> ORGANISM: Artificial Sequence
<220> FEATURE:
<223> OTHER INFORMATION: Synthetic Primer

<400> SEQUENCE: 8
gcaggctcgc gactaccggg taggggaggc gc                                       32

<210> SEQ ID NO 9
<211> LENGTH: 35
<212> TYPE: DNA
<213> ORGANISM: Artificial Sequence
<220> FEATURE:
<223> OTHER INFORMATION: Synthetic Primer

<400> SEQUENCE: 9
gcaggcggat ccacgcgctt ctacaaggcg cttgc                                    35

<210> SEQ ID NO 10
<211> LENGTH: 30
<212> TYPE: DNA
<213> ORGANISM: Artificial Sequence
<220> FEATURE:
<223> OTHER INFORMATION: Synthetic Primer

<400> SEQUENCE: 10
gcaggctcgc gacggggttg gggttgcgcc                                          30

<210> SEQ ID NO 11
<211> LENGTH: 33
<212> TYPE: DNA
<213> ORGANISM: Artificial Sequence
<220> FEATURE:
<223> OTHER INFORMATION: Synthetic Primer

<400> SEQUENCE: 11
gcaggcggat cctttggaaa tacagctggg gag                                      33

<210> SEQ ID NO 12
<211> LENGTH: 32
<212> TYPE: DNA
<213> ORGANISM: Artificial Sequence
<220> FEATURE:
<223> OTHER INFORMATION: Synthetic Primer

```
<400> SEQUENCE: 12
gcaggctcgc gacgatggcc ctgcccagtc cc                                32

<210> SEQ ID NO 13
<211> LENGTH: 32
<212> TYPE: DNA
<213> ORGANISM: Artificial Sequence
<220> FEATURE:
<223> OTHER INFORMATION: Synthetic Primer

<400> SEQUENCE: 13
gcaggcggat ccgacagcag cgggaggacc tc                                32

<210> SEQ ID NO 14
<211> LENGTH: 32
<212> TYPE: DNA
<213> ORGANISM: Artificial Sequence
<220> FEATURE:
<223> OTHER INFORMATION: Synthetic Primer

<400> SEQUENCE: 14
gcaggctcgc gaggctccgg tgcccgtcag tg                                32

<210> SEQ ID NO 15
<211> LENGTH: 33
<212> TYPE: DNA
<213> ORGANISM: Artificial Sequence
<220> FEATURE:
<223> OTHER INFORMATION: Synthetic Primer

<400> SEQUENCE: 15
gcaggcggat ccacctagcc agcttgggtc tcc                               33

<210> SEQ ID NO 16
<211> LENGTH: 33
<212> TYPE: DNA
<213> ORGANISM: Artificial Sequence
<220> FEATURE:
<223> OTHER INFORMATION: Synthetic Primer

<400> SEQUENCE: 16
gcaggctcgc gaggcctccg cgccgggttt tgg                               33

<210> SEQ ID NO 17
<211> LENGTH: 35
<212> TYPE: DNA
<213> ORGANISM: Artificial Sequence
<220> FEATURE:
<223> OTHER INFORMATION: Synthetic Primer

<400> SEQUENCE: 17
gcaggcggat ccgtctaaca aaaagccaa aaacg                              35

<210> SEQ ID NO 18
<211> LENGTH: 34
<212> TYPE: DNA
<213> ORGANISM: Artificial Sequence
<220> FEATURE:
<223> OTHER INFORMATION: Synthetic Primer

<400> SEQUENCE: 18
gcaggctcgc gagctgtaat ttctaatcta aacc                              34

<210> SEQ ID NO 19
<211> LENGTH: 33
```

<212> TYPE: DNA
<213> ORGANISM: Artificial Sequence
<220> FEATURE:
<223> OTHER INFORMATION: Synthetic Primer

<400> SEQUENCE: 19
gcaggcggat ccagcagcag agtgcggcaa cac                    33

<210> SEQ ID NO 20
<211> LENGTH: 30
<212> TYPE: DNA
<213> ORGANISM: Artificial Sequence
<220> FEATURE:
<223> OTHER INFORMATION: Synthetic Primer

<400> SEQUENCE: 20 ggcggggat ccctgtgcct tctagttgcc                         30

<210> SEQ ID NO 21
<211> LENGTH: 28
<212> TYPE: DNA
<213> ORGANISM: Artificial Sequence
<220> FEATURE:
<223> OTHER INFORMATION: Synthetic Primer

<400> SEQUENCE: 21
ggcgggagat ctccatagag cccaccgc                          28

<210> SEQ ID NO 22
<211> LENGTH: 30
<212> TYPE: DNA
<213> ORGANISM: Artificial Sequence
<220> FEATURE:
<223> OTHER INFORMATION: Synthetic Primer

<400> SEQUENCE: 22
ggcggagatc tttagaaatt taagagatcc                        30

<210> SEQ ID NO 23
<211> LENGTH: 30
<212> TYPE: DNA
<213> ORGANISM: Artificial Sequence
<220> FEATURE:
<223> OTHER INFORMATION: Synthetic Primer

<400> SEQUENCE: 23
ggcgggagat ctatgatgga cccaaactcg                        30

<210> SEQ ID NO 24
<211> LENGTH: 31
<212> TYPE: DNA
<213> ORGANISM: Artificial Sequence
<220> FEATURE:
<223> OTHER INFORMATION: Synthetic Primer

<400> SEQUENCE: 24
ggcggagatc tatggcgtca cagaagagac c                      31

<210> SEQ ID NO 25
<211> LENGTH: 30
<212> TYPE: DNA
<213> ORGANISM: Artificial Sequence
<220> FEATURE:
<223> OTHER INFORMATION: Synthetic Primer

<400> SEQUENCE: 25

```
ggcgggagat cttcagcgtc tagccatggg                                    30
```

<210> SEQ ID NO 26
<211> LENGTH: 32
<212> TYPE: DNA
<213> ORGANISM: Artificial Sequence
<220> FEATURE:
<223> OTHER INFORMATION: Synthetic Primer

<400> SEQUENCE: 26

```
ggcggtctag agccgccacc atgcccatcg tg                                 32
```

<210> SEQ ID NO 27
<211> LENGTH: 33
<212> TYPE: DNA
<213> ORGANISM: Artificial Sequence
<220> FEATURE:
<223> OTHER INFORMATION: Synthetic Primer

<400> SEQUENCE: 27

```
ggcggggaat tctcacagca gcctggcctt gtg                                33
```

<210> SEQ ID NO 28
<211> LENGTH: 32
<212> TYPE: DNA
<213> ORGANISM: Artificial Sequence
<220> FEATURE:
<223> OTHER INFORMATION: Synthetic Primer

<400> SEQUENCE: 28

```
ggcgggagat ctcgccacca tggtgagcaa gg                                 32
```

<210> SEQ ID NO 29
<211> LENGTH: 31
<212> TYPE: DNA
<213> ORGANISM: Artificial Sequence
<220> FEATURE:
<223> OTHER INFORMATION: Synthetic Primer

<400> SEQUENCE: 29

```
ggcgggagat ctttacttgt acagctcgtc c                                  31
```

<210> SEQ ID NO 30
<211> LENGTH: 24
<212> TYPE: DNA
<213> ORGANISM: Artificial Sequence
<220> FEATURE:
<223> OTHER INFORMATION: Synthetic Primer

<400> SEQUENCE: 30

```
gcaggagatc ttatggcgcc ccgc                                          24
```

<210> SEQ ID NO 31
<211> LENGTH: 26
<212> TYPE: DNA
<213> ORGANISM: Artificial Sequence
<220> FEATURE:
<223> OTHER INFORMATION: Synthetic Primer

<400> SEQUENCE: 31

```
gcaggcggat cctcaaagag tgctga                                        26
```

<210> SEQ ID NO 32
<211> LENGTH: 30
<212> TYPE: DNA
<213> ORGANISM: Artificial Sequence

```
<220> FEATURE:
<223> OTHER INFORMATION: Synthetic Primer

<400> SEQUENCE: 32
ggcggggatc cttagaaatt taagagatcc                                          30

<210> SEQ ID NO 33
<211> LENGTH: 30
<212> TYPE: DNA
<213> ORGANISM: Artificial Sequence
<220> FEATURE:
<223> OTHER INFORMATION: Synthetic Primer

<400> SEQUENCE: 33
ggcgggagat ctatgatgga cccaaactcg                                          30

<210> SEQ ID NO 34
<211> LENGTH: 31
<212> TYPE: DNA
<213> ORGANISM: Artificial Sequence
<220> FEATURE:
<223> OTHER INFORMATION: Synthetic Primer

<400> SEQUENCE: 34
ggcggagatc tatggcgtca cagaagagac c                                        31

<210> SEQ ID NO 35
<211> LENGTH: 30
<212> TYPE: DNA
<213> ORGANISM: Artificial Sequence
<220> FEATURE:
<223> OTHER INFORMATION: Synthetic Primer

<400> SEQUENCE: 35
ggcgggggat cctcagcgtc tagccatggg                                          30

<210> SEQ ID NO 36
<211> LENGTH: 26
<212> TYPE: DNA
<213> ORGANISM: Artificial Sequence
<220> FEATURE:
<223> OTHER INFORMATION: Synthetic Primer

<400> SEQUENCE: 36
gcaggagatc taacagcacg ctgatc                                              26

<210> SEQ ID NO 37
<211> LENGTH: 27
<212> TYPE: DNA
<213> ORGANISM: Artificial Sequence
<220> FEATURE:
<223> OTHER INFORMATION: Synthetic Primer

<400> SEQUENCE: 37
gcaggcagat ctctagatag tctggta                                             27

<210> SEQ ID NO 38
<211> LENGTH: 53
<212> TYPE: DNA
<213> ORGANISM: Artificial Sequence
<220> FEATURE:
<223> OTHER INFORMATION: Synthetic Primer

<400> SEQUENCE: 38
gcaggagatc tagcggggca ggatccatgc tagtacttca atgggcctct ctg                53
```

<210> SEQ ID NO 39
<211> LENGTH: 33
<212> TYPE: DNA
<213> ORGANISM: Artificial Sequence
<220> FEATURE:
<223> OTHER INFORMATION: Synthetic Primer

<400> SEQUENCE: 39
gcaggcagat ctttatacat acctctcggc ctc                                    33

<210> SEQ ID NO 40
<211> LENGTH: 30
<212> TYPE: DNA
<213> ORGANISM: Artificial Sequence
<220> FEATURE:
<223> OTHER INFORMATION: Synthetic Primer

<400> SEQUENCE: 40
ggcgggggat ccggtacctg gtgtctattg                                        30

<210> SEQ ID NO 41
<211> LENGTH: 29
<212> TYPE: DNA
<213> ORGANISM: Artificial Sequence
<220> FEATURE:
<223> OTHER INFORMATION: Synthetic Primer

<400> SEQUENCE: 41
ggcgggagat ctcttcacaa tctgggtag                                         29

<210> SEQ ID NO 42
<211> LENGTH: 29
<212> TYPE: DNA
<213> ORGANISM: Artificial Sequence
<220> FEATURE:
<223> OTHER INFORMATION: Synthetic Primer

<400> SEQUENCE: 42
ggcgggagat cctgtgcctt ctagttgcc                                         29

<210> SEQ ID NO 43
<211> LENGTH: 28
<212> TYPE: DNA
<213> ORGANISM: Artificial Sequence
<220> FEATURE:
<223> OTHER INFORMATION: Synthetic Primer

<400> SEQUENCE: 43
ggcgggggat ccccatagag cccaccgc                                          28

<210> SEQ ID NO 44
<211> LENGTH: 32
<212> TYPE: DNA
<213> ORGANISM: Artificial Sequence
<220> FEATURE:
<223> OTHER INFORMATION: Synthetic Primer

<400> SEQUENCE: 44
ggcgggggat cccgccacca tggtgagcaa gg                                     32

<210> SEQ ID NO 45
<211> LENGTH: 31
<212> TYPE: DNA
<213> ORGANISM: Artificial Sequence
<220> FEATURE:
<223> OTHER INFORMATION: Synthetic Primer

```
<400> SEQUENCE: 45
ggcgggagat ctttacttgt acagctcgtc c                                    31

<210> SEQ ID NO 46
<211> LENGTH: 30
<212> TYPE: DNA
<213> ORGANISM: Artificial Sequence
<220> FEATURE:
<223> OTHER INFORMATION: Synthetic Primer

<400> SEQUENCE: 46
ggcggtctag attagaaatt taagagatcc                                      30

<210> SEQ ID NO 47
<211> LENGTH: 30
<212> TYPE: DNA
<213> ORGANISM: Artificial Sequence
<220> FEATURE:
<223> OTHER INFORMATION: Synthetic Primer

<400> SEQUENCE: 47
ggcggggaat tcatgatgga cccaaactcg                                      30

<210> SEQ ID NO 48
<211> LENGTH: 31
<212> TYPE: DNA
<213> ORGANISM: Artificial Sequence
<220> FEATURE:
<223> OTHER INFORMATION: Synthetic Primer

<400> SEQUENCE: 48
ggcggtctag aatggcgtca cagaagagac c                                    31

<210> SEQ ID NO 49
<211> LENGTH: 30
<212> TYPE: DNA
<213> ORGANISM: Artificial Sequence
<220> FEATURE:
<223> OTHER INFORMATION: Synthetic Primer

<400> SEQUENCE: 49
ggcggggaat tctcagcgtc tagccatggg                                      30

<210> SEQ ID NO 50
<211> LENGTH: 30
<212> TYPE: DNA
<213> ORGANISM: Artificial Sequence
<220> FEATURE:
<223> OTHER INFORMATION: Synthetic Primer

<400> SEQUENCE: 50
ggcgggggat ccggtacctg gtgtctattg                                      30

<210> SEQ ID NO 51
<211> LENGTH: 29
<212> TYPE: DNA
<213> ORGANISM: Artificial Sequence
<220> FEATURE:
<223> OTHER INFORMATION: Synthetic Primer

<400> SEQUENCE: 51
ggcgggagat ctcttcacaa tctgggtag                                       29

<210> SEQ ID NO 52
```

```
<211> LENGTH: 34
<212> TYPE: DNA
<213> ORGANISM: Artificial Sequence
<220> FEATURE:
<223> OTHER INFORMATION: Synthetic Primer

<400> SEQUENCE: 52
ggcgggggat ccccggattg gccgcctcca gcag                            34

<210> SEQ ID NO 53
<211> LENGTH: 35
<212> TYPE: DNA
<213> ORGANISM: Artificial Sequence
<220> FEATURE:
<223> OTHER INFORMATION: Synthetic Primer

<400> SEQUENCE: 53
ggcgggggat ccgacgagag actgcgggaa gacac                           35

<210> SEQ ID NO 54
<211> LENGTH: 34
<212> TYPE: DNA
<213> ORGANISM: Artificial Sequence
<220> FEATURE:
<223> OTHER INFORMATION: Synthetic Primer

<400> SEQUENCE: 54
ggcgggggat ccccggattg gccgcctcca gcag                            34

<210> SEQ ID NO 55
<211> LENGTH: 35
<212> TYPE: DNA
<213> ORGANISM: Artificial Sequence
<220> FEATURE:
<223> OTHER INFORMATION: Synthetic Primer

<400> SEQUENCE: 55
ggcgggagat ctgacgagag actgcgggaa gacac                           35

<210> SEQ ID NO 56
<211> LENGTH: 34
<212> TYPE: DNA
<213> ORGANISM: Artificial Sequence
<220> FEATURE:
<223> OTHER INFORMATION: Synthetic Primer

<400> SEQUENCE: 56
ggcgggggat ccggagccag agatagggag agtc                            34

<210> SEQ ID NO 57
<211> LENGTH: 33
<212> TYPE: DNA
<213> ORGANISM: Artificial Sequence
<220> FEATURE:
<223> OTHER INFORMATION: Synthetic Primer

<400> SEQUENCE: 57
ggcgggggat cccagccaga gacagcgaca gag                             33

<210> SEQ ID NO 58
<211> LENGTH: 36
<212> TYPE: DNA
<213> ORGANISM: Artificial Sequence
```

```
-continued

<220> FEATURE:
<223> OTHER INFORMATION: Synthetic Primer

<400> SEQUENCE: 58
ggcgggggat cccccactgc agaggcaatc aacaag                                36
```

METHOD FOR IDENTIFYING TARGET EPITOPES OF THE T CELL MEDIATED IMMUNE RESPONSE AND FOR ASSAYING EPITOPE-SPECIFIC T CELLS

This application claims priority to PCT/DE 02/04270, filed on Nov. 20, 2002. The entire content of this application is incorporated by reference.

The present invention relates to a method for the detection of epitope-specific T-cells and target epitopes of reactive T-cells. Furthermore, the present invention relates to vectors comprising a first promoter which is specifically inducible by the epitope-specific contact with a T-cell in antigen-presenting cells, a nucleic acid which is functionally linked to this first promoter and which encodes a marker gene, a second promoter which is constitutive in antigen-presenting cells, and a nucleic acid which is functionally linked to said second promoter. Furthermore, the present invention relates to antigen-presenting cells which are transduced with the vectors according to the invention.

The acquired branch of the immune system consists of a humoral (immunoglobulins) and a cellular immune defense. Cellular and pathogen-specific polypeptides are processed by cells by specific cleavage and fragments (epitopes) thereof are presented together with MHC-molecules of the class-I and/or -II on the surface of antigen-presenting cells (APC). By means of their T-cell receptor T-cells specifically recognise epitopes which are presented in the complex with the body's own MHC-proteins and initiate an immune reaction.

T-cells can be partitioned into different effector populations on the basis of specific surface proteins. CD4$^+$ T-helper cells play a central role in the control of the immune defense. After a specific recognition of epitopes being presented to them on the surface of APC together with MHC-proteins, they regulate the production of antibodies by B-cells (humoral branch of the immune response) by the secretion of different messenger substances (for example cytokines) and the activation of CD8$^+$ cytotoxic T-cells (CTL) (cellular branch of the immune response). The meaning of CD8$^+$ CTL resides in the recognition and the destruction of degenerated cells and tissues as well as cells and tissues which have been attacked by micro-organisms or parasites. T-cells therefore display a prominent mechanism for protection of the acquired immune system for the prevention and control of microbial, especially virus-contingent diseases and for the recognition and destruction of degenerated cells of the body.

Professional APC such as dendritic cells, monocytes, macrophages, but also non-professional APC such as B-cells play a central role both in triggering the T-cell-response against exogenous immunogens and also in the induction of a T-cell-tolerance against tissues in the body itself. The activation and proliferation of T-cells is accomplished by the simultaneous triggering of two signals. The first signal is transduced into the T-cell by the T-cell receptor which recognises an epitope in connection with MHC on the surface of APC. The second co-stimulating signal is mediated by the specific interaction of the co-stimulating molecules B7.1 (CD80) or B7.2 (CD86) on the APC with the cognate receptor (CD28) on the surface of the T-cell. In the absence of the co-stimulating signal the T-cell becomes anergic. Anergy describes a state in which the T-cells do not proliferate and do not react to an antigen.

The degree of activation of an APC and the composition of a foreign substance significantly decide on the profile of the induced immune response. Thus, the concentration and biochemical characteristics of a foreign substance as well as the presence or absence of immune-modulating substances (especially bacterial lipopolysaccharides (LPS), bacterial nucleic acids (with CpG-motives) and exogenous polypeptides (e.g. bacterial flagellin)) have a significant effect whether the cellular (Th-1 cell-mediated immunity) or the humoral branch (TH-2 cell-mediated immune response) of the immune system is activated or whether the immune response comes up tolerogenically.

In order to prevent undesired immune reactions against proteins and tissues of the body itself, auto-reactive T-cells are early eliminated (clonal deletion) or inactivated (anergy). Consequence is an antigen-specific tolerance against structures (polypeptides, cells, tissues and organs) of the body itself. In the case of auto-immune diseases these protection mechanisms are disturbed or only insufficiently developed. By now the causes forming the bases of the formation of said auto-immune diseases are only poorly understood. Possibly, structures of the body itself are wrongly recognised as foreign due to their similarity to polypeptides specific to pathogens and foreign tissue and damaged by misguided effectors of the acquired immune system (T-cells and/or antibodies) or even destroyed.

Besides this, in connection with chronically persisting viral infections it does not seldom amount to inflammatory processes, partly afflicting vital organs such as the liver (viral hepatides) although the immune response is targeted primarily against the structures which are pathogen-specific. In such cases, it is spoken of immunopathogenesis since the damage and the symptoms of the disease are primarily caused by the own immune system and not by the pathogen.

Similar immune reactions form the basis also of the rejection of transplanted tissues and organs. In this case a combination of foreign MHC-proteins of the donor and epitopes of the body itself is recognised as foreign by T-cells of the recipient and attacked.

In contrast to the above mentioned diseases, in the case of tumour diseases often an insufficient immune recognition can be observed. Frequently tumour infiltrating lymphocytes (TIL) can be detected attacking the tumour in a limited scope but having a specificity on molecular level which is mostly not known. The reason why these TILs are not able in vivo to eliminate the tumour is unclear. The concentration of said TILs in the blood, usually being very low and often even under the threshold of detection, is presumably a decisive factor. For the stimulation and enhancement of such a tumour-specific immune response it is tried nowadays to stimulate TILs with tumour material ex vivo (outside of the body) and to bring them back into the body. In the case of other approaches tumour material from biopsies is labelled ex vivo by means of different antigens and brought back into the body after irradiation. The idea is hereby to make the tumour notable for the immune system by means of the new antigens and to stimulate thereby also TILs against naturally important tumour associated antigens by the destruction of tumour cells in vivo. However, these approaches are effective only in a very limited scope since the tumour cells can hardly stimulate an immune reaction. On the one hand, the reasons reside in the low concentration of specific antigens. On the other hand, the lack of co-stimulating molecules or MHC molecules leads to an inefficient presentation.

Moreover, the cellular immune response plays a central role in the control of numerous viral infects like for example HIV infections or herpes virus infections. Taking into consideration the importance of the cellular immune response in the control of microbial infects and tumours, at present manifold new immunisation strategies for the induction of antigen-specific T-cells are being tested. These comprise the application of live attenuated viruses and bacteria, recombinant live vaccines (based on different recombinant bacteria and viruses), particulate immunogens, (lipo-) proteins, (lipo-) peptides and DNA-vaccines. In addition, different forms of administration of these groups of vaccines, for example the combination of different vaccines in the "prime-boost" method and the combined administration with adjuvants and carrier substances, are tested for their applicability for the induction of a T-cell response. Most of the mentioned immunisation vectors are principally suited to elicit also a $CD8^+$ T-cell-mediated cytotoxic immune response besides a $CD4^+$ T-helper cell response. However, the efficiency of these methods for the targeted induction of an efficient $CD8^+$ T-cell response is up to now limited by the fact that in the case of very many diseases induced by micro-organisms and in the case of tumours the target epitopes of the protective T-cells are unknown, or only known to a limited number. The targeted insertion of rationally selected T-cell epitopes would lead to a significant increase of effectivity and efficiency of the beforehand described immunisation vectors.

Particularly in the case of vaccines and immunisation vectors with a limited capacity for the insertion of foreign genes (particularly DNA-vaccines, repticons, recombinant bacterial and viral vectors) or foreign epitopes (particularly vaccines based on peptides, polypeptides, lipoproteins and chimeric particulated immunogens) the knowledge of relevant target structures of the T-cell response is of decisive importance. In the case of the untargeted expression of a great number of epitopes it can furthermore amount to a redirection of the immune response to non-relevant targets because of (to a great extent unknown) epitopes.

By the presently available immunological techniques for the identification of target epitopes of reactive T-cells the APC are usually changed in such a way, that they present previously selected epitopes of polypeptides on their surface. The altered APC are hereby incubated together with autologous T-cells, or such cells that correspond to the autologic T-cells in terms of the recognition of MHC-molecules, and specific reactions of the T-cells (for example proliferation, cytokine release or cytotoxic activity) are measured after a specific recognition of epitopes/MHC complexes on the surface of APC.

For this, APC are for example incubated with peptides or mixtures of different peptides containing potential or already known target epitopes of reactive T-cells. In the case of this experimental approach the peptides are directly loaded on membrane associated MHC-proteins. Alternatively, polynucleotides encoding polypeptides which contain potential target epitopes, or reactive T-cells can be introduced into APC by means of transduction of different recombinant transfer systems (plasmids, non-viral or viral vectors) and the polypeptides can be expressed in the APC. These are then processed in the cytoplasm of the APC, loaded on MHC proteins of the classes I and II and presented together with them on the surface of the APC.

Alternatively, an epitope-loading of MHC proteins can be achieved by an incubation of APC with polypeptides, (lipo-) proteins or (lipo-) protein aggregates. In order to increase the uptake of these polypeptides or polypeptide-complexes, these can be subjected to a treatment with physical (denaturation with heat) or chemical methods (sodium-dodecylsulfate (SDS), urea or acid treatment). Moreover, the fusion of the polypeptides with CpG-containing nucleic acids or polypeptides of the SV40 T-antigen enhances their uptake, processing and epitope presentation. Polypeptides that potentially bear any antigenic epitopes are beforehand purified from organs, tissues, cells, micro-organisms or any other biological material by biochemical means. In addition, the polypeptides can be produced recombinantly for example by the means of genetically modified cells, yeasts, bacteria or viruses and be purified from them. Furthermore, also the incubation of APC with vital or killed bacteria, yeasts, mammalian and insect cells producing the polypeptide, or with their lysates is suited for the introduction of these polypeptides into the MHC-class I and -II pathway of antigen processing and antigen presentation. Subsequently the in such a way pre-treated APC are co-cultivated with T-cells or T-cell-containing cell mixtures. The identification of polypeptides containing target epitopes of reactive T-cells is performed by the determination of characteristic reactions of reactive T-cells (for example proliferation, cytokine release or cytotoxic activity) due to a specific recognition of epitope/MHC complexes on the surface of the APC. The like also applies for the determination of tumour associated antigens being recognised by tumour infiltrating lymphocytes.

As an alternative to single polypeptides which have been selected beforehand, theoretically also a great number of polypeptides can be simultaneously tested for their recognition by T-cells. For this purpose, polynucleotides of a gene library are introduced into APC by means of different non-viral and viral transfer systems which for example encode all expressed polypeptides of a cell. The modified APC are again incubated with T-cells and distributed over the wells of micro-titre-plates. The identification of target epitopes or polypeptides containing target epitopes of reactive T-cells is again performed by the determination of a specific reaction of the T-cells. Since mixtures of different APC presenting different epitopes are concerned, the APC of one well showing T-cell recognition are again distributed over different wells of a further micro-titre-plate (limiting dilution) and again tested for a recognition by specific T-cells. This dilution method is repeated until each well that shows a measurable T-cell reaction statistically represents only derivatives of one epitope presenting APC.

However, none of the methods for the search for epitopes which are available by now is suited to determine the target epitopes of protective or auto-aggressive T-cells in the scope of an acceptable effort for costs and labour and at a speed and completeness which is required for the manifold, urgently needed prophylactic, therapeutic and diagnostic applications. The use of the above mentioned methods for the quick and all-embracing determination of T-cell epitopes fails in the first instance because of the problems given below.

The peptide loading of membrane associated MHC proteins on APC indeed represents a very efficient method for stimulation of T-cells, but there is the considerable restriction that only known peptide sequences can be tested by this method. There is the same limitation also for methods which are based on the incubation of the APC with purified polypeptides, (lipo-) proteins, (lipo-) protein aggregates, cell lysates or apoptotic polypeptide producing cells. Methods for transformation of APC with polynucleotides encoding these polypeptides show the same restrictions. This restriction on the few known epitopes or polypeptides can not be circumvented by an increase of the number of polynucleotides, polypeptides or cell lysates tested due to the complexity of the biological detection systems. So for example, the exact analysis of the T-cell recognition of a single protein with a medium size of 20-40 kDa (about 200 to 400 amino acids) requires the synthesis and examination of more than 50 overlapping peptides. According to recent estimates based on the results of the human genome project for the enlightenment of the human genome, the total number of the human genes ad up to about 30000. The total number of proteins being specifically expressed in a differentiated cell and which all may contain putative target epitopes of reactive T-cells is therefore clearly too high to be all-embracingly tested for the presence of T-cell epitopes by means of the molecular biological and biochemical methods, respectively, available by now.

Screening methods of gene libraries for the search for T-cell epitopes which are available at present have also two decisive limitations. Due to the very high time exposure of these analyses of several weeks and due to the limited life span of the modified APC and the T-cells in culture, these analyses usually can not be performed with primary APC and T-cells because of the limited ability to perform cell divisions. Instead, these analyses require the generation of immortalised T-cell and APC populations. In either case this step is very time consuming and because of the necessity of corresponding MHC patterns limited in its application.

Due to the use of immortalised T-cell lines furthermore a reduction of the originally polyclonal T-cell population to oligoclonal T-cell lines takes place. Even in the case of the analysis of tumour infiltrating lymphocytes in which single T-cell clones are accumulated, these have to be first subcloned for the purpose of analysis.

The use of arbitrarily selected peptides and polypeptides for the search for T-cells is therefore not feasible because of the high number of potential targets of a T-cell response and because of the MHC-restriction of the specific epitope recognition by T-cells as well as the extremely high costliness and time exposure for the production and purification of polypeptides and for the performance of the presently available methods for the search of epitopes.

For the detection of T-cells with a certain antigen specificity in a population of T-cells, the T-cells are co-incubated with APC which present specific epitopes. The detection of antigen-specific CD4$^+$ T-helper cells is subsequently performed either by the determination of the secretion of cytokine (by FACS, ELISPOT or ELISA technique), by the measurement of the T-cell proliferation (by determination of the incorporation of $^3$H tritium into the DNA of proliferating cells) after specific re-stimulation of the T-cells with polypeptides or epitopes with a suitable length or by the detection of epitope-specific T-cells by means of the dimer or tetramer technology.

The detection of specific CD8$^+$ T-cells (CTL) is performed by a co-cultivation of these cells with peptide loaded APC and the determination of the cytolytic activity of the CD8$^+$ CTL (for example by means of the $^{51}$chromium release assay) or by the measurement of the IFN-γ secretion from the CTL (by FACS, ELISPOT or ELISA technique). Alternatively, epitope-specific T-cells can be again specifically detected by means of the dimer or tetramer technology.

One of the disadvantages of the presently available methods for the detection of T-cells with a certain antigen-specificity resides in their low sensitivity. Up to now, it is only possible to measure the reaction of the T-cells as a result of an epitope-specific recognition of the APC. Thus, the sensitivity of the detection is directly dependent on the concentration of the epitope-specific T-cells. In the case of the screening of gene libraries this forms a particular disadvantage. Due to the relatively high number of polynucleotide fragments in a gene library the number of copies of the single polynucleotide fragments of the gene library is very low after the introduction into the APC.

A pre-stimulation of the T-cell population with epitope-presenting APC increases the concentration of cells and therefore the sensitivity of the detection. However, an in vitro re-stimulation is not feasible for certain applications in which there is to be discriminated between activated and non-activated T-cells, like for example in the case of the detection of auto-aggressive T-cells if multiple sclerosis is suspected.

The di- and tetramer technologies are new and elegant methods for the detection of epitope-specific CD8$^+$ and CD4$^+$ T-cells. However, restrictions of these methods concerning a broad application in the T-cell diagnostics reside in the very high expenses for the production of the di- and tetramers. In addition, the di- and tetramer technology is presently only available for a limited number of MHC types, especially for MHC-class I proteins which are frequently represented in the population. Moreover, this technique only allows the detection of defined epitope-specific T-cells with known MHC-restriction. The examination of T-cell reactivities against multiple epitopes with this method is only feasible with a great expense of time and costs.

Therefore, the present invention is based on the problem to provide a method for the identification of epitopes which are specifically recognised by reactive T-cells. Furthermore, the present invention is based on the problem to provide methods for the detection of epitope-specific T-cells.

The problem is solved by the subject-matter defined in the patent claims.

The following figures are to illustrate the invention.

FIG. 1 show in a schematic view the arrangement of the promoters and the functionally linked nucleic acids in the vector according to the invention. ($P_2$) denotes a promoter being constitutively active in APC, (PP) denotes any polypeptide, ($P_1$) denotes a promoter being inducible in APC by the epitope-specific contact with a T-cell, (M) denotes a marker, (L) denotes a signal peptide, (LY) denotes an endo/lysosomal targeting signal, (TD) denotes a heterologous transmembrane domain, RE denotes restriction sites, ori means the origin of replication and R means resistance gene.

Figure 2:
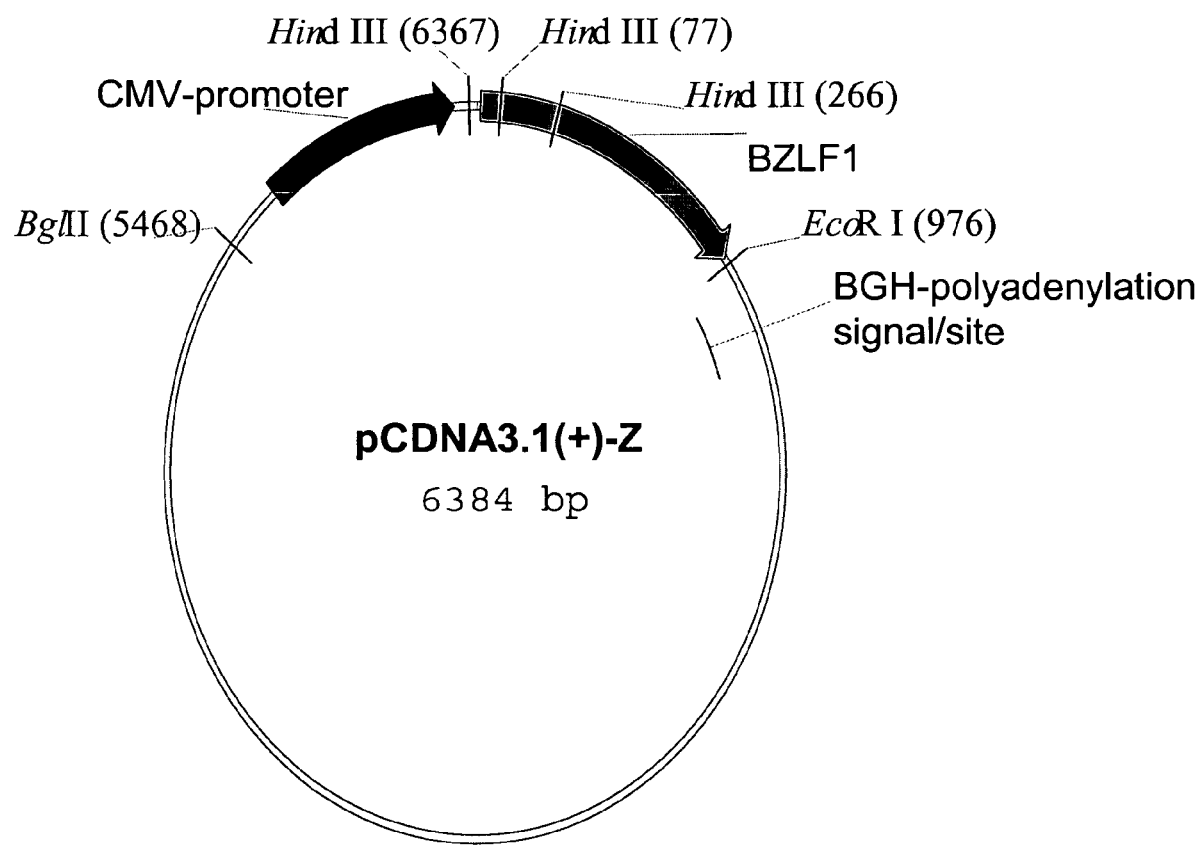

FIG. 2 exemplarily shows the vector backbone pcDNA3.1 (+)-Z according to the invention for vector backbones concerning the expression of polypeptides under the control of a promoter being constitutively active in APC ($P_2$). This plasmid backbone contains the coding region of the Epstein-Barr virus BZLF-1 protein under the transcriptional control of the cytomegalo virus (CMV)-promoter which is constitutively active in APC.

Figure 3:
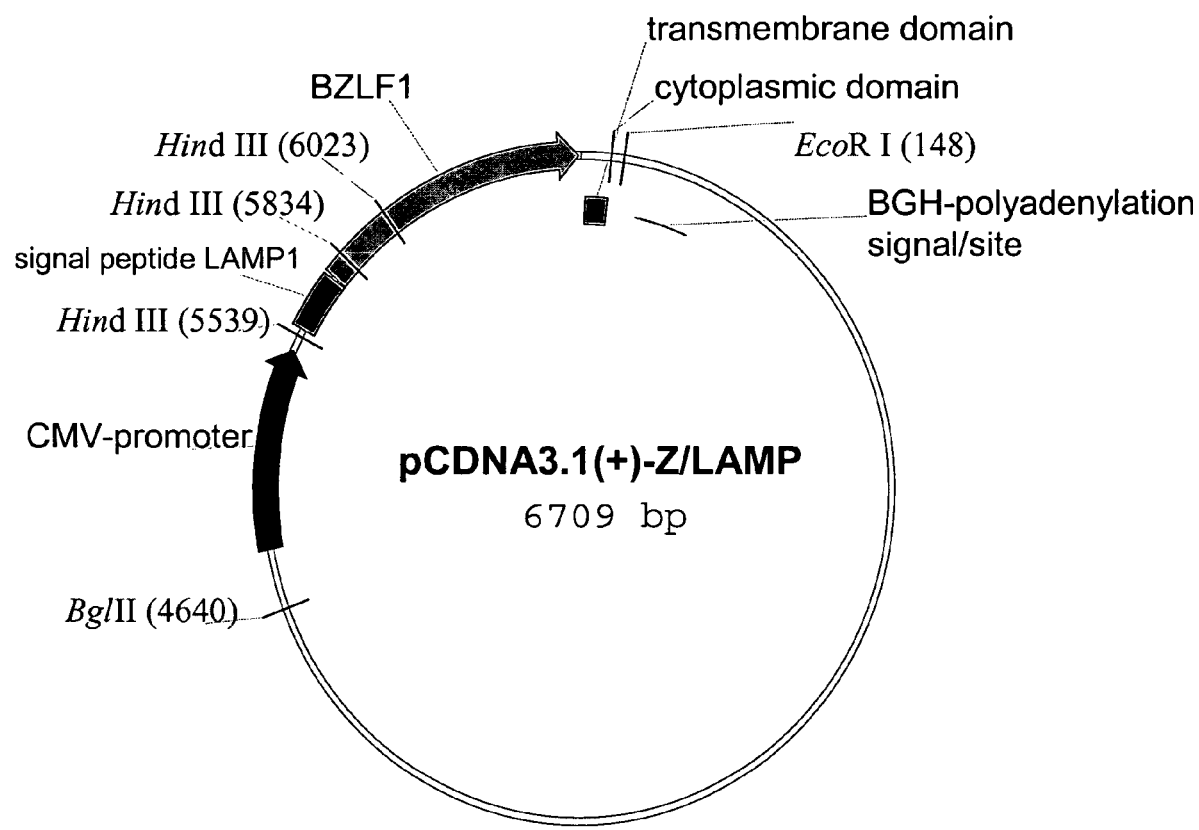

FIG. 3 exemplarily shows the vector backbone pcDNA3.1 (+)-Z/LAMP according to the invention for vector backbones which mediate a targeted transport into the endolysosom of the polypeptides which have been expressed by means of the constitutive promoter ($P_2$). This plasmid backbone contains the coding region of the Epstein-Barr virus BZLF-1 protein which is linked to the coding region of the LAMP-1 signal peptide in the 5'-region and with the coding region of the transmembrane and cytoplasmatic domain of the human LAMP-1 protein in the 3'-region. The coding region of the chimeric protein is under the transcriptional control of the cytomegalo virus (CMV)-promoter which is constitutively active in APC.

Figure 4:
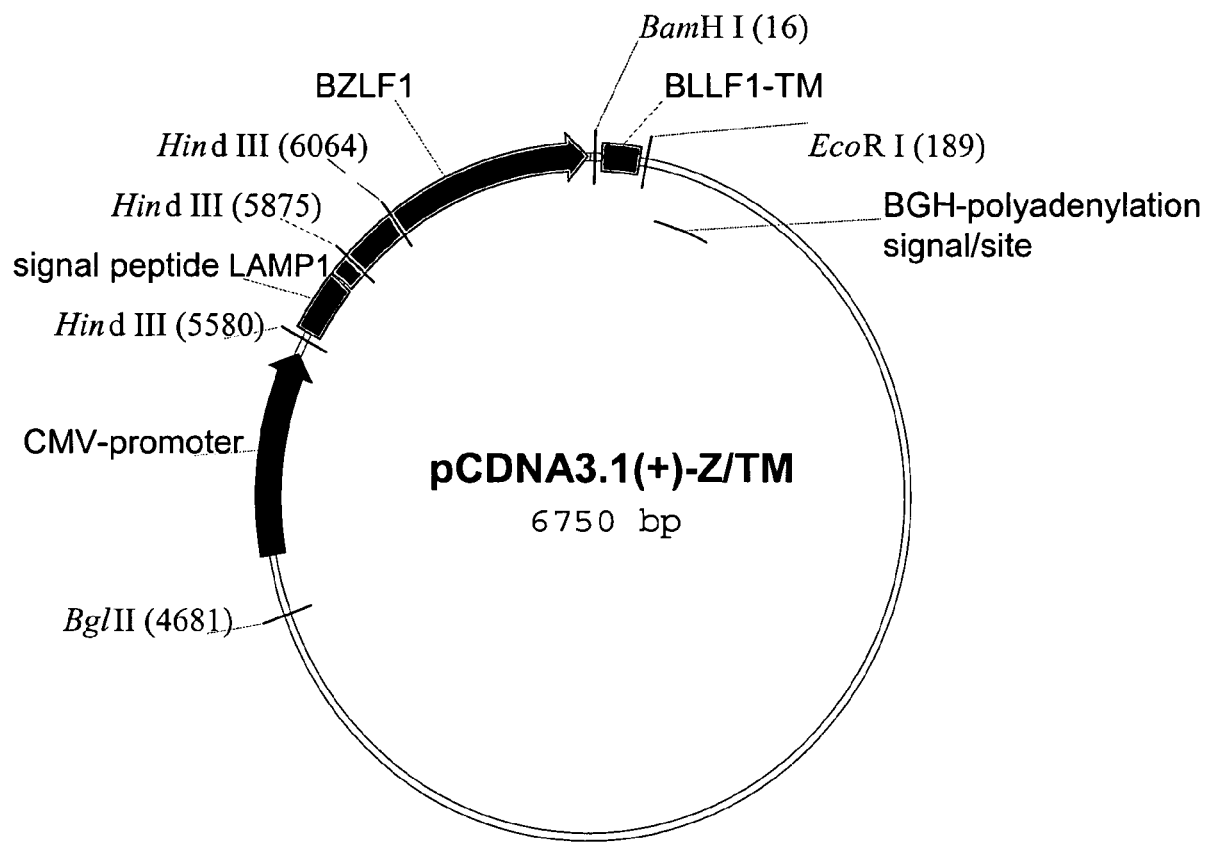

FIG. 4 exemplarily shows the vector backbone pcDNA3.1 (+)-Z/TM according to the invention for vector backbones which ensure a membrane anchoring of the polypeptides which have been expressed by means of the constitutive promoter ($P_2$). This plasmid backbone contains the coding region of the Epstein-Barr virus BZLF-1 protein which is linked to the coding region of the LAMP-1 signal peptide in the 5'-region and with the coding region of the transmembrane domain of the Epstein-Barr virus gp220/350 coat protein in the 3'-region. The coding region for the chimeric protein is under the transcriptional control of the cytomegalo virus (CMV)-promoter which is constitutively active in APC.

The FIGS. 5A-D exemplarily show four vector backbones according to the invention comprising a first promoter ($P_1$) which is specifically inducible in antigen-presenting cells by the epitope-specific contact with a T-cell, a nucleic acid being functionally linked to this first promoter and encoding a marker gene, a second promoter ($P_2$) which is constitutive in antigen-presenting cells, and a nucleic acid being functionally linked to this second promoter.

Figure 5A:
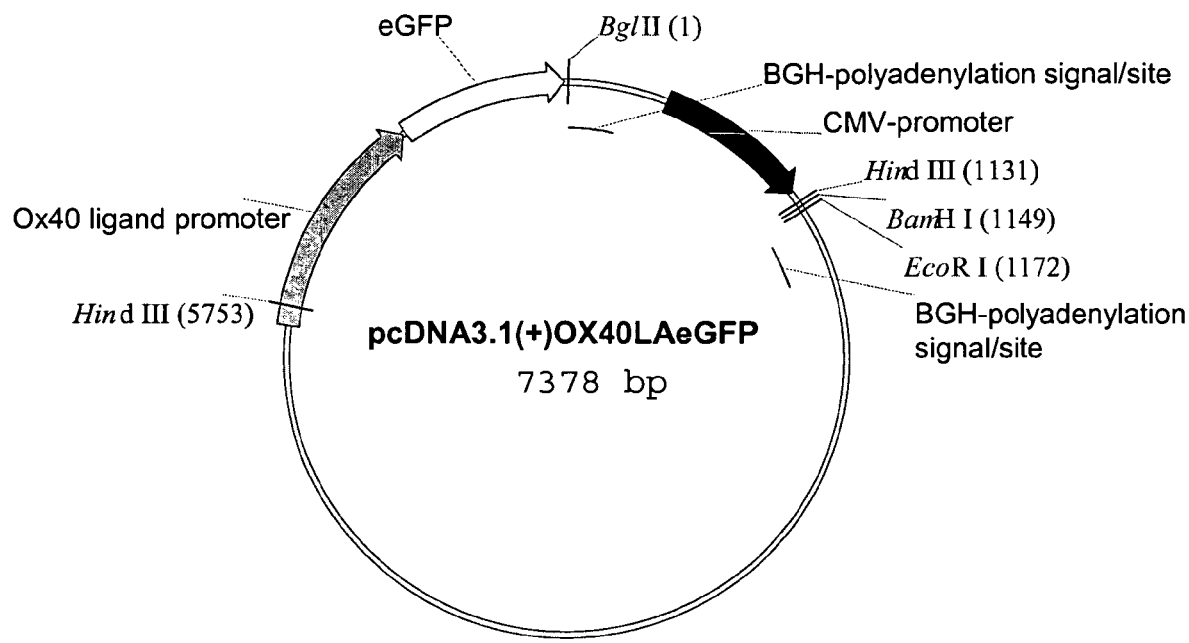

FIG. 5A shows the vector backbone pcDNA3(+)OX40LAeGFP according to the invention. This plasmid backbone contains the gene for the enhanced green fluorescent protein (eGFP) as a marker under the transcriptional control of the OX40-ligand promoter which is inducible in APC after an epitope-specific recognition by a T-cell.

Figure 5B:
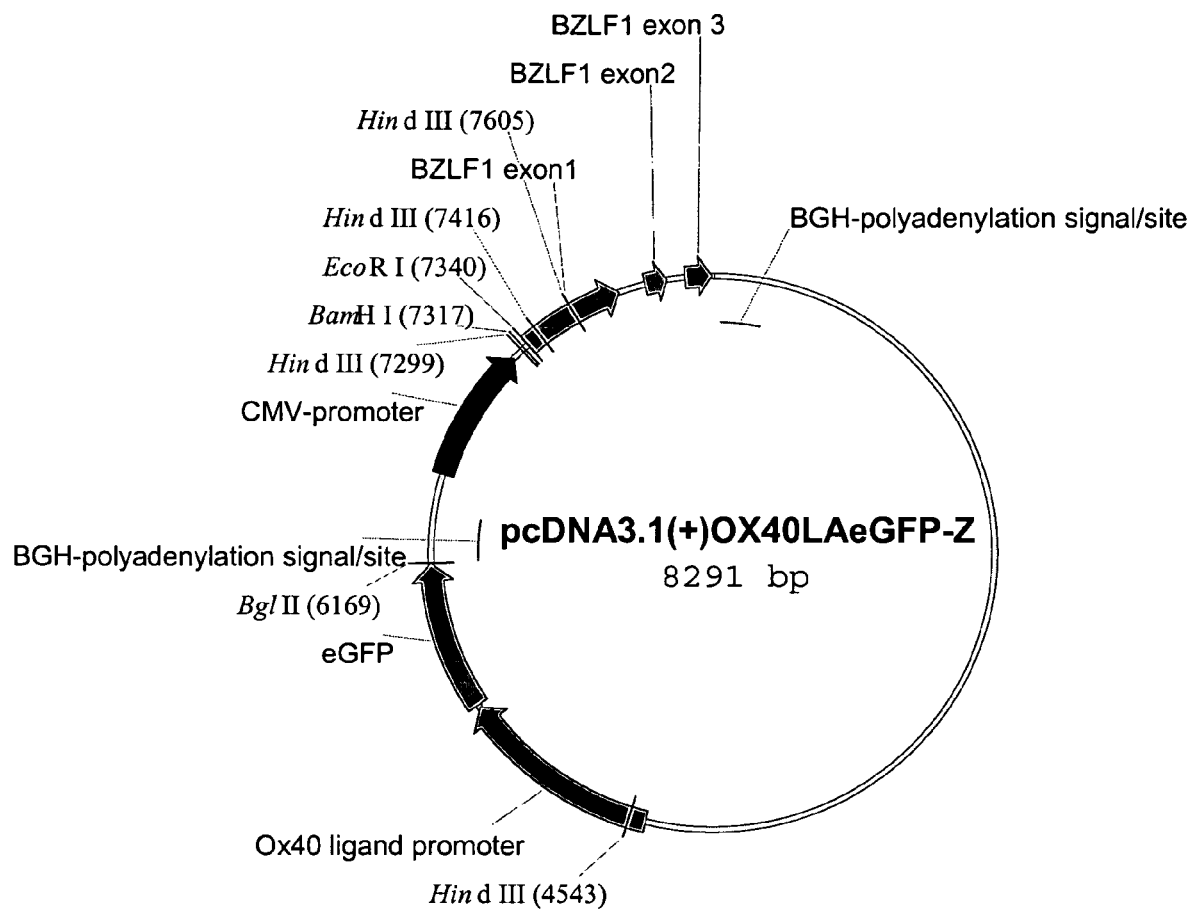

FIG. 5B shows the vector pcDNA3(+)OX40LAeGFP-Z according to the invention. This plasmid contains the gene for eGFP as a marker under the control of the inducible OX40-ligand promoter. In addition, this plasmid contains the coding region of the Epstein-Barr virus BZLF-1 protein under the transcriptional control of the cytomegalo virus (CMV)-promoter which is constitutively active in APC.

Figure 5C:
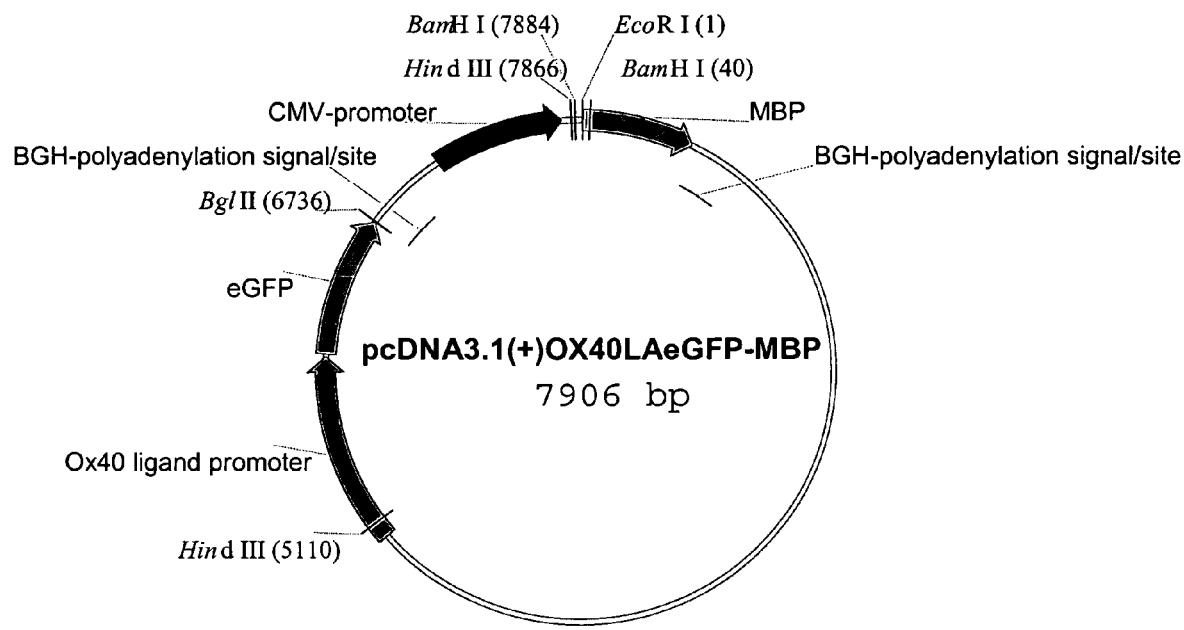

FIG. 5C shows the vector pcDNA3(+)OX40LAeGFP-MBP according to the invention. This plasmid contains the gene for eGFP as a marker under the control of the inducible OX40-ligand promoter. In addition, this plasmid contains the coding region of the human myelin basic protein (MBP) under the transcriptional control of the cytomegalo virus (CMV)-promoter which is constitutively active in APC.

Figure 5D:
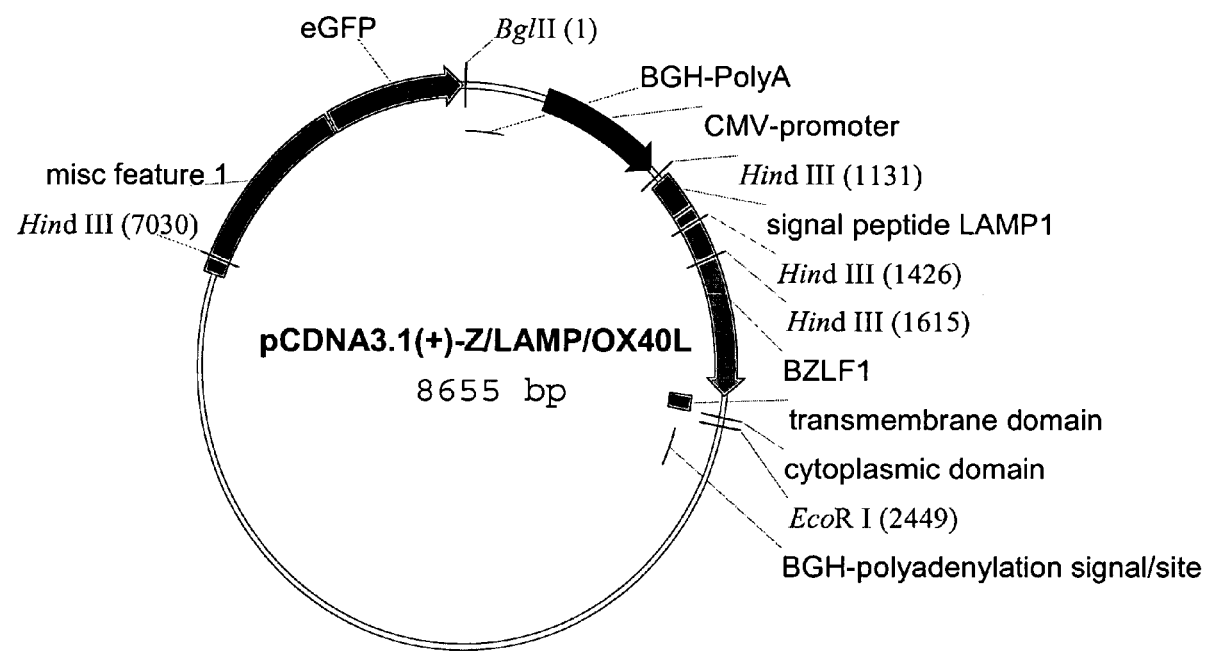

FIG. 5D shows the vector pcDNA3.1(+)Z/LAMP/OX40L according to the present invention. This plasmid backbone contains the coding region of the Epstein-Barr virus BZLF-1 protein which is linked to the coding region of the LAMP-1 signal peptide in the 5'-region and with the coding region of the transmembrane domain of the Epstein-Barr virus gp220/350 coat protein in the 3'-region. The coding region of the chimeric protein is under the transcriptional control of the cytomegalo virus (CMV)-promoter which is constitutively active in APC. In addition, this plasmid contains the gene for eGFP as a marker under the control of the inducible OX40-ligand promoter.

Figure 6A:
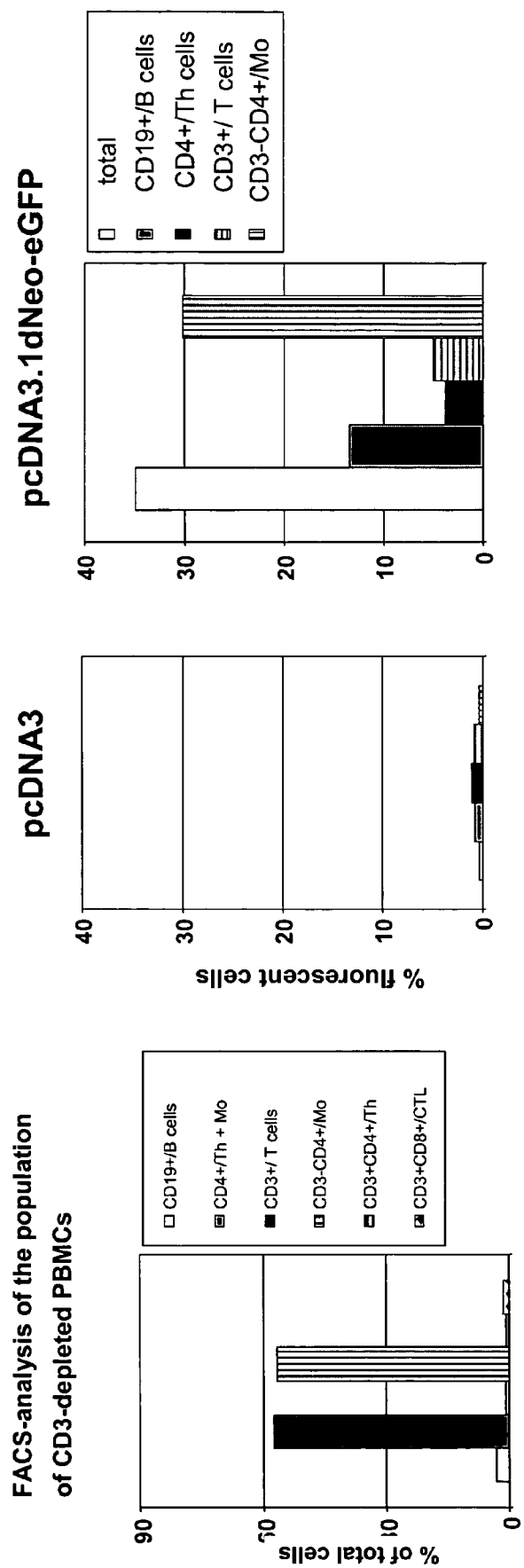
Figure 6B:
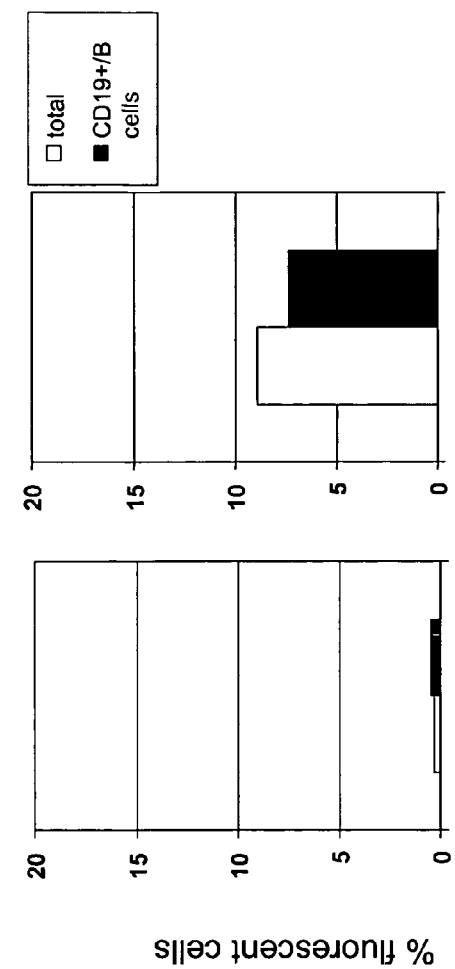
Figure 6B:
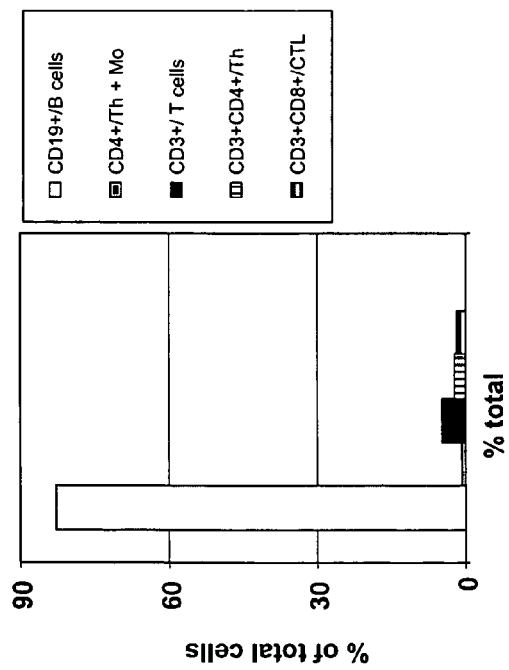

The FIGS. 6A-B show the efficiency of the plasmid transfer into APC by means of the Nucleovector™ technology. Hereby either populations of $CD3^+$ depleted PBMCs (FIG. 6A) or of purified B-cells (FIG. 6B) were prepared by means of the Miltenyi cell separation technology and the composition of the obtained cell populations was determined by means of the FACS technology using suitable antibodies (FIGS. 6A,B; left panel each). $3 \times 10^5$ purified $CD3^+$ cell-depleted PBMC or isolated B-cells each were subsequently transfected with 5 μg of the vector pcDNA3.1(+)dNeo-eGFP according to the present invention (FIGS. 6A,B; right panel each) and as a control with the pcDNA3.1(+) vector (FIGS. 6A,B; middle panel each) using the Nucleovector™ technology. The efficiency of the transfer of the nucleic acids in the denoted cell populations was determined by the measurement of the number of fluorescent cells (detection of a GFP-reporter) after 17 hours after transfection using a FACS device.

FIG. 7 shows the nucleic acid sequence of the human OX40-ligand promoter which was amplified by PCR (SEQ ID NO: 1).

The FIGS. 8A-D show the nucleic acid sequences of the human 4-1 BB-ligand promoter (4-1 BBL) which was amplified by PCR and of three variants of the human 4-1 BB-ligand promoter with progressive truncations in the 5'-region. FIG. 8A: long variant (V1) (SEQ ID NO: 2); FIG. 8B: C-terminally truncated variant (V2) (SEQ ID NO: 3); FIG. 8C: C-terminally further truncated variant (V3) (SEQ ID NO: 4); FIG. 8D: C-terminally even further truncated variant (V4) (SEQ ID NO: 5). The BglII restriction site which is present in the sequences is marked. This restriction side was mutagenised by a G to A exchange. The herein used term "genomic" denotes the collectivity of fragments of the genetic material of an organism.

The herein used term "polynucleotide" denotes the polymeric form of nucleotides of any length, preferentially desoxyribonucleotides (DNA) or ribonucleotides (RNA). This term denotes only the primary structure of the molecule. The term comprises double- and single stranded DNA and RNA as well as antisense-polynucleotides.

The herein used term "control sequences" denotes polynucleotide sequences which are necessary for the expression of coding polynucleotide sequences, they are linked to. Control sequences are present in the genome of organisms and regulate the transcription of genes, i.e. the synthesis of mRNA. Control sequences are present also on mRNA-polynucleotides and regulate the translation, i.e. the synthesis of polypeptides. The features of such control sequences vary in the dependency on the host organism; in the case of prokaryotes such control sequences contain usually a promoter, a ribosomal entry site and a transcription termination sequence; in eukaryotes such control sequences usually contain promoters and transcription termination sequences. In addition, the term "control sequence" comprises all polynucleotides whose presence is necessary for the constitutive or inducible expression of coding sequences and moreover includes additional components whose presence is beneficial for the expression of a polypeptide, like for example leader sequences and the sequences of a fusion partner.

The herein used term "polypeptide" denotes a polymer of amino acids of any length. The term polypeptide comprises also the terms (target-) epitope, peptide, oligopeptide, protein, polyprotein, and aggregates of polypeptides. Likewise, this term includes polypeptides which show post-translational modifications like for example glycosylations, acetylations, phosphorylations and similar modifications. Furthermore, this term comprises for example polypeptides which show one or more analogues of amino acids (e.g. unnatural amino acids), polypeptides with substituted linkages as well as other modifications which are state of the art, independent of the fact whether they occur naturally or if they are of non-natural origin.

The herein used term "epitope" denotes the region of a polypeptide exhibiting antigenic features and serving for example as a recognition site of T-cells or immunoglobulins. In terms of this invention epitopes are for example such regions of polypeptides which are recognised by immune cells like for example $CD4^+$ T-helper cells, $CD8^+$ cytotoxic T-cells, $CD161^+$ NKT cells or $CD4^+CD25^+$ regulatory T-cells. An epitope can comprise 3 or more amino acids. Usually an epitope consists of at least 5 to 7 amino acids or, more often, of at least 8-11 amino acids, or of more than 11 amino acids, or of more than 20 amino acids, less frequently even of more than 30 amino acids. The term "epitope" comprises both linear and a steric conformation being unique for the epitope. The steric conformation results from the sequence of the amino acids in the region of the epitope.

The herein used term "micro-organism" denotes viruses as well as prokaryotic and eukaryotic microbes such as archaebacteria, bacteria, protozoa and fungi; the latter group comprises for example yeast and filamentous fungi.

The herein used term "vector" or "gene-transfer vector" denotes naturally occurring or artificially generated organisms and constructs for the uptake, propagation, expression or transfer of nucleic acids in cells. Vectors are for example viruses such as lenti viruses, retro viruses, adeno viruses, adeno-associated viruses, pox viruses, alpha viruses, baculo viruses, rabies viruses or herpes viruses. Vectors are for example also bacteria such as listeriae, shigellae or salmonellae. But vectors are for example also naked DNA such as bacterial plasmids and MIDGES, virus derived plasmids, phagemids, cosmids, bacteriophages or artificially generated nucleic acids such as artificial chromosomes. Vectors are able to propagate autonomously inside a cell. Furthermore, the vector can contain one or more additional polynucleotides in such a way that these can be replicated and/or expressed. Moreover, vectors can contain one or more selection marker(s).

T-cells in terms of the invention are lymphocytes with regulatory or cytolytic features like for example $CD4^+$ T-helper cells, $CD161^+$ NKT cells, $CD8^+$ cytotoxic T-cells and $CD4^+CD25^+$ regulatory T-cells.

The used term "antigen presenting cell" (APC) comprises cells which are able to take up polypeptides, to process them and to present fragments of these polypeptides (epitopes) to the immune system in connection with MHC I and MHC II proteins. In particular, the term "antigen presenting cell" comprises dendritic cells (Langerhans cells), monocytes, macrophages, B-cells but also vascular endothelial cells and different epithelial, mesenchymal cells as well as microglia cells of the brain.

The term "linked" denotes an attachment by means of covalent bonds or strong, non-covalent interactions (e.g. hydrophobic interactions, hydrogen bonds, etc.). Covalent bonds can be for example ester, ether, phosphor-ester, amides, peptides, imides, carbon-sulphur bonds, carbon-phosphate bonds or similar bonds.

One aspect of the present invention relates to vectors comprising a first promoter ($P_1$) which is specifically inducible in APC by the epitope-specific contact with a T-cell, a nucleic acid encoding a marker gene and being functionally linked to said first promoter, a second promoter ($P_2$) which is constitutive in APC, and a nucleic acid which is functionally linked to said second promoter. Preferably, the vector contains preferably a bacterial origin of replication (ori) and a resistance gene. Furthermore, the vector according to the invention may contain suitable recognition sequences for restriction endonucleases flanking the constitutive second promoter ($P_2$), the nucleic acid sequence which is functionally linked to this second promoter as well as the bacterial origin of replication and the coding sequence for the bacterial resistance. Furthermore, the vector according to the invention can contain a third promoter which is functionally linked to yet another marker gene.

The polynucleotides encoding a marker are under the control of a promoter ($P_1$) which is inducible in APC due to an epitope-specific recognition by a T-cell. In terms of the invention suitable markers are for example, but not limited to, easily detectable polypeptides or fragments of polypeptides as well as arbitrarily modified derivatives thereof, which can be detected by simple enzymatic reactions or immunological techniques or because of their fluorescence. Examples for auto-fluorescent markers are the Vitality™ human recombinant (hr)GFP (Stratagene, Amsterdam, The Netherlands), the "green-fluorescent protein" (GFP) (BD Clontech, Heidelberg, Germany), FACS-optimised variants of the GFP, the "blue-fluorescent protein" (BFP), the "DsRed fluorescent protein" (BD Clontech), the "red-fluorescent protein" (RFP), the "yellow-fluorescent protein" (YFP), the "cyan fluorescent protein" (CFP) (BD Clontech) or derivates of these proteins, which show an increased fluorescence, like the "enhanced green-fluorescent protein" eGFP (BD Clontech), the "enhanced blue-fluorescent protein" eBFP, the "enhanced red-fluorescent protein" eRFP, the "enhanced cyan-fluorescent protein" eCFP (BD Clontech) or the "enhanced yellow-fluorescent protein" eYFP (BD Clontech). Examples for markers with enzymatic activity are for example the luciferase (LUC) (BD Clontech), the alkaline phosphatase (AP) (BD Clontech), the secretory alkaline phosphatase (SEAP) (BD Clontech), the chloramphenicol acetyltransferase (CAT) (Promega, Mannheim, Germany), the photinus-luciferase (BD PharMingen), the β-glucuronidase (GUS) (Research Diagnostics, New York, USA), the renilla-luciferase (Promega) and the β-galactosidase (β-Gal) (BD Clontech). Examples for markers which can be easily detected by means of immunological methods are in addition any intra-cellular and membrane-associated polypeptides which do not occur naturally in the APC being modified by the vectors according the invention and which are detectable by means of common immunological or biochemical methods for example by means of polypeptide-specific antibodies. Therefore, the membrane-associated murine proteins CD4, CD5, CD8a, CD11b, CD11c, CD19, CD43, CD45, CD62L, CD90, are for example suited as markers, but not limited to, but also the proteins CD4, CD8a, CD45, CD45RA and CD134 (OX40) of the rat as far as they do not display an interfering cross-reactivity with the respective human surface proteins. Analogously, the human surface proteins like for example CD2, CD3, CD4, CD8, CD11b, CD14, CD15, CD16, CD19, CD22, CD27, CD30, CD45RO, CD45RA, CD56, CD69, CD138 are suited as markers for the detection of target epitopes of reactive T-cells by means of the method according to the invention in the case of non-human vertebrates. For the detection of all these proteins by the FACS-technology fluorescence-linked primary and secondary antibodies are suited (for example R-phycoerythrin (R-PE), peridin-chlorophyll c (PerCP), fluorescein (FITC), Texas Red (TX), allophycocyanin (APC), Tandem PE-TX, Tandem PE-Cy5, PE-Cy7, Tandem APC-Cy7). These are either commercially available (for example from the companies Becton Dickinson, Dako, Coulter) or they can be generated with commercially available kits following the manufacturer's protocol. Moreover, for example microbial, in particular viral coat proteins, like for example, but not limited to, the coat proteins of the human immune-deficiency virus (HIV), of the simian immune-deficiency virus (SIV), of the human T-cell leukaemia viruses (HTLV) and of the vesicular stomatitis virus (VSV) are suited as markers. But also coat proteins and structural proteins of any virus and bacterium are suited as markers. However, the test persons/patients to be analysed must not exhibit any natural antibodies against these marker proteins in their serum.

In addition, polypeptides are suited as markers which exhibit cell transforming features. Examples for such polypeptides are viral proteins like the adenoviral proteins E1A and E1B, the E6 and E7 proteins of the human papilloma virus, the great T-antigen of the SV40 virus, the LMP-1 protein of the Epstein-Barr virus (EBV) as well as the X antigen of the hepatitis B virus. In addition, other non-viral polypeptides with transforming features can be used, too.

In particular polypeptides are suited as markers whose expression is measurably increased as a result of an epitope-specific recognition of an APC by a T-cell in the APC. Examples for these polypeptides are the OX40-ligand (OX40L) and the 4-1 BB-ligand (4-1 BBL) (Ohshima et al., 1997, J. Immunol. 159, 3838-3848; den Haan and Bevan; 2000, PNAS 97, 12950-12952). In addition, the co-stimulatory proteins B7.1 (CD80), B7.2 (CD86) and the Fas ligand (FasL) are suited. In addition, in terms of the present invention any polypeptide is suited whose expression is measurably increased or reduced as a result of a specific recognition of an epitope being presented together with MHC proteins on the surface APC in the same APC.

Furthermore, polypeptides are also suited as markers which were generated by any combination of different naturally occurring polypeptides as well as polypeptide sequences which do not occur naturally. These polypeptides are suited as markers if they are detectable by immunologic, (bio)chemical or physical methods in the cytoplasm or on the surface of APC which have been modified by the transfer systems according to the invention.

The expression of the marker is under the control of a promoter (first promoter, $P_1$) which is inducible by the epitope-specific contact with a T-cell. In terms of the invention, hereby any promoter is suited which is turned on or shows a significant increase of its activity as a result of a specific interaction of the T-cell receptor (TCR) of a specific T-cell with a peptide which is presented in connection with MHC proteins in the APC on the surface of the APC which have been modified by the vector according to the invention. Examples of such promoters are promoters for the OX40-ligand (OX40L) and of the 4-1 BB ligand (4-1 BBL) (den Haan and Bevan, 2000). In addition, the promoters for the co-stimulatory proteins B7.1 (CD80), B7.2 (CD86) and the promoter for the Fas ligand (FasL) are suited. In addition, any promoter is suited in terms of the invention which is turned on or shows a measurable increase in its activity as a result of the specific recognition of an epitope which is presented together with MHC proteins on the surface of APC by a specific T-cell in the same APC.

Furthermore, suitable promoters in terms of the invention are such ones which are turned off or are measurably reduced in their activity as a result of a specific interaction of the T-cell receptor (TCR) of a specific T-cell with a peptide being presented in the APC on the surface of the APC which have been modified by the vectors according to the invention in connection with MHC proteins. Hereby the reduction of the expression of a polypeptide being naturally produced by APC but also the reduction of the expression of a marker in the APC as a result of an epitope-specific contact with a T-cell can serve for a selection criterion.

The vectors according to the invention encode a marker or a combination of two or more different markers which are under the control of the same or different inducible first promoters as described above. If two or more markers are present on the vectors according to the invention, only the first marker gene has to be under the transcriptional control of a promoter which is inducible in APC. The expression of further markers under the control of a constitutive promoter is for example suited for checking the transfection/transformation-efficiency of the APC which were treated with the vectors and transfer systems, respectively, according to the invention.

Furthermore, the vector according to the invention contains a second promoter ($P_2$) which brings about a constitutive expression of the nucleic acid, being functionally linked to it, in the APC. Genes of viruses that infect mammals are often expressed very efficiently in mammalian cells and show a broad host range. Therefore, the respective viral control sequences are particularly suited as promoter $P_2$ for the expression of gene sequences in mammalian cells. Some representatives of suited viral control sequences are for example the early SV40 promoter, the cytomegalo virus (CMV) promoter, the respiratory syncytial virus (RSV) promoter, the mouse mammary tumour virus (MMTV) LTR promoter, the human immune-deficiency virus type 1 (HIV-1) LTR promoter, the adeno virus major late promoter (Ad MLP) and the herpes simplex virus (HSV) promoter, and the promoter sequences derived thereof. Furthermore, also promoters of non-viral genes, like e.g. the murine 3-phosphoglycerate-kinase (PGK) promoter, the human PGK-1 promoter, the human ubiquitin C promoter, the human EF-1α promoter, the human β-casein promoter, the murine metallothioneine promoter, the human actin 5c promoter or the human ICI promoter are suited for the efficient expression of polynucleotides in mammals. If the control sequences (1) for the constitutive expression of the polypeptide and the (2) inducible expression of the marker are present on one vector, only such control sequences are suited for the constitutive expression of the polypeptide which do not interfere with the functionality according to the invention of the control sequences for the inducible expression of the marker.

Both functional regions (1) for the constitutive expression of the polypeptide and the (2) inducible expression of the marker are usually present on one vector. However, these both functional regions can be present also on separate vectors which are then co-introduced in one APC.

The nucleic acid which is functionally linked to the second constitutive promoter, encodes polypeptides which represent or contain known or putative targets of reactive T-cells. Thereby, the nucleic acid can exhibit a naturally occurring sequence or an arbitrary sequence. However, the nucleic acid sequence can also be derived for example from any genomic or cDNA library.

If the vectors according to the invention are supposed to be used in the search for epitopes, any nucleic acids encoding polypeptides with unknown, potential target epitopes of reactive T-cells, like for example polynucleotides from a cDNA library or a genomic library, can be cloned under the control of the constitutive promoter ($P_2$). The cDNA library can be for example a species-specific, a pathogen-specific, a tissue-specific, a development-specific or a subtractive library. A limitation concerning the size of the cloned polynucleotides does not exist. The cloned polynucleotides can exert any length, e.g. they can comprise less than 20 nucleotides or, occurring more frequently, 20 to 100 nucleotides, but also 100 to 500, 500 to 1,500 nucleotides, but also up to 5,000 nucleotides, more rarely up to 10,000 nucleotides, but also more than 10,000 nucleotides.

If the vectors according to the invention are to be used for the detection of epitope-specific T-cells, nucleic acids encoding polypeptides with known target epitopes of reactive T-cells can be cloned under the control of the constitutive promoter ($P_2$). The cloned polynucleotides can exert any length, e.g. they can comprise less than 20 nucleotides, or, occurring more frequently, 20 to 30 nucleotides, but also 30 to 100 nucleotides, 100 to 500 nucleotides, but also up to 1,000 nucleotides, more rarely up to 10,000 nucleotides.

The used arbitrary or known nucleic acids can be derived from humans or mammals, but also from any animals, parasites or micro-organisms, e.g. bacteria or viruses. But they can be derived from plants or algae, too. Moreover, they can be derived from prion proteins.

Examples for viruses whose polypeptides or fragments are encoded by the nucleic acid sequences being comprised by the vector according to the invention are listed in the following. Particularly significant viruses with partly (human) pathogenic features are for example, but not limited to, polio viruses, coxsachie viruses, echo viruses, entero viruses, rhino viruses, orthomyxo viruses (especially type A, B, C influenza viruses), paramyxo viruses (especially para-influenza viruses, mumps viruses, measles viruses, respiratory syncytial viruses (RS-virus), corona viruses, flavi (especially yellow fever, dengue, Japan B-encephalitis, tick-born encephalitis (FSME) viruses), the hepatitis C virus (HCV)), toga (especially alpha- and rubidi viruses) and bunya (especially the bunya, hanta, nairo, phlebo and tospo virus genera) viruses, rubella viruses, rabies viruses, arena viruses (especially the lymphocytic chorio-meningitis virus (LCMV) and the Lassa fever virus), gastroenteritis viruses (especially rota viruses, adeno viruses, calici viruses, astro viruses, corona viruses), retro viruses (especially type A, B, C and D retro viruses, lenti viruses (especially the human immune-deficiency viruses type-1 (HIV-1) and -2 (HIV-2)), the simian immune-deficiency virus (SIV), the feline immune-deficiency virus (FIV), and the bovine immune-deficiency virus (BIV)), spuma viruses, the human T-cell leukaemia viruses type-1 (HTLV-1) and -2 (HTLV-2)), parvo viruses (especially parvo virus B 19 and adeno associated viruses (AAV)), papova viruses (especially papilloma viruses, the virus of the progressive multifocal leukoencephalopathy (PML), BK-virus), adeno viruses, herpes viruses (especially the herpes simplex virus type-1 (HSV-1) and -2 (HSV-2), the varicella-zoster virus (VZV), the cytomegalo virus (CMV) and the Epstein-Barr virus (EBV), the human herpes viruses 6, 7 and 8 (HHV 6, 7 and 8), hepatitis viruses (especially the hepatitis A virus (HAV), hepatitis B virus (HBV), hepatitis D virus (HDV), hepatitis C virus (HCV), hepatitis E virus (HEV) and hepatitis G virus (HGV) as well as the transfusion-transmitted virus (TTV)) and pox viruses (especially orthopox viruses (like the human pox-virus, vaccinia viruses, cow pox viruses and para-pox viruses)). Furthermore, the polypeptide can be derived from viral pathogens which elicit rare sub-acute or chronic diseases (especially the Marburg and ebola viruses as well as the borna viruses).

For example, the polypeptides can be derived from important viruses which are pathogenic for animals. Significant representatives of viruses which are pathogenic for animals are for example, but not limited to, the equine morbilli virus (EMP), picoma viruses (especially entero viruses, aphto viruses (with the elicitor of the foot and mouth disease (FMD)), the vesicular stomatitis virus, paramyxo viruses (especially morbilli viruses, avian paramyxo viruses), pox viruses (especially capripox viruses), bunya viruses, reoviruses (especially orbi viruses), flavi viruses (especially pesti viruses), orthomyxo viruses (especially the influenza A virus), herpes viruses (especially alpha herpes viruses), rabies viruses, retro viruses (especially lenti viruses and C-type retro viruses), toga viruses, rhabdo viruses, bima viruses, corona viruses and calici viruses.

An all-embracing listing of viruses which are described at present was for example assembled by the international committee on taxonomy of viruses (ICTV) and is accessible via the internet (http://www.ncbi.nlm.nih.gov/ICTV/).

Examples for bacteria whose polypeptides or fragments are encoded by the nucleic acid sequences which are comprised by the vector according to the invention are listed in the following. In principal the polypeptides can be derived of any bacterium. However, they are preferentially derived from intracellular bacteria. Significant intracellular bacteria are for example, but not limited to, listeriae (especially *L. monocytogenes*), salmonellae (especially *S. typhimurium*) and mycobacteriae (especially *M. tuberculosis*).

Furthermore, the polypeptides can be derived from human pathogenic bacteria. Significant representatives of human pathogenic bacteria are for example, but not limited to, staphylococcae, streptococcae, enterococcae, neisseriae, enterobacteriae (especially *Escherichia coli* (*E. coli*), inclusively *E. coli* strains which are pathogenic for babies (EPEC), enteroaggregative *E. coli* strains (EAggEC), clebsiellae, enterobacter, serratia, proteus, citrobacter and typhoid salmonellae), enteritis salmonellae, shigellae, yersiniae), vibrionae (especially *Vibrio cholerae* und *Vibrio El Tor*), pseudomonades, burkholderia, stenotrophoma, acinetobacter, campylobacter, helicobacter (especially *Helicobacter pylori*), haemophilus, bordetellae, legionellae, listeriae, brucellae, francisellae, erysipelothrix, korynebacteriae, bacillus, clostridiae, bacteroides, prevotellae, porphyromonae, fusobacteriae, anaerobiospirillae, anaerorhabdus, anaerovibrio, butyrivibrio, centripedia, desulfomonas, dichelobacter, fibrobacter, leprotricha, megamonas, mitsuocella, ricenella, sebaldella, selenomonas, succinovibrio, succinimonas, tisserella, mycobacteria (especially *M. tuberculosis*, atypic mycobacteria (MOTT) and *M. leprae*), nocardia, treponema (especially *T. pallidum* and *T. carateum*), borreliae (especially *B. burgdorferi* and *B. recurrentis*), leptospirae, rickettsiae, coxiellae, ehrlichiae, bartonellae, mycoplasma (especially *M. pneumoniae* and *M. hominis*), ureaplasma, actinomycetes, chlamydiae. In addition, the polypeptides can be derived from further medically significant bacteria like for example tropheryma, pasteurella, branhamella, streptobacillus, spirillum and gardnerella.

Furthermore, the polypeptides can be derived from bacteria which are pathogenic for animals. Significant representatives of bacteria which are pathogenic for animals are for example, but not limited to, mycoplasma, bacillus (especially *Bacillus anthracis*), brucellae, mycobacteriae (especially *M. tuberculosis* and *M. bovis*), campylobacter, tritrichomona, leptospirae, rickettsiae, salmonellae, clostridiae, actinobacillae, clamydiae, echinococcae, listeriae, yersiniae, corynebacteriae und francisella.

Examples for fungi whose polypeptides or fragments are encoded by the nucleic acid sequences which are comprised by the vector according to the invention are listed in the following. Particularly significant (human) pathogenic fungi are for example, but not limited to, blastomy yeasts (especially candida, cryptococcus, malassetia), hyphal yeasts (especially aspergillus, trichphyton, microsporum, and epidermophyton), dimorphic fungi (especially histoplasma, blastomyces, coccidioides, paracoccidioides, sporothrix) and pneumocystis.

Examples for parasites whose polypeptides or fragments are encoded by the nucleic acid sequences which are comprised by the vector according to the invention are listed in the following. Significant representatives of human pathogenic parasites are in particular also protozoa like tryphanosoma, leishmania, trichomona, giardia, amoebae, plasmodia, toxoplasma, cryptosporidia, microsporidia. Significant representatives of human pathogenic parasites are in particular also trematodes like for example shistosoma as well as cestodes like for example tape worms and echinococcae as well as nematodes like for example trichuris, trichinella, strongyloides, ancyclostoma, necator, enterobius, ascaris and filaria. Significant representatives of parasites being pathogenic for animals are for example, but not limited to, protozoa (especially protomonades, diplomonades, polymastigida, amoebae, toxoplasms, coccidia), mirospores, helminthes, trematodes, cestodes and nematodes.

The polynucleotides encoding the polypeptides of humans, primates, other mammals, any other animals, parasites, micro-organisms, plants, algae or also polynucleotides encoding prion proteins can, in addition, be linked to each other in any manner.

But they can be also linked to any nucleic acids which encode functional polypeptides. Polypeptides with functional features are for example signal peptides for the polypeptide targeting into the endoplasmatic reticulum (ER), for example the signal peptides of mellitin, erytropoetin, the human interleukin-3, the human interleukin-8, the human LAMP-1 and -2 protein or the tPA signal sequence. But such polypeptides are also endo- and lysosomal signal sequences or polypeptides having endo- and lysosomal signal sequences like for example the cytoplasmatic region of the Ii chain or regions of the "invariant chain", or of LAMP-1, LAMP-2, LIMP-1 (CD63), LAP or MHC-class II proteins which contain endo/lysosomal signal sequences.

Such polypeptides are, in addition, polypeptides which represent transmembrane domains for example, but not limited to, the transmembrane domain of the Epstein-Barr virus gp220/350 coat protein, of the HIV gp41 transmembrane protein, but also any other transmembrane domains of other naturally occurring transmembrane proteins, but also synthetically generated transmembrane domains. The vectors according to the invention contain usually a bacterial origin of replication and a gene which brings about a resistance against for example ampillicin, kanamycin, tetracyclin or zeocin. The coding regions of the bacterial origin of replication and the antibiotic resistance are preferably located in proximity to the expression unit for the constitutive expression of polypeptides ($P_2$) with known or putative T-cell epitopes. The nucleic acids which are necessary for the constitutive expression of a polypeptide, the origin of replication and the resistance gene, can be flanked, on the vector according to the invention, on both sides by one or more recognition sequence(s) for restriction sites which preferentially is/are not present within the bordered nucleic acid sequence including the sequence for the origin of replication, the resistance gene and the expressing unit for the constitutive expression of the polypeptide with the known or putative T-cell epitopes. This part of the sequence on the vector can also be bordered by two different, however compatible, restriction sites for restriction endonucleases unless both restriction sites are present within the nucleic acid sequence comprising the origin of replication, the resistance gene and the expression unit for the constitutive expression of the polypeptide. The presence of these restriction sites for restriction enzymes is not required if episomally available plasmids are used as a transfer system for the vectors according to the invention.

Furthermore, the vector according to the invention can contain the following control sequences which are known to a person skilled in the art and which belong to the state of the art: transcription-termination and polyadenylation sequences, enhancer, introns with functional donor and acceptor sites for splicing as well as leader sequences, a TATA-box, a GC-box, a CAAT-box and other promoter elements which are usually localised upstream of the TATA-box as well as an optimal but also sub-optimal Kozak-sequence.

Expression cassettes are often contained within a replicon, like e.g. in extra-chromosomal elements (e.g. plasmids), being able to persist stably in a host like e.g. in a mammalian cell. Mammalian replication systems contain cassettes being derived from animal viruses, for example papova viruses, polyoma viruses, bovine papilloma viruses or from the Epstein-Barr virus and which require trans-active factors for the replication.

Moreover, the expression efficiency of the desired foreign gene can be increased by the choice and use of suited, host specific codons. This observation is based on the finding that both prokaryotic and eukaryotic genes do not exhibit a static usage of synonymous codons.

As vector backbones for the generation of plasmids according to the invention for example, but not limited to, pcDNA expression vectors are suited which are based on the prototype plasmid pBR322 (Bolivar et al. in: DNA Insertion Elements, Plasmids and S. Episomes. Bukhari, A., Shapiro J. A., and Adhaya S. L. (eds.) Cold Spring Harbor Laboratory, USA, pp. 686-687, (1977)) which allow an efficient gene expression in mammalian cells.

Furthermore, a multiplicity of different non-viral and viral gene transfer vectors is suited to introduce nucleic acids into mammalian cells. Some of the most significant vector systems for the gene expression in mammalian cells are listed in the review by Makrides (Makrides, Protein Expr. Purif. (1999), 17(7), 183-202). Many of the described vectors are particularly suited for the transduction of nucleic acids in APC and commercially available.

For example, plasmid DNA, in particular also the vectors according to the invention, can be used directly for the transduction of cells. In particular, a second generation of linear DNA plasmids, the so-called MIDGE-transfection vectors (Mologen AG, Berlin, Germany), is suited for the efficient transfer of the nucleic acids described in this patent specification. Different forms of application for the transduction of mammalian cells (for example, but not limited to, the lipofection, electroporation or calcium phosphate precipitation) as well as for the enhancement of the efficiency of the uptake of vectors are published and state of the art. Particularly suited for the transfer of nucleic acids in APC are for example the Femtosecond Laser Technology protocol (Tirlapur and Konig, (2001), Nature 418, 290), the Nucleovector™ technology (Amaxa, Germany) or the Fugene 6 Transfection reagent (Roche, Germany).

Moreover, the efficiency of the transfer of nucleic acids can be drastically enhanced by the use of miniature liposomes with a diameter of about 25 nm (Copernicus Therapeutics, USA).

The efficiency of the gene transfer via retro-viral transfer systems can e.g. be enhanced by adjusting the target cells in the S phase. In addition, the methods for optimising the efficiency of the transduction of mammalian cells via viral transfer systems comprise the variation of the "multiplicity of infection" (M.O.I.), the depletion of ions like e.g. phosphate ions, the addition of polycationic substances, for example of protamin sulphate, the variation of the period of contact, temperature, the pH value, a co-centrifugation of the cells and the virus and vector stocks, respectively, or the incubation of the cells with the transfer systems in a small volume of medium.

The transfer systems according to the invention which have been generated in such a way are both suited for the search for epitopes and for the detection of epitope-specific T-cells.

Therefore, the invention relates to the provision of gene transfer vectors for the modification of APC by means of these vectors. The vectors according to the invention transfer a combination of two characteristics onto the APC:

(1) The APC obtain the ability to constitutively and intracellularly produce single known target structures, e.g. in the case of an application in diagnostics, or still unknown potential target structures, e.g. in the case of the search for epitopes, and to present fragments thereof in connection with MHC-proteins of the classes I and/or II on their surface.

(2) In the case of the recognition of the target structure (epitope) presented on the surface of the APC by a specific T-cell, the expression of the marker is induced or inhibited via the signal in the APC which was elicited by the T-cell. The changed expression of the marker, and by this means the activated APC, can be reliably and rapidly detected in a simple and quantitative manner, for example by means of commercially available devices and methods (for example FACS-, immuno-fluorescence-, ELISA-, ELISPOT-technology) and be isolated (for example by FACSsorting, magnetic cell-sorting).

The APC which have been modified by means of the vectors according to the invention are suited for a quick detection and characterisation of up to now unknown target structures of T-cells and thus represent a suitable tool for the construction of disease- or patient-specific databases. In addition, the APC which have been modified by the vectors according to the invention can be used for the detection of any T-cell populations which have known target structures. The methods according to the invention apply to all vertebrates which have T-cells, in particular to humans, primates and rodents. The knowledge of up to now unknown target regions of activated T-cells, in addition, opens up new perspectives concerning the development of novel concepts in diagnostics, therapy and vaccination for the prophylaxis and treatment of pathogen-induced diseases, auto-immune diseases, transplant rejections and chronic inflammatory diseases. Moreover, the knowledge of T-cell epitopes in non-human vertebrates opens up the establishment of new animal model systems for research purposes.

A further aspect of the present invention relates to antigen presenting cells (APC) being transduced with the vectors according to the invention. The generation of APC according to the invention takes place by the treatment of APC with the gene transfer vectors according to the invention. The treatment of the APC with the gene transfer vectors according to the invention can take place by the incubation of heparinised whole blood or defined peripheral blood-mononucleated cells (PBMC) which were purified from the whole blood, as well as purified populations of defined APC (for example B-cells, dendritic cells, monocytes, macrophages) with viral and bacterial gene transfer vectors according to the invention which exhibit a specific tropism for all APC or for defined sub-populations of APC. Alternatively, in particular purified populations of PBMC and purified populations of defined APC (for example B-cells, dendritic cells, monocytes, macrophages) are suited for the treatment with the non-viral gene transfer vectors according to the invention, for example with plasmids, MIDGE vectors and replicons. These non-viral vectors are preferentially introduced into the target cells by means of physical/chemical methods (for example Femtosecond Laser technology, Nucleovector™-technology, transfection by means of the Fugene 6 reagent (Roche, Germany), but also by lipofection, or electroporation or calcium phosphate precipitation). Methods for the purification of PMBC and of defined populations of APC from heparinised whole blood as well as the nucleic acid transfer into APC by means of viral, bacterial as well as non-viral/non-bacterial vectors are state of the art.

The success of the transfer of the nucleic acids according to the invention can be verified by means of a detection of the expression of the polypeptide being under the control of the constitutive promoter (promoter $P_2$) or of the expression of the marker being under the control of the third promoter by conventional molecular biological and immunological methods, for example by the immuno-blot, the immuno-fluorescence or FACS technology with suitable antibodies being used. Such molecular biological and immunological methods for the specific detection of polypeptides are multiply published and state of the art.

For the generation of APC according to the invention for the search for epitopes, vectors according to the invention are used which exhibit inter alia any polynucleotides being under the control of the constitutively active promoter ($P_2$) which encode polypeptides with the potential target epitopes of reactive T-cells, for example polynucleotides of a (subtractive) gene library.

For the generation of APC according to the invention for the detection of epitope-specific T-cells, transfer systems according to the invention are used which exhibit inter alia defined polynucleotides being under the control of the constitutively active promoter ($P_2$) which encode one or more polypeptides with known target epitopes of reactive T-cells.

Furthermore, one aspect of the invention relates to APC for the search for epitopes or for the detection of epitope-specific T-cells which have been transduced with a vector corresponding to the gene transfer vectors according to the invention, with the limitation that said vector does not exhibit the expression unit for the marker comprising the promoter ($P_1$) which is inducible in APC and comprising the functionally linked nucleic acid encoding a marker gene.

A further aspect of the present invention relates to a method for the detection of epitope-specific T-cells and for the detection of target epitopes of reactive T-cells comprising the following steps:

a) Isolation of APC-containing and/or T-cell-containing body fluid, preferably blood or liquor,
b) contacting and transduction of APC-containing body fluid with gene transfer vectors according to the invention,
c) incubation of the body fluid containing the transduced APC or of isolated transduced APC with the body fluid containing T-cells or the isolated T-cells, preferably for 0.5 to 36 hours or longer, particularly preferred for 0.5 to 2, 2 to 6, 6 to 12, 12 to 36 hours or 36 to 168 hours,
d) detection of marker expressing APC, and
e) optionally, the isolation and characterisation of the nucleic acid which is functionally linked to the second promoter and which encodes the target epitopes of reactive T-cells.

Furthermore, the invention relates to a further method for the detection of epitope-specific T-cells and for the detection of target epitopes of reactive T-cells comprising the following steps:

a) Isolation of APC-containing and/or T-cell-containing body fluid, preferably blood,
b) contacting and transduction of APC-containing body fluid with a nucleic acid inter alia comprising a promoter ($P_2$) being constitutive in APC and comprising a nucleic acid being functionally linked to said promoter,
c) incubation of the body fluid containing the transduced APC or of isolated transduced APC with the body fluid containing the T-cells or the isolated T-cells, preferably for 0.5 to 36 hours or longer, particularly preferred for 0.5 to 2, 2 to 6, 6 to 12, 12 to 36 hours or 36 to 168 hours,
d) detection of marker expressing APC, and
e) optionally, isolation and characterisation of the nucleic acid which is functionally linked to the second promoter and encodes the target epitopes of reactive T-cells.

The vectors which are used in step b) of the further method correspond to the gene transfer vectors according to the invention, but have the limitation that said vectors do not contain the expression unit for the marker comprising the promoter ($P_1$) which is inducible in APC and the functionally linked nucleic acid encoding a marker gene. Besides, the used gene transfer vectors correspond in all functional regions to the gene transfer vectors according to the invention. In fact, in this method, instead of the expression units for the marker ($P_1$) encoded by the gene transfer vector, available genomic promoters are used which are measurably changed in their activity as a result of an epitope-specific recognition of the APC according to the invention by a T-cell as well as nucleic acids which are functionally linked in a natural way and which are used as functional units for the marker expression, i.e. induction or inhibition. The further method also comprises controllable genomic promoters which are functionally linked to polynucleotides that encode any user-defined marker.

Preferably, the APC-containing body fluid in step b) of the methods is blood, liquor, the purified PBMC population, or a separated APC population. Preferably, the isolated T-cells are $CD4^+$ T-cells, $CD8^+$ T-cells, $CD4^+ CD25^+$ regulatory T-cells, $CD161^+$ NKT cells, or any mixture of NKT, $CD4^+$, $CD8^+$ and $CD4^+CD25^+$ T-cells.

The detection and the quantification of epitope-specific T-cells and the search for target epitopes of reactive T-cells can for example be performed from patients who suffer from an auto-immune disease, a chronic inflammatory disease, a microbial infection, a tumour disease, or a transplant rejection, or also from healthy test persons or from participants in therapeutic or preventive studies. In addition, the detection of epitope-specific T-cells and the search for target epitopes of reactive T-cells can be performed by means of the APC according to the invention also in primates or other animals which posses T-cells.

For the performance of the method for example blood or another APC-containing and/or T-cell-containing body fluid is extracted from a test person or a patient and the APC are transduced with the gene transfer vectors according to the invention. The transduction of the APC with the vectors according to the invention can be performed in blood, purified PBMC populations, or in separated APC populations. The isolation of the purified or of the separated populations can be performed also after the transduction. The APC according to the invention which were generated this way, are subsequently incubated with isolated T-cell populations, in particular $CD4^+$ T-cells but also $CD8^+$ T-cells, $CD161^+$ NKT cells, $CD4^+CD25^+$ regulatory T-cells, any mixture of $CD4^+$, $CD8^+$, $CD4^+CD25^+$ and $CD161^+$ NKT cells, or also T-cell-containing cell mixtures, or T-cell-containing body fluid of the same patient for 0.5 to 2 hours, 2 to 6 hours or for 6 to 12 hours, or for 12 to 36 hours, or for 36 to 168 hours or for more than 168 hours, using suitable conditions for the cultivation, for example 37° C. in a humidified atmosphere with 5 to 8% $CO_2$ in T-cell medium (RPMI 1640 with 2-10% heat-inactivated (30 min., 56° C.) human AB serum, 2 mM glutamine and 100 mg/ml kanamycin or gentamycin (all components from Pan-Systems, Aidenbach, Germany). The incubation can be performed in absence or presence of suitable (co)-stimulatory substances, like for example cytokines, mitogens or antibodies. Alternatively, the T-cell-containing cell populations can also be derived from patients/test persons with compatible MHC-pattern. If reactive T-cells, which recognise APC being transduced with the gene transfer vectors and which present specific T-cell epitopes, are present in the mixed APC/T-cell culture, these induce or inhibit the marker expression of the sub-populations of the APC according to the invention. If APC according to the invention, which present T-cell epitopes being recognised by the reactive T-cells of the test person/patient, are present in the mixed APC/T-cell culture, the marker gene expression is induced or inhibited as a result of the epitope-specific recognition in these APC.

In the further method, the measurably changed (increased or induced) expression of the polypeptides being under the control of the genomic controllable promoter in the APC serves in step (d) as a marker for the T-cell recognition, wherein the change is a result of the epitope-specific recognition of the APC according to the invention by a T-cell.

For example, the increased expression of the OX40 ligand (OX40L) and of the 4-1 BB ligand (4-1 BBL) (den Haan and Bevan, 2000) as well as of the co-stimulatory proteins B7.1 (CD80), B7.2 (CD86) and of the Fas ligand (FasL) as a result of the epitope-specific recognition in the APC may serve as markers. In addition, the expression of any polypeptide which is measurably increased or decreased in APC according to the invention as a result of the epitope-specific recognition of the APC according to the invention by a reactive T-cell, is suited as a marker.

The presence and the number of marker-positive APC can for example be detected by means of FACS, ELISA or the immuno-fluorescence technology using specific chemically modified antibodies and pairs of antibodies, respectively. Alternatively, markers with enzymatic functions are detected by the addition and reaction of a suitable substrate. Epitope-presenting APC according to the invention which show expression of one of the described markers can be detected, isolated and individualised by means of different immunological and biochemical methods using commercially available devices and test systems. Thus, the expression of selected markers can be detected for example by means of FACS, ELISA or immuno-fluorescence technology, for example using specific, chemically modified antibodies and pairs of antibodies, respectively. Alternatively, markers with enzymatic functions are detected by the addition and reaction of suitable substrates. The isolation and individualisation of marker-positive APC can be performed using the FACSsort technology (for example by the companies Coulter, Becton Dickinson). The molecular biological and immunological methods which are used in the search for epitopes, e.g. the performance of FACSscan analyses, FACSsorting, ELISA assays, immuno-fluorescence analyses, detection of enzymatic reactions, the preparation of total DNA from cells, the PCR as well as sequencing of nucleic acid are state of the art.

The isolation and characterisation of the polynucleotide encoding the target epitopes of reactive T-cells from selected marker-positive APC according to the invention can be performed by means of different methods which are described exemplarily in the following. For example, the PCR-method is suited for the identification of the target epitopes of reactive T-cells from the selected, marker-positive APC according to the invention. Total-DNA is prepared from the individualised marker-positive APC according to the invention using a commercial kit (for example of the companies Stratagene or Qiagen) and the unknown nucleic acid sequence of the searched T-cell epitope is amplified using suitable oligonucleotides (primers) by the PCR-method. The primers preferentially exhibit constant regions within the nucleic acids according to the invention being located in direct proximity to the identified polynucleotides.

Alternatively, the lysate of the selected and individualised marker-positive APC can be used as a template for the PCR-reaction, too. By using specific primers outside of the polynucleotides which are under the control of the constitutive promoter ($P_2$) in the flanking regions on the non-viral and viral vectors according to the invention, the unknown cDNAs being under the control of the constitutive promoter may be amplified, characterised by sequencing and potentially identified by the comparison with sequences of a database.

Alternatively, total-DNA can be prepared from the individualised, marker-positive APC or from a mixture of marker-positive APC using e.g. a commercial kit. Subsequently, the obtained DNA is cleaved with a restriction endonuclease which recognition sequence flanks the constitutive promoter including the polynucleotide being under its control as well as a bacterial resistance and the bacterial origin of replication in the 5' and 3' region (see FIG. 1B). Subsequently, the obtained DNA fragments are re-ligated and transformed in suitable bacteria, for example DH10B bacteria. If episomal plasmids were used as transfer systems according to the invention for the transduction of the APC the total DNA obtained from the marker-positive APC can be used directly for transformation of suitable bacteria.

Bacteria, which were transformed according to this method with plasmids which contain the promoter $P_2$ according to the invention and the polynucleotide being under the control of this promoter in combination with a bacterial antibiotic resistance and the bacterial origin of a replication, can be selectively cultivated and individualised by spreading on agar plates which contain the respective antibiotic. After cultivation of the clonal bacterial colonies in a respective antibiotic-containing selective medium the plasmid DNA is obtained from the bacteria by means of common methods, for example by alkaline lysis.

The plasmids that have been purified from the bacteria are directly used as templates for the sequencing reaction. By the use of specific primers that bind to the conserved regions of the vector according to the invention close-by the polynucleotide to be identified which is under the control of the promoter $P_2$ according to the invention, the polynucleotides being under the control of the promoter $P_2$ can be determined by sequencing, and their identity can be potentially determined by comparison with sequences in biological and medical databases. For the confirmation of the cDNA-sequences identified by these methods and for the elimination of false positive results, the obtained nucleic acid sequences are re-cloned under the control of the constitutive promoter into the vectors according to the invention and transfected by means of one of the transfer systems according to the invention in APC. The APC generated this way are then re-tested for recognition by reactive T-cells of the same patient. By means of a progressive 5'- and 3'-truncation of the identified polynucleotides and the insertion of these polynucleotides by means of transfer systems according to the invention into APC the minimal length of the recognised target region can be determined by co-cultivation experiments with reactive T-cells of the patient/test person.

By means of the method according to the invention, for example polypeptides and epitopes can be identified which are important in the T-cell mediated recognition and control of diseases which are induced by micro-organisms and parasites, in the T-cell mediated recognition and control of tumour diseases, and which represent target structures of misguided, endogenous T-cells in the case of auto-immune diseases and chronic inflammatory processes or that represent target structures of endogenous T-cells in the case of the rejection of transplanted tissues or organs.

The methods according to the invention are suited for a multiplicity of different medical applications. By means of the method according to the invention, epitope- and polypeptide-specific T-cells can be identified for the early diagnostics of auto-immune diseases; for monitoring of reactive T-cells in patients with auto-immune diseases, which show a chronic progressive or relapsing/remitting course of disease; for determination of the efficiency of therapeutic treatments of diseases with T-cells being involved; for screening of the security and efficiency of medicaments that elicit a deletion or anergy of T-cells or cause a general immune suppression; for monitoring of the efficiency of therapeutic and prophylactic vaccinations for the induction of T-cells; for monitoring and diagnostics of micro-organism- and parasite-induced diseases with T-cells being involved; for monitoring and diagnostics of chronic inflammations with T-cells being involved; for monitoring and diagnostics of tumour antigen-specific T-cells; for monitoring and diagnostics of T-cells that play a role in the rejection of transplants or for the targeted selection of test persons for studies in vaccinations and the testing of therapeutic treatments.

Furthermore, the invention comprises a kit for a diagnostic detection of auto-reactive T-cells, comprising suitable vectors or transfer systems according to the invention for the generation of APC according to the invention, packed in suitable containers; comprising a detailed instruction for the performance of the diagnostic detection and a suitable container for transport and storage of the kit according to the invention.

The present invention results in the following advantages for the search for epitopes. The use of the vectors according to the invention in combination with gene libraries facilitates the quick identification of T-cell epitopes from presently known and characterised polypeptides but also from presently not yet described and characterised, respectively, polypeptides. In addition, the use of gene libraries in one or a very limited number of experimental approaches many target epitopes of reactive T-cells of a test person/patient can be isolated and described simultaneously. Therefore, this method in comparison to the as yet used methods for the search for epitopes accounts for a significantly reduced expense of time and costs.

Poly-specific T-cells of a patient may be used for the search for epitopes, thereby avoiding the very time and labour consuming step for the generation of T-cell lines. APC expressing their target epitopes of reactive T-cells can be selected very quickly because of the marker expression by commercially available devices (for example FACSsort) and the genes of the searched T-cell epitopes may be identified by means of molecular biological routine methods.

The method according to the invention is universally suited for the search for epitopes in different test persons/patients. Gene transfer means carrying the vectors according to the invention can be used universally for the genetic manipulation of the APC for the search for epitopes independently of the haplotype in all test persons/patients. The method according to the invention is suited for the search for target epitopes of different T-cell populations (especially of $CD4^+$ T-helper cells but also of $CD8^+$ cytotoxic T-cells, $CD161^+$NKT-cells and $CD4^+CD25^+$ regulatory T-cells).

The present invention results in the following advantages in the case of the detection and diagnostics of epitope-specific T-cells. An essential advantages of the method according to the invention resides in the fact that the method is based on the measurement of a marker gene expression which is induced by an epitope-specific recognition by a T-cell in APC and that is not based, like in the case of all previous methods, on the measurement of reactions of the T-cell resulting from a recognition of the epitope on the APC. Thus, the sensitivity of the assay system is considerably increased. The method of detection for the reactive T-cells is in comparison to the common methods of diagnostics (CTL-assay, ELISPOT, cytokin-ELISA, proliferation assay) all-purpose, easier to manage, significantly more cost-effective, less time consuming and sensitive. The presence and number of reactive T-cells can easily be detected and quantified by means of commercially available and in many diagnostics laboratories routinely used devices (FACS). The method for diagnostics according to the invention can be universally used independently of the haplotype of the test person/patient for the detection of the reactive T-cells. The method according to the invention is suited for the detection of various epitope-specific T-cell populations (especially $CD4^+$ T-helper cells but also $CD8^+$ cytotoxic T-cells, $CD161^+$ NKT-cells and $CD4^+CD25^+$ regulatory T-cells).

The following examples illustrate the present invention:

EXAMPLE 1

Cloning of the Vector Backbone According to the Invention for the Expression of Polypeptides Under the Control of a Promoter which is Constitutively Active in APC ($P_2$)

As starting vectors for the cloning of the vector backbones according to the invention served the plasmid pcDNA3.1(+) (Invitrogen) containing 5446 base pairs (bp) as well as the vector pcDNA3.1(+)dNeo which was generated by the deletion of a 1905 bp-comprising DNA-fragment including the coding region for neomycin (bp 1289-3194) from the plasmid pcDNA3.1(+). Therefore the nucleic acid sequence of the pcDNA3.1(+)dNeo-plasmid was obtained by means of the polymerase chain reaction (PCR) using the following conditions for amplification: introductory denaturation step: 95° C., 1 min., followed by a 3-step PCR (35 cycles) with the following conditions: denaturation: 94° C., 1 min., annealing 55° C., 1 min., elongation: 72° C., 3.5 min. with a final polymerisation step at 72° C. for 10 min. with subsequent permanent cooling at 4° C. For the amplification the primers P1 (5'-GCTGGTTCTTTCCGCCTCAGAAGC-3'; SEQ ID NO: 6) and P2 (5'-CACTGCATTCTAGTTGTGGTTTG-3'; SEQ ID NO: 7) were used. The obtained PCR-product was purified by means of a QIAquick PCR Purification Kit (Qiagen) following the manufacturer's protocol, phosphorylated and finally re-ligated. The obtained plasmid comprising 3541 bp was denoted pcDNA3.1(+)dNeo.

For the insertion of different control sequences being constitutively active in APC, these sequences were amplified by PCR from suitable material (chromosomal DNA of human and murine origin) and inserted into the vector backbones pcDNA3.1(+) and pcDNA3.1(+)dNeo by means of suitable restriction sites.

Amplification of the Murine PGK Promoter

The 621 bp comprising sequence of the murine PGK promoter was obtained by PCR from isolated chromosomal DNA of the murine cell line C2C12 (ATCC number CRL-1772) using the following conditions: introductory denaturation step: 95° C., 2 min., followed by a 3-step PCR (35 cycles) with the following conditions: denaturation: 95° C., 45 sec., annealing 66° C., 1 min., elongation: 72° C., 1.5 min., with a final polymerisation step at 72° C. for 10 min. with final permanent cooling at 4° C. For the amplification the primers P3 (5' primer: 5'-GCAGGCTCGCGACTACCGGGTAGGG-GAGGCGC-3'; SEQ ID NO: 8) and P4 (3' primer: 5'-GCAG-GCGGATCCACGCGCTTCTACAAGGCGCTTGC-3'; SEQ ID NO: 9) were used.

Amplification of the Human PKG Promoter

The 531 bp comprising sequence of the human PGK promoter was isolated via PCR from isolated chromosomal DNA from human PBMCs using the following conditions for amplification: introductory denaturation step: 98° C., 2 min., followed by two subsequent 3-step PCRs with the following conditions: first round of PCR-amplification (15 cycles): denaturation: 95° C., 1 min., annealing 58° C., 1 min., elongation: 72° C., 1.5 min. Subsequently a second round of PCR-amplification followed (25 cycles) with the following conditions: denaturation: 95° C., 1 min., annealing 69° C., 1 min., elongation: 72° C., 1.5 min. with a final polymerisation step at 72° C. for 10 min. with subsequent permanent cooling at 4° C. For the amplification the primers P5 (5' primer: 5'-GCAGGCTCGCGACGGGGTTGGGGTTGCGCC-3'; SEQ ID NO: 10) and P6 (3' primer: 5'-GCAGGCGGATC-CTTTGGAAATACAGCTGGGGAG-3'; SEQ ID NO: 11) were used.

Amplification of the Human DHFR Promoter

The 479 bp comprising sequence of the human dihydrofolate-reductase (DHFR) promoter was obtained via PCR from isolated chromosomal DNA derived from human PBMCs using the following conditions for amplification: introductory denaturation step: 95° C., 2 min., subsequently followed by a 3-step PCR (30 cycles) with the following conditions: denaturation: 95° C., 45 sec., annealing 71° C., 1 min., elongation: 72° C., 1.5 min., with a final polymerisation step 72° C. for 10 min. with a subsequent permanent cooling at 4° C. For the amplification the primers P7 (5' primer: 5'-GCAGGCTCGCGACGATGGCCCTGCCCAGTCCC-3'; SEQ ID NO: 12) and P8 (3' primer: 5'-GCAGGCGGATC-CGACAGCAGCGGGAGGACCTC-3'; SEQ ID NO: 13) were used.

Amplification of Human EF-1α Promoter

Hereby the 1244 bp comprising sequence of the human EF-1α promoter was obtained by PCR from isolated chromosomal DNA derived from human PBMCs using the following conditions for amplification: introductory denaturation step: 98° C., 2 min., followed by two subsequent 3-step PCRs with the following conditions: first round of PCR-amplification (15 cycles) denaturation: 95° C., 1 min., annealing 58° C., 1 min., elongation: 72° C., 10 min. Subsequently a second round of PCR-amplification followed (30 cycles) with the following conditions: denaturation: 98° C., 1 min., annealing 67° C., 1 min., elongation: 72° C., 2 min. with a final polymerisation step at 72° C. for 10 min. with subsequent permanent cooling at 4° C. For the amplification the primers P9 (5' primer: 5'-GCAGGCTCGCGAGGCTCCGGTGCCCGT-CAGTG-3'; SEQ ID NO: 14) and P10 (3' primer: 5'-GCAG-GCGGATCCACCTAGCCAGCTTGGGTCTCC-3'; SEQ ID NO: 15) were used.

Amplification of the Human Ubiquitin C (UbC) Promoter

The 1210 bp comprising sequence of the human UbC promoter was amplified by PCR from isolated chromosomal DNA derived from human PBMCs using the following conditions: introductory denaturation step: 98° C., 2 min., followed by two subsequent 3-step PCRs with the following conditions: first round of PCR-amplification (15 cycles) denaturation: 95° C., 50 sec., annealing 58° C., 45 sec., elongation: 72° C., 3 min. Subsequently a second round of PCR-amplification followed (25 cycles) with the following conditions: denaturation: 95° C., 50 sec., annealing 71° C., 45 sec., elongation: 72° C., 3 min., with a final polymerisation step at 72° C. for 10 min. with a subsequent permanent cooling at 4° C. For the amplification the primers P11 (5' primer: 5'-GCAGGCTCGCGAGGCCTCCGCGCCGGGTTTTGG-3'; SEQ ID NO: 16) and P12 (3' primer: 5'-GCAGGCG-GATCCGTCTAACAAAAAAGCCAAAAACG-3'; SEQ ID NO: 17) were used.

Amplification of the Human ICI Promoter

The 569 bp comprising sequence of the human ICI promoter was amplified by PCR from isolated chromosomal DNA derived from human PBMCs using the following conditions: introductory denaturation step: 95° C., 2 min., followed by two subsequent 3-step PCRs with the following conditions: first round of PCR-amplification (15 cycles): denaturation: 95° C., 45 sec., annealing 58° C., 1 min., elongation: 72° C., 1.5 min. Subsequently followed a second round of PCR-amplification (25 cycles) with the following conditions: denaturation: 95° C., 45 sec., annealing 66° C., 1 min., elongation: 72° C., 1.5 min. with a final polymerisation step at 72° C. for 10 min. with subsequent permanent cooling at 4° C. For the amplification the primers P13 (5' primer: 5'-GCAGGCTCGCGAGCTGTAATTTCTAATCTAAACC-3'; SEQ ID NO: 18) and P14 (3' primer: 5'-GCAGGCG-GATCCAGCAGCAGAGTGCGGCAACAC-3'; SEQ ID NO: 19) were used.

The restriction sites (NruI in the 5' primer and BamHI in the 3' primer), which are present in the primers being used for amplification of the above mentioned promoters, are each depicted in italics.

The preparation of human PBMC was performed as described in the following: freshly extracted whole blood of a healthy test person was spiked with 20 IU/ml heparin. 50 ml-Leukosep-vials with a separating membrane were filled with 15 ml Ficoll-Histopaque (Sigma, Deisenhofen, Germany) and centrifuged for 2 min. at 500×g. The tubes were filled with the heparinised whole blood and diluted 1:1 with sterile PBS/0.5% BSA. The samples were centrifuged for 30-40 min. at 400×g without deceleration of the rotor at the end of the centrifugation. The lymphocytes-containing, turbid interface was carefully removed and washed in 3 volumes of T-cell medium (RPMI 1640 medium with 10% heat inactivated (30 min. at 56° C.) human AB serum, 2 mM glutamine and 100 mg/ml kanamycin and gentamycin, respectively (all components from PanSystems, Aidenbach, Germany)) for three times.

The isolation of genomic DNA from human PBMC or murine C2C12 muscle cells was performed with the "DNA extraction kit" (Stratagene) following the manufacturer's protocol. For this the cells were washed 2× with cold PBS (phosphate buffered saline) and the cell number was determined. $1 \times 10^8$ cells each were transferred to 15 ml plastic tubes and put on ice immediately. All subsequent working steps were performed on ice, too. After a centrifugation for 15 minutes (350×g, 4° C.) the cells were re-suspended in 11 ml solution 2 (50 mM Tris/HCl, pH 8.0, 20 mM EDTA, 2% SDS) and homogenised with a Dounce homogeniser. After this Pronase (Stratagene) was added to a final concentration of 100 µg/ml and the sample was incubated overnight at 37° C., slightly shaking. Subsequently, the sample was cooled on ice for 10 min. and 4 ml of an ice-cold solution 3 (saturated NaCl-solution) were added. After short mixing of the solutions a further incubation on ice took place for 5 min. and the pellet was centrifuged at 4° C. (15 min., 2000×g). After this, the supernatant was transferred into a sterile 50 ml centrifugation tube by a cut plastic pipette, RNAse was added to a final concentration of 20 µg/ml and the mixture was incubated for 15 min. at 37° C. After addition of two volumes of 100% ethanol and slight shaking the precipitation of the genomic DNA in a white smear could be visualised. The DNA could now be either wound up on a glass rod or be pelleted by a centrifugation for 15 minutes at 4° C. and 2000×g. After a washing step with 2 ml of cold 70% ethanol the DNA was transferred to an Eppendorf reaction tube, centrifuged and air-dried for 15 min. at room temperature. The DNA pellet was re-suspended in $H_2O_{bid.}$ and dissolved overnight at room temperature and for 1-2 hours at 55° C., respectively. The determination of the DNA concentration was performed photometrically at 258 mn.

The obtained PCR-products were purified by means of a QIAquick PCR purification kit (Qiagen) following the manufacturer's protocol and subsequently 20 µg of the respective purified PCR-bands were digested in 100 µl with the restriction enzymes NruI and BamHI. At the same time 20 µg each of the vector backbones pcDNA3.1(+) and pcDNA3.1(+)dNeo were digested with the same restriction enzymes (NruI and BamHI). The obtained restriction products were separated by a 1% agarose gel, the polynucleotides for the linearised vector backbones and the different promoters were cut out of the gel and the nucleic acids were purified by means of a QIAquick gel extraction kit (Qiagen). Subsequently, the obtained polynucleotides of the vector backbones were ligated with the different digested PCR-amplificates with the respective promoter sequences overnight at 16° C., and the ligation samples were subsequently transformed into bacteria (DH5α). After an incubation for 1 hour at 37° C. in LB medium without a selection antibiotic the transformed bacteria were spread on $LB_{Amp}$ plates and incubated overnight at 37° C. The obtained bacterial colonies were then cultivated in $LB_{Amp}$ medium, the bacterial plasmid-DNA was isolated by the technique of the alkaline lysis and characterised by a restriction digest using the restriction endonucleases BglII/EcoRI. The vectors generated this way were denoted pcDNA3.1(+)mPGK, pcDNA3.1(+)hPGK, pcDNA3.1(+)hDHFR, pcDNA3.1(+)hEF-1α, pcDNA3.1(+)hUbC, pcDNA3.1(+)hICI, and pcDNA3.1(+)dNeomPGK, pcDNA3.1(+)dNeohPGK, pcDNA3.1(+)dNeohDHFR, pcDNA3.1(+)dNeohEF-1α, pcDNA3.1(+)dNeohUbC and pcDNA3.1(+)dNeohICI, respectively.

The 224 bp comprising bovine growth hormone (BGH) polyadenylation sequence was amplified from the pcDNA3.1(+)-vector by PCR using suitable PCR conditions (introductory denaturation step: 95° C., 2 min., subsequent a 3-step PCR (35 cycles) with the following conditions: denaturation: 95° C., 30 sec.; annealing 55° C., 1 min.; elongation: 72° C., 1 min., and a final polymerisation step at 72° C. for 10 min. with a subsequent permanent cooling at 4° C.). For amplification the primer P15 (5' primer: 5'-GGCGGGGGATCCCT-GTGCCTTCTAGTTGCC-3'; SEQ ID NO: 20) and P16 (3' primer: 5'-GGCGGGAGATCTCCATAGAGCCCACCGC-3'; SEQ ID NO: 21) were used. The restriction sites contained within the primers (BamHI in the 5' primer; BglII in the 3' primer) are depicted in italics. The PCR-amplified band was subsequently purified as described previously, restricted with the restriction enzymes BglII and BamHI and the in such a way obtained band was ligated into the BamHI-linearised plasmids pcDNA3.1(+)mPGK, pcDNA3.1(+)hPGK, pcDNA3.1(+)hDHFR, pcDNA3.1(+)hEF-1α, pcDNA3.1(+)hUbC, pcDNA3.1(+)hICI, and pcDNA3.1(+)dNeomPGK, pcDNA3.1(+)dNeohPGK, pcDNA3.1(+)dNeohDHFR, pcDNA3.1(+)dNeohEF-1α, pcDNA3.1(+)dNeohUbC, respectively, and pcDNA3.1(+)dNeohICI. The in such a way generated vectors received the denotations pcDNA3.1(+)mPGKPA, pcDNA3.1(+)hPGKPA, pcDNA3.1(+)hDHFRPA, pcDNA3.1(+)hEF-1αPA, pcDNA3.1(+)hUbCPA, pcDNA3.1(+)hICIPA, and pcDNA3.1(+)dNeomPGKPA, pcDNA3.1(+)dNeohPGKPA, pcDNA3.1(+)dNeohDHFRPA, pcDNA3.1(+)dNeohEF-1αPA, pcDNA3.1(+)dNeohUbCPA, respectively, and pcDNA3.1(+)dNeohICIPA.

However, the vector backbones pcDNA3.1(+) (Invitrogen) as well as the vector pcDNA3.1(+)dNeo are analogously suited as vectors for the expression of any polypeptides in APC. They contain the CMV promoter being constitutively active in APC in connection with the bovine growth hormone (BGH) polyadenylation sequence.

Subsequently, polynucleotides encoding polypeptides like for example the Epstein-Barr virus BZLF-1 protein, the human myelin basic protein (MBP) and the HIV-1 p24 capsid protein, were cloned under the control of the above mentioned promoter being constitutively active in APC. For this the desired polynucleotides were amplified by PCR, the PCR-amplificates purified, restricted with suitable restriction endonucleases and inserted into vectors which have been digested with the respective restriction endonucleases.

Generation of Plasmids for the Constitutive Expression of the Epstein-Barr Virus BZLF-1 Protein The cDNA for the EBV BZLF-1 protein was amplified from viral DNA of the EBV strain B95-8 from total DNA of infected marmoset cells by means of PCR using suitable PCR conditions (introductory denaturation step: 95° C., 2 min., subsequently followed by a 3-step PCR (15 cycles) with the following conditions: denaturation: 95° C., 30 sec.; annealing 52° C., 1 min.; elongation: 72° C., 2 min., after this another PCR (25 cycles) took place with the following conditions: denaturation: 95° C., 30 sec.; annealing 63° C., 1 min.; elongation: 72° C., 2 min. and a final polymerisation step at 72° C. for 10 min. with subsequent permanent cooling at 4° C.). In the case of the PCR-reaction for the amplification of the BZLF-1 cDNA 2.5% DMSO were added to the PCR sample. For amplification the primers P17 (5' primer: 5'-GGCG-GAGATCTTTAGAAATTTAAGAGATCC-3'; SEQ ID NO: 22) and P18 (3' primer: 5'-GGCGGGAGATCTATGATG-GACCCAAACTCG-3'; SEQ ID NO: 23) were used. The amplified 970 nucleotides comprising band which was amplified by PCR was purified as described previously, restricted with the restriction enzyme BglII and the obtained band was ligated into the BamHI-linearised expression vectors pcDNA3.1(+)mPGKPA, pcDNA3.1(+)hPGKPA, pcDNA3.1 (+)hDHFRPA, pcDNA3.1(+)hEF-1αPA, pcDNA3.1(+hUb-CPA, pcDNA3.1(+)hICIPA, respectively into pcDNA3.1(+) dNeomPGKPA, pcDNA3.1(+)dNeohPGKPA, pcDNA3.1(+) dNeohDHFRPA, pcDNA3.1(+)dNeohEF-1αPA, pcDNA3.1 (+)dNeohUbCPA, pcDNA3.1(+)dNeohICIPA, pcDNA3.1 (+) and into pcDNA3.1(+)dNeo. The expression vectors generated this way obtained the denotation pcDNA3.1(+) mPGKPA-Z, pcDNA3.1(+)hPGKPA-Z, pcDNA3.1(+)hDH-FRPA-Z, pcDNA3.1(+)hEF-1αPA-Z, pcDNA3.1(+)hUb-CPA-Z, pcDNA3.1(+)hICIPA-Z, respectively pcDNA3.1(+) dNeomPGKPA-Z, pcDNA3.1(+)dNeohPGKPA-Z, pcDNA3.1(+)dNeohDHFRPA-Z, pcDNA3.1(+)dNeohEF-1αPA-Z, pcDNA3.1(+)dNeohUbCPA-Z, pcDNA3.1(+) dNeohICIPA-Z, pcDNA3.1(+)-Z (FIG. 2) and pcDNA3.1(+) dNeo-Z.

Generation of Plasmids for the Constitutive Expression of the Human MBP-Protein

The cDNA for the human MBP-protein was amplified from total DNA from brain cells by means of PCR using suitable conditions (introductory denaturation step: 95° C., 2 min., subsequently followed by a 3-step PCR (35 cycles) with the following conditions: denaturation: 95° C., 30 sec.; annealing 55° C., 1 min.; elongation: 72° C., 2 min. and the final polymerisation step at 72° C. for 10 min. with subsequent permanent cooling at 4° C.). For amplification the primers P19 (5' primer: 5'-GGCGGAGATCTATGGCGTCACAGAA-GAGACC-3'; SEQ ID NO: 24) and P20 (3' primer: 5'-GGCGGGAGATCTTCAGCGTCTAGCCATGGG-3'; SEQ ID NO: 25) were used. The 585 nucleotides comprising band which was amplified by PCR was then purified as described previously, restricted with the restriction enzyme BglII and the obtained band was ligated into the BamHI-linearised plasmids pcDNA3.1(+)mPGKPA, pcDNA3.1(+) hPGKPA, pcDNA3.1(+)hDHFRPA, pcDNA3.1(+)hEF-1αPA, pcDNA3.1(+)hUbCPA, pcDNA3.1(+)hICIPA, respectively into pcDNA3.1(+)dNeomPGKPA, pcDNA3.1 (+)dNeohPGKPA, pcDNA3.1(+)dNeohDHFRPA, pcDNA3.1(+)dNeohEF-1αPA, pcDNA3.1(+)dNeohUbCPA, pcDNA3.1(+)dNeohICIPA, pcDNA3.1(+) and pcDNA3.1(+) dNeo. The expression vectors generated this way obtained the denotations pcDNA3.1(+)mPGKPA-MBP, pcDNA3.1(+) hPGKPA-MBP, pcDNA3.1(+)hDHFRPA-MBP, pcDNA3.1 (+)hEF-1αPA-MBP, pcDNA3.1(+)hUbCPA-MBP, pcDNA3.1(+)hICIPA-MBP, respectively pcDNA3.1(+) dNeomPGKPA-MBP, pcDNA3.1(+)dNeohPGKPA-MBP, pcDNA3.1(+)dNeohDHFRPA-MBP, pcDNA3.1(+)dNeo-hEF-1αPA-MBP, pcDNA3.1(+)dNeohUbCPA-MBP, pcDNA3.1(+)dNeohICIPA-MBP, pcDNA3.1(+)-MBP and pcDNA3.1(+)dNeo-MBP.

A codon-optimised DNA for the HIV-1 p24 capsid protein was amplified from a synthetically produced nucleic acid according to a published HIV-1 gag sequence (Graf et al. (2000), J. Virol. 74:10822) by means of PCR using suitable conditions (introductory denaturation step: 95° C., 2 min., subsequently followed by a 3-step PCR (30 cycles) with the following conditions: denaturation: 95° C., 45 sec.; annealing 66° C., 1 min.; elongation: 72° C., 2 min. and a final polymerisation step at 72° C. for 10 min. with subsequent permanent cooling at 4° C.). Codon-optimised genes can be obtained from several companies (for example GeneArt, Regensburg, Germany; Entelechon, Regensburg, Germany). For amplification the primers P21 (5' primer: 5'-GGCG-GTCTAGAGCCGCCACCATGCCCATCGTG-3'; SEQ ID NO: 26) and P22 (3' primer: 5'-GGCGGGGAATTCTCA-CAGCAGCCTGGCCTTGTG-3'; SEQ ID NO: 27) were used. The obtained PCR product was subsequently purified as described previously, restricted with the restriction enzyme BglII and the obtained band was ligated into the BamHI-linearised plasmids pcDNA3.1(+)mPGKPA, pcDNA3.1(+) hPGKPA, pcDNA3.1(+)hDHFRPA, pcDNA3.1(+)hEF-1αPA, pcDNA3.1(+)hUbCPA, pcDNA3.1(+)hICIPA, respectively pcDNA3.1(+)dNeomPGKPA, pcDNA3.1(+) dNeohPGKPA, pcDNA3.1(+)dNeohDHFRPA, pcDNA3.1 (+)dNeohEF-1αPA, pcDNA3.1(+)dNeohUbCPA, pcDNA3.1(+)dNeohICIPA, pcDNA3.1(+) and pcDNA3.1(+) dNeo. The expression vectors generated this way obtained the denotations pcDNA3.1(+)mPGKPA-p24, pcDNA3.1(+) hPGKPA-p24, pcDNA3.1(+)hDHFRPA-p24, pcDNA3.1(+) hEF-1αPA-p24, pcDNA3.1(+)hUbCPA-p24, pcDNA3.1(+) hICIPA-p24, respectively pcDNA3.1(+)dNeomPGKPA-p24, pcDNA3.1 (+)dNeohPGKPA-p24, pcDNA3.1(+)dNeohDH-FRPA-p24, pcDNA3.1(+)dNeohEF-1αPA-p24, pcDNA3.1 (+)dNeohUbCPA-p24, pcDNA3.1(+)dNeohICIPA-p24, pcDNA3.1(+)-p24 and pcDNA3.1(+)dNeo-p24.

Generation of Plasmids for the Constitutive Expression of the "Enhanced Green Fluorescent Protein" (eGFP)

The gene for the "enhanced green fluorescent protein" (eGFP) was amplified from the plasmid pRC/CMV-EGFP (Vogel et al., 1998, BioTechniques 143, 1967-1983) by means of PCR using suitable PCR conditions (introductory denaturation step: 95° C., 2 min., subsequently a 3-step PCR (35 cycles) with the following conditions: denaturation: 95° C., 30 sec.; annealing 55° C., 1 min.; elongation: 72° C., 2 min. and a final polymerisation step at 72° C. for 10 min. with subsequent permanent cooling at 4° C. For amplification the primers P23 (5' primer: 5'-GGCGGGAGATCTCGCCAC-CATGGTGAGCAAGG-3'; SEQ ID NO: 28) and P24 (3' primer: 5'-GGCGGGAGATCTTTACTTGTA-CAGCTCGTCC-3'; SEQ ID NO: 29) were used. The PCR-amplified specific band having the size of 752 bp was subsequently purified as described previously, restricted with the restriction enzyme BglII, and the obtained band was ligated into the BamHI-linearised expression vectors pcDNA3.1(+) mpGKPA, pcDNA3.1(+)hPGKPA, pcDNA3.1(+)hDH-FRPA, pcDNA3.1(+)hEF-1αPA, pcDNA3.1(+)hUbCPA, pcDNA3.1(+)hICIPA, respectively pcDNA3.1(+)

dNeomPGKPA, pcDNA3.1(+)dNeohPGKPA, pcDNA3.1(+)dNeohDHFRPA, pcDNA3.1(+)dNeohEF-1αPA, pcDNA3.1(+)dNeohUbCPA, pcDNA3.1(+)dNeohICIPA, pcDNA3.1(+) and into pcDNA3.1(+)dNeo. The expression vectors generated this way obtained the denotations pcDNA3.1(+) mPGKPA-eGFP, pcDNA3.1(+)hPGKPA-eGFP, pcDNA3.1(+)hDHFRPA-eGFP, pcDNA3.1(+)hEF-1αPA-eGFP, pcDNA3.1(+)hUbCPA-eGFP, pcDNA3.1(+)hICIPA-eGFP, respectively pcDNA3.1(+)dNeomPGKPA-eGFP, pcDNA3.1(+)dNeohPGKPA-eGFP, pcDNA3.1(+)dNeohDHFRPA-eGFP, pcDNA3.1(+)dNeohEF-1αPA-eGFP, pcDNA3.1(+)dNeohUbCPA-eGFP, pcDNA3.1(+)dNeohICIPA-eGFP, pcDNA3.1(+)-eGFP and pcDNA3.1(+)dNeo-eGFP.

EXAMPLE 2

Generation of Vectors which Facilitate a Targeted Transport of the Polypeptides Being Expressed by Means of the Constitutive Promoter ($P_2$) into the Endolysosome For the enhancement of the endo/lysosomal degradation of the polypeptides being expressed by the means of the constitutive promoter ($P_2$), additionally different lysosomal targeting signals, for example the cytoplasmatic region of the Ii chain, or regions of the "invariant chain", or of LAMP-1, LAMP-2, LIMP-1 (CD63), LAP or MHC-class II proteins were introduced into the plasmids pcDNA3.1(+)mPGKPA, pcDNA3.1(+)hPGKPA, pcDNA3.1(+)hDHFRPA, pcDNA3.1(+)hEF-1αPA, pcDNA3.1(+)hUbCPA, pcDNA3.1(+)hICIPA, respectively into pcDNA3.1(+)dNeomPGKPA, pcDNA3.1(+)dNeohPGKPA, pcDNA3.1(+)dNeohDHFRPA, pcDNA3.1(+)dNeohEF-1αPA, pcDNA3.1(+)dNeohUbCPA, pcDNA3.1(+)dNeohICIPA, pcDNA3.1(+) and into pcDNA3.1(+)dNeo.

Construction of Expression Vectors which Express Chimeric Proteins of Signalling Peptide/Polypeptide/LAMP-1

The cloning of chimeric polypeptides being composed of the N-terminal signalling peptide of the human LAMP-1 protein, any arbitrary polypeptide, for example the EBV BZLF-1 protein or the human MBP protein as well as the transmembrane domain and the cytoplasmatic part of LAMP-1 was performed sequentially using the compatible restriction sites BamHI and BglII.

The nucleic acid sequence encoding the signalling peptide of LAMP-1 was amplified from isolated chromosomal DNA derived from human PBMCs by means of PCR using a high fidelity Pfu polymerase (Stratagene) and the following conditions: introductory denaturation step: 95° C., 2 min., subsequently followed by a 3-step PCR (35 cycles) with the following conditions: denaturation: 95° C., 1 min.; annealing 60° C., 1 min.; elongation: 72° C., 1 min.; final polymerisation step at 72° C. for 10 min. with subsequent permanent cooling at 4° C. For amplification the primers P25 (5' primer: 5'-GCAGGAGATCTTATGGCGCCCCGC-3'; SEQ ID NO: 30) and P26 (3' primer: 5'-GCAGGCGGATCCTCAAAGAGTGCTGA-3'; SEQ ID NO: 31) were used.

The Amplification of Polynucleotides Encoding the BZLF-1 and MBP Proteins Using the Amplification Conditions which were Described Previously For amplification of the BZLF-1 gene the primers P27 (5' primer: 5'-GGCGGGGATCCTTAGAAATTTAA-GAGATCC-3'; SEQ ID NO: 32) and primer P28 (3' Primer: 5'-GGCGGGAGATCTATGATGGACCCAAACTCG-3'; SEQ ID NO: 33) were used.

For amplification of the human MBP protein the primers P29 (5' primer: 5'-GGCGGAGATCTATGGCGTCACA-GAAGAGACC-3'; SEQ ID NO: 34) and P30 (3' primer: 5'-GGCGGGGGATCCTCAGCGTCTAGCCATGGG-3'; SEQ ID NO: 35) were used.

The amplification of the transmembrane region and cytoplasmatic domain of LAMP-1 was performed by means of PCR using a high fidelity Pfu polymerase (Stratagene) from isolated chromosomal DNA derived from human PBMCs using the following conditions: introductory denaturation step: 95° C., 2 min., subsequently followed by a 3-step PCR (35 cycles) with the following conditions: denaturation: 95° C., 1 min.; annealing 60° C., 1 min.; elongation: 72° C., 1.5 min., final polymerisation step at 72° C. for 10 min. with subsequent permanent cooling at 4° C. For amplification the primers P31 (5' primer: 5'-GCAGGAGATCTAACAG-CACGCTGATC-3'; SEQ ID NO: 36) and P32 (3' primer: 5'-GCAGGCAGATCTCTAGATAGTCTGGTA-3'; SEQ ID NO: 37) were used.

These three components of the nucleic acid encoding the chimeric signalling peptide/polypeptide/LAMP-1 polypeptide fragment were each restricted with the respective restriction endonucleases after the PCR reaction, purified and subsequently introduced in three steps into the, in the following denoted, BamHI-restricted expression vectors. In the case of this method, subsequently the coding regions of the LAMP-1 leader, any arbitrary polynucleotide, here for example of the EBV-BZLF-1 protein or of the human MBP protein as well as the coding nucleic acid of the C-terminal, the transmembrane domain and the cytoplasmatic part of the LAMP-1 protein were inserted into the plasmids pcDNA3.1(+)mPGKPA, pcDNA3.1(+)hPGKPA, pcDNA3.1(+)hDHFRPA, pcDNA3.1(+)hEF-1αPA, pcDNA3.1(+)hUbCPA, pcDNA3.1(+)hICIPA, respectively into the pcDNA3.1(+) dNeomPGKPA, pcDNA3.1(+)dNeohPGKPA, pcDNA3.1(+)dNeohDHFRPA, pcDNA3.1(+)dNeohEF-1αPA, pcDNA3.1(+)dNeohUbCPA, pcDNA3.1(+)dNeohICIPA, pcDNA3.1(+) and into pcDNA3.1(+)dNeo. The expression vectors generated in such a way obtained the denotations (pcDNA3.1(+)mPGKPA-Z/LAMP, pcDNA3.1(+)hPGKPA-Z/LAMP, pcDNA3.1(+)hDHFRPA-Z/LAMP, pcDNA3.1(+)hEF-1PA-Z/LAMP, pcDNA3.1(+)hUbCPA-Z/LAMP, pcDNA3.1(+) hICIPA-Z/LAMP, as well as pcDNA3.1(+)dNeomPGKPA-Z/LAMP, pcDNA3.1(+)dNeohPGKPA-Z/LAMP, pcDNA3.1(+)dNeohDHFRPA-Z/LAMP, pcDNA3.1(+)dNeohEF-1αPA-Z/LAMP, pcDNA3.1(+)dNeohUbCPA-Z/LAMP, pcDNA3.1(+)dNeohICIPA-Z/LAMP, pcDNA3.1(+)-Z/LAMP (FIG. 3) and pcDNA3.1(+)dNeo-Z/LAMP, respectively (pcDNA3.1(+)mPGKPA-MBP/LAMP, pcDNA3.1(+) hPGKPA-MBP/LAMP, pcDNA3.1(+)hDHFRPA-MBP/LAMP, pcDNA3.1(+)hEF-1αPA-MBP/LAMP, pcDNA3.1(+)hUbCPA-MBP/LAMP, pcDNA3.1(+)hICIPA-MBP/LAMP, as well as pcDNA3.1(+)dNeomPGKPA-MBP/LAMP, pcDNA3.1(+)dNeohPGKPA-MBP/LAMP, pcDNA3.1(+)dNeohDHFRPA-MBP/LAMP, pcDNA3.1(+) dNeohEF-1αPA-MBP/LAMP, pcDNA3.1(+)dNeohUbCPA-MBP/LAMP, pcDNA3.1(+)dNeohICIPA-MBP/LAMP, pcDNA3.1(+)-MBP/LAMP and pcDNA3.1(+)dNeo-MBP/LAMP.

EXAMPLE 3

Generation of Vectors which Induce a Membrane Anchoring of the Polypeptide Being Expressed by Means of the Constitutive Promoter (P$_2$)

The cloning of chimeric polypeptides consisting of the N-terminal signalling peptide of the human LAMP-1 protein, any arbitrary polypeptide, for example the EBV BZLF-1 protein or the human MBP protein as well as of a heterologous transmembrane domain, for example of the Epstein-Barr virus gp220/350 coat protein, was performed sequentially using the compatible restriction sites BamHI and BglII.

The amplification of the nucleic acid sequence encoding the signalling peptide of LAMP-1 as well as of the coding sequences of the BZLF-1 and MBP proteins was performed as described in detail in example 2.

The amplification of the EBV gp220/350 transmembrane domain (EBV-TM) was performed by means of PCR using a high fidelity Pfu polymerase (Stratagene) from the plasmid pBRBamHI-L (Skare and Strominger, (1980), Proc. Natl. Acad. Sci. USA 77, 3860-3864) using the following conditions: introductory denaturation step: 95° C., 2 min., subsequently followed by a 3-step PCR (35 cycles) with the following conditions: denaturation: 95° C., 1 min.; annealing 60° C., 1 min.; elongation: 72° C., 1 min., final polymerisation step at 72° C. for 10 min. with subsequent permanent cooling at 4° C. For amplification the primers P33 (5' primer: 5'-GCAGGAGATCTAGCGGGGCAGGATCCAT-GCTAGTACTTCAATGGGCCTCTCTG-3'; SEQ ID NO: 38) and P34 (3' primer: 5'-GCAGGCAGATCTTTATACAT-ACCTCTCGGCCTC-3'; SEQ ID NO: 39) were used.

These three components of the nucleic acid encoding the chimeric signalling peptide/polypeptide/EBV-TM polypeptide fragment were each restricted by the respective restriction endonucleases after the PCR reaction, purified and inserted sequentially in three steps into BamHI-restricted, in the following denoted, expression vectors each. In the case of this method sequentially the coding regions of the LAMP-1 leader, of any arbitrary polynucleotide, here for example of the EBV-BZLF-1 protein or the human MBP protein as well as the nucleic acid encoding the EBV gp220/350 transmembrane domain were ligated into the plasmids pcDNA3.1(+) mPGKPA, pcDNA3.1(+)hPGKPA, pcDNA3.1(+)hDH-FRPA, pcDNA3.1(+)hEF-1αPA, pcDNA3.1(+)hUbCPA, pcDNA3.1(+)hICIPA, respectively pcDNA3.1(+) dNeomPGKPA, pcDNA3.1(+)dNeohPGKPA, pcDNA3.1(+) dNeohDHFRPA, pcDNA3.1(+)dNeohEF-1αPA, pcDNA3.1 (+)dNeohUbCPA, pcDNA3.1(+)dNeohICIPA, pcDNA3.1 (+) and into pcDNA3.1(+)dNeo. The expression vectors which were generated in such a way obtained the denotations (pcDNA3.1(+)mPGKPA-Z/TM, pcDNA3.1(+)hPGKPA-Z/TM, pcDNA3.1(+)hDHFRPA-Z/TM, pcDNA3.1(+)hEF-1αPA-Z/TM, pcDNA3.1(+)hUbCPA-Z/TM, pcDNA3.1(+) hICIPA-Z/TM, as well as pcDNA3.1(+)dNeomPGKPA-Z/TM, pcDNA3.1(+)dNeohPGKPA-Z/TM, pcDNA3.1(+) dNeohDHFRPA-Z/TM, pcDNA3.1(+)dNeohEF-1αPA-Z/TM, pcDNA3.1(+)dNeohUbCPA-Z/TM, pcDNA3.1(+) dNeohICIPA-Z/TM, pcDNA3.1(+)-Z/TM (FIG. 4) and pcDNA3.1(+)dNeo-Z/TM, respectively (pcDNA3.1(+) mPGKPA-MBP/TM, pcDNA3.1(+)hPGKPA-MBP/TM, pcDNA3.1(+)hDHFRPA-MBP/TM, pcDNA3.1(+)hEF-1αPA-MBP/TM, pcDNA3.1(+)hUbCPA-MBP/TM, pcDNA3.1(+)hICIPA-MBP/TM, as well as pcDNA3.1(+) dNeomPGKPA-MBP/TM, pcDNA3.1(+)dNeohPGKPA-MBP/TM, pcDNA3.1(+)dNeohDHFRPA-MBP/TM, pcDNA3.1(+)dNeohEF-1αPA-MBP/TM, pcDNA3.1(+) dNeohUbCPA-MBP/TM, pcDNA3.1(+)dNeohICIPA-MBP/TM, pcDNA3.1(+)-MBP/TM and pcDNA3.1(+)dNeo-MBP/TM.

The correctness of the constructs described in the example 1 to 3 was confirmed by sequencing.

The expression vectors described in the examples 1 to 3 are used in the methods according to the invention for the search for T-cell epitopes and for the detection of T-cells with known epitope-restriction, respectively, where the measurable change of the expression of a polypeptide that is naturally expressed in the APC as a result of an epitope-specific recognition by means of a T-cell, serves as a marker, for example the naturally increased expression of the OX40 ligand or of the 4-1 BB ligand.

EXAMPLE 4

Cloning of gene transfer vectors comprising a first promoter which is specifically inducible in antigen presenting cells by the epitope-specific contact with a T-cell, comprising a nucleic acid being functionally linked to this first promoter and encoding a marker gene, further comprising a second promoter being constitutive in antigen presenting cells and comprising a nucleic acid being functionally linked to this second promoter.

Cloning of the Vector Backbone pcDNA3.1(+) OX40LAeGFP According to the Invention as well as the Vectors pcDNA3.1(+)OX40LAeGFP-Z and pcDNA3.1(+) OX40LAeGFP-MBP According to the Invention The starting vector for the cloning of the vector backbones pcDNA3.1(+)OX40LAeGFP according to the invention (FIG. 5A), as well as for the vectors pcDNA3.1(+) OX40LAeGFP-Z (FIG. 5B) and pcDNA3.1(+) OX40LAeGFP-MBP (FIG. 5C) according to the invention, was the plasmid pcDNA3.1(+) (Invitrogen). The promoter of the OX40 ligand which is inducible by an epitope-specific contact of a T-cell with an epitope-presenting APC was amplified from total DNA from human PBMC by means of the PCR method.

The 979 bp comprising sequence of the promoter of the OX40 ligand was generated by PCR using the following amplification conditions: introductory denaturation step: 95° C., 2 min., followed by two sequential 3-step PCRs with the following conditions: first round of PCR-amplification (10 cycles): denaturation: 95° C., 45 sec.; annealing 50° C., 1 min.; elongation: 72° C., 2 min. Subsequently a second round of PCR-amplification followed (30 cycles) with the following conditions: denaturation: 95° C., 45 sec.; annealing 60° C., 1 min.; elongation: 72° C., 2 min. with a final polymerisation step at 72° C. for 10 min. with subsequent permanent cooling at 4° C. For amplification the primers P35 (5' primer: 5'-GGCGGGGGATCCGGTACCTGGTGTCTATTG-3'; SEQ ID NO: 40) and P36 (3' primer: 5'-GGCGG-GAGATCTCTTCACAATCTGGGTAG-3'; SEQ ID NO: 41) were used. The restriction sites contained within the primers (BamHI in the 5' primer; BglII in the 3' primer) are depicted in italics. The sequence of the amplified PCR fragment is depicted in FIG. 5 and SEQ ID NO: 1. The obtained PCR product was purified and digested with the restriction enzymes BamHI and BglII, purified and cloned into the BglII-linearised plasmid pcDNA3.1(+). The plasmid generated in such a way comprising 641 bp was denoted pcDNA3.1 (+)OX40L.

Subsequently the 224 bp comprising bovine growth hormone (BGH) polyadenylation sequence was amplified from the pcDNA3.1(+) vector by PCR using suitable PCR conditions (introductory denaturation step: 95° C., 2 min., subsequent 3-step PCR (35 cycles) with the following conditions: denaturation: 95° C., 30 sec.; annealing 55° C., 1 min.; elongation: 72° C., 1 min. and a final polymerisation step at 72° C. for 10 min. with subsequent permanent cooling at 4° C.). For amplification the primers P37 (5' primer: 5'-GGCGG-GAGATCCTGTGCCTTCTAGTTGCC-3'; SEQ ID NO: 42) and P38 (3' primer: 5'-GGCGGGGGATCCCCATAGAGC-CCACCGC-3'; SEQ ID NO: 43) were used. The restriction sites (BglII in the 5' primer; BamHI in the 3' primer) contained within the primers are depicted in italics. The PCR-amplified band was purified as described previously, restricted with the restriction enzymes BglII and BamHI, and the in such a way obtained band was ligated into the BglII-linearised plasmid pcDNA3.1(+)0X40L. The vector generated in such a way was denoted pcDNA3.1 (+)OX40LA.

Subsequently the gene for the "enhanced green fluorescent protein" (eGFP) was amplified from the plasmids pRC/CMV-EGFP (Vogel et al., 1998, BioTechniques 143, 1967-1983) by PCR using suitable PCR conditions (introductory denaturation step: 95° C., 2 min., subsequently a 3-step PCR (35 cycles) with the following conditions: denaturation: 95° C., 30 sec.; annealing 55° C., 1 min.; elongation: 72° C., 2 min., and a final polymerisation step at 72° C. for 10 min. with subsequent permanent cooling at 4° C.). For amplification the primers P39 (5' primer: 5'-GGCGGGGGATCCCGCCAC-CATGGTGAGCAAGG-3'; SEQ ID NO: 44) and P40 (3' primer: 5'-GGCGGGAGATCTTTACTTGTA-CAGCTCGTCC-3'; SEQ ID NO: 45) were used. The PCR-amplified specific band with a size of 752 bp was purified as described previously, digested with the restriction enzymes BamHI and BglII, and the obtained band was ligated into the BglII-linearised plasmid pcDNA3.1(+)OX40LA. The in such a way generated vector comprising 7378 bp was denoted pcDNA3.1(+)OX40LAeGFP (FIG. 5A). This vector can be used as the vector backbone for the cloning of the vectors according to the invention for the search for epitopes and the detection of reactive T-cells.

Subsequently, the cDNA for the EBV BZLF-1 protein was amplified from viral DNA of the EBV strain B95-8 within the total DNA of infected marmoset cells by PCR using suitable PCR-conditions (introductory denaturation step: 95° C., 2 min., subsequently a 3-step PCR (15 cycles) with the following conditions: denaturation: 95° C., 30 sec.; annealing 52° C., 1 min.; elongation: 72° C., 2 min., followed by 25 cycles with the following conditions: denaturation: 95° C., 30 sec.; annealing 52° C., 1 min.; elongation: 72° C., 2 min., and a final polymerisation step at 72° C. for 10 min. with a subsequent permanent cooling at 4° C.). In the case of the PCR reaction for the amplification of the BZLF-1 cDNA 2.5% DMSO were added to the PCR sample. For amplification the primers P41 (5' primer: 5'-GGCGGTCTAGATTAGAAATT-TAAGAGATCC-3'; SEQ ID NO: 46) and P42 (3' primer: 5'-GGCGGGGAATTCATGATGGACCCAAACTCG-3'; SEQ ID NO: 47) were used. The PCR-amplified 970 nucleotide comprising band was purified as described previously, restricted with the restriction enzymes XbaI and EcoRI, and the obtained band was ligated into the respectively with EcoRI and XbaI linearised plasmid pcDNA3.1(+)OX40LAeGFP. The vector generated in such a way was denoted pcDNA3.1(+)OX40LAeGFP-Z (FIG. 5B).

Alternatively, the cDNA for the MBP protein was amplified from total DNA from brain cells by PCR using suitable conditions (introductory denaturation step: 95° C., 2 min.; subsequently followed by a 3-step PCR (35 cycles) with the following conditions: denaturation: 95° C., 30 sec.; annealing 55° C., 1 min.; elongation: 72° C., 2 min. and a final polymerisation step at 72° C. for 10 min. with a subsequent permanent cooling at 4° C.). For amplification the primers P43 (5' primer: 5'-GGCGGTCTAGAATGGCGTCACA-GAAGAGACC-3'; SEQ ID NO: 48) and P44 (3' primer: 5'-GGCGGGGAATTCTCAGCGTCTAGCCATGGG-3'; SEQ ID NO: 49) were used. The PCR-amplified 585 nucleotides comprising band was purified as described previously, restricted with the restriction enzymes XbaI and EcoRI, and the obtained bands were ligated into the respectively with EcoRI and XbaI linearised plasmid pcDNA3.1(+) OX40LAeGFP. The vector generated in such a way was denoted pcDNA3.1(+)OX40LAeGFP-MBP (FIG. 5C).

In addition, a first promoter ($P_1$), here exemplary the OX40 ligand promoter and 4 variants of the 4-1 BB ligand promoter, which is specifically inducible in antigen presenting cells by the epitope specific contact with a T-cell, as well as a nucleic acid encoding a marker gene, here exemplary the eGFP, which is functionally linked to this first promoter, were inserted in all expression plasmids which are described in the examples 1-3.

For this, three nucleic acid modules, the sequence of a first promoter ($P_1$) being inducible in APC, a BGH polyadenylation sequence and a sequence for a marker, exemplary the nucleic acid encoding eGFP, were each restricted and purified after performed PCR-amplification and inserted sequentially in three steps into a BglII-restricted expression vector each. Hereby, for all cloning steps the BglII-restriction site was used which is localised at position 13 of the vector pcDNA3.1 (+) (Invitrogen) that forms the basis for all generated plasmids. Other BglII-restriction sites which were generated within the vectors due to the performed cloning steps were deleted by means of a QuickChange Site-Directed Mutagenis Kit following the manufacturer's (Stratagene) protocol in such a way that the amino acid sequence of the polypeptide and the functionality of the nucleic acid, respectively, stays unchanged. The selection of suited oligonucleotides for mutagenesis and the performance of the method are established and state of the art.

Amplification of the Human OX40 Ligand Promoter

The 979 bp comprising sequence of the murine PGK promoter was obtained by PCR from isolated chromosomal DNA from human PBMCs using the following conditions: introductory denaturation step: 95° C., 2 min., subsequently followed by two 3-step PCRs with the following conditions: first round of PCR-amplification (10 cycles): denaturation: 95° C., 45 sec.; annealing 50° C., 1 min.; elongation: 72° C., 2 min. Subsequently followed by a second round of PCR-amplification (30 cycles) with the following conditions: denaturation: 95° C., 45 sec.; annealing: 60° C., 1 min.; elongation: 72° C., 2 min. with a final polymerisation step at 72° C. for 10 min. with subsequent permanent cooling at 4° C. For amplification the primers P45 (5' primer: 5'-GGCGGGG-GATCCGGTACCTGGTGTCTATTG-3'; SEQ ID NO: 50) and P46 (3' primer: 5'-GGCGGGAGATCTCTTCA-CAATCTGGGTAG-3'; SEQ ID NO: 51) were used. The restriction sites (BamHI in the 5' primer; BglII in the 3' primer) contained within the primers are depicted in italics.

Amplification of the Human 4-1 BB Ligand Promoter (Long Variant of the 4-1 BB Ligand Promoter (VI))

The 2047 bp comprising sequence of the human 4-1 BB ligand promoter was isolated by PCR from isolated chromosomal DNA from human PBMCs using the following amplification conditions: introductory denaturation step: 98° C., 2 min., followed by three subsequent 3-step PCRs with the following conditions: first round of PCR-amplification (30 cycles): denaturation: 95° C., 1 min.; annealing: 66.1° C., 1 min.; elongation: 72° C., 4.5 min. Subsequently followed by a second round of PCR-amplification (15 cycles) with the following conditions: denaturation: 98° C., 1 min.; annealing: 58° C., 1 min.; elongation: 72° C., 4.5 min. and a third round of PCR-amplification (25 cycles) with the following conditions: denaturation: 98° C., 1 min.; annealing: 71° C., 1 min.; elongation: 72° C., 4.5 min. with a final polymerisation step at 72° C. for 10 min. with subsequent permanent cooling at 4° C. For amplification the primers P47 (5' primer: 5'-GGCGGGG-GATCCCCGGATTGGCCGCCTCCAGCAG-3'; SEQ ID NO: 52) and P48 (3'primer: 5'-GGCGGGGGATCCGAC-GAGAGACTGCGGGAAGACAC-3'; SEQ ID NO: 53) were used. The obtained PCR-amplificate was subsequently purified, restricted with BamHI and inserted in the respectively BamHI-restricted pcDNA3.1(+)-vector. The obtained construct was denoted pcDNA3.1(+)4-1BBL. Subsequently, the BglII-restriction site within the 4-1 BB ligand promoter (at position 1625 to 1630 of the 2023 nucleotide comprising full length promoter) was deleted by means of a QuickChange Site-Directed Mutagenesis Kit following the manufacturer's (Stratagene) protocol by the exchange of a nucleotide at the position 1626 (1626 G to A)-(1624-AGATCT-1631) to 1626 (1624-AAATCT-1631). The resulting plasmid obtained the denotation pcDNA3.1(+)4-1BBL1626.

Amplification of the Mutated (1626 G to A) (Human 4-1 BB Ligand Promoter (Long Variant of the 4-1 BB Ligand Promoter (V1))

The 2047 bp comprising sequence of the human 4-1 BB ligand promoter was isolated by PCR from the plasmid pcDNA3.1(+)4-1BBL1626 using the following amplification conditions: introductory denaturation step: 98° C., 2 min., subsequently followed by three sequential 3-step PCRs with the following conditions: first round of PCR-amplification (30 cycles): denaturation: 95° C., 1 min.; annealing: 66.1° C., 1 min.; elongation: 72° C., 4.5 min. Subsequently followed by a second round of PCR-amplification (15 cycles) with the following conditions: denaturation: 98° C., 1 min.; annealing: 58° C., 1 min.; elongation: 72° C., 4.5 min., and a third round of PCR-amplification (25 cycles) with the following conditions: denaturation: 98° C., 1 min.; annealing: 71° C., 1 min.; elongation: 72° C., 4.5 min. with a final polymerisation step at 72° C. for 10 min. with a subsequent permanent cooling at 4° C. For amplification the primers P49 (5' primer: 5'-GGCGGGGGATCCCCGGATTGGCCGCCTC-CAGCAG-3'; SEQ ID NO: 54) and P50 (3' primer: 5'-GGCGGGAGATCTGACGAGAGACTGCGG-GAAGACAC-3'; SEQ ID NO: 55) were used.

Amplification of the Human 4-1 BB Ligand Promoter (in the 5' Region Truncated Variant of the 4-1 BB Ligand Promoter (V2))

The 1433 bp comprising sequence of the human 4-1 BB ligand promoter (V2) was isolated by PCR from the plasmid pcDNA3.1(+)4-1BBL1626 using the following amplification conditions: introductory denaturation step: 98° C., 2 min., subsequently followed by three sequential 3-step PCRs with the following conditions: first round of PCR-amplification (30 cycles): denaturation: 95° C., 1 min.; annealing: 64.1° C., 1 min.; elongation: 72° C., 4.5 min. Subsequently followed by a second round of PCR-amplification (15 cycles) with the following conditions: denaturation: 98° C., 1 min.; annealing: 58° C., 1 min.; elongation: 72° C., 3.5 min., and a third round of PCR-amplification (25 cycles) with the following conditions: denaturation: 98° C., 1 min.; annealing: 69° C., 1 min.; elongation: 72° C., 3.5 min. with a final polymerisation step at 72° C. for 10 min. with subsequent permanent cooling at 4° C. For amplification the primers P51 (5' primer: 5'-GGCGGGG-GATCCGGAGCCAGAGATAGGGAGAGTC-3'; SEQ ID NO: 56) and P50 (3' primer: 5'-GGCGGGAGATCTGAC-GAGAGACTGCGGGAAGACAC-3'; SEQ ID NO: 55) were used.

Amplification of the Human 4-1 BB Ligand Promoter (in the 5' Region Further Truncated Variant of the 4-1 BB Ligand Promoter (V3))

The 874 bp comprising sequence of the human 4-1 BB ligand promoter (V3) was isolated by PCR from the plasmid pcDNA3.1(+)4-1BBL1626 using the following amplification conditions: introductory denaturation step: 98° C., 2 min., subsequently followed by three sequential 3-step PCRs with the following conditions: first round of PCR-amplification (30 cycles): denaturation: 95° C., 1 min.; annealing: 66° C., 1 min.; elongation: 72° C., 2 min. Subsequently followed by a second round of PCR-amplification (15 cycles) with the following conditions: denaturation: 98° C., 1 min.; annealing: 55° C., 1 min.; elongation: 72° C., 2 min., and a third round of PCR-amplification (25 cycles) with the following conditions: denaturation: 98° C., 1 min.; annealing: 69° C., 1 min.; elongation: 72° C., 2 min. with a final polymerisation step at 72° C. for 10 min. with subsequent permanent cooling at 4° C. For amplification the primers P52 (5' primer: 5'-GGCGGGG-GATCCCAGCCAGAGACAGCGACAGAG-3'; SEQ ID NO: 57) and P50 (3' primer: 5'-GGCGGGAGATCTGAC-GAGAGACTGCGGGAAGACAC-3'; SEQ ID NO: 55) were used.

Amplification of the Human 4-1 BB Ligand Promoter (in the 5' Region Further Truncated Variant of the 4-1 BB Ligand Promoter (V4))

The 386 bp comprising sequence of the human 4-1 BB ligand promoter (V4) was isolated by PCR from the plasmid pcDNA3.1(+)4-1BBL1626 using the following amplification conditions: introductory denaturation step: 98° C., 2 min., subsequently followed by three sequential 3-step PCRs with the following conditions: first round of PCR-amplification (30 cycles): denaturation: 95° C., 1 min.; annealing: 66° C., 1 min.; elongation: 72° C., 2 min. Subsequently followed by a second round of PCR-amplification (15 cycles) with the following conditions: denaturation: 98° C., 1 min.; annealing: 55° C., 1 min.; elongation: 72° C., 2 min., and a third round of PCR-amplification (25 cycles) with the following conditions: denaturation: 98° C., 1 min.; annealing: 69° C., 1 min.; elongation: 72° C., 2 min. with a final polymerisation step at 72° C. for 10 min. with subsequent permanent cooling at 4° C. For amplification the primers P53 (5' primer: 5'-GGCGGGG-GATCCCCCACTGCAGAGGCAATCAACAAG-3'; SEQ ID NO: 58) and P50 (3' primer: 5'-GGCGGGAGATCTGAC-GAGAGACTGCGGGAAGACAC-3'; SEQ ID NO: 55) were used.

The 224 bp comprising bovine growth hormone (BGH) polyadenylation sequence and the gene for the "enhanced green fluorescent protein" (eGFP) were obtained by PCR as already described in example 4.

The three nucleic acid components for the expression of a marker by means of an inducible promoter ($P_1$), namely the nucleic acid sequence of a promoter, of a BGH polyadenylation signal sequence and of a nucleic acid encoding a marker were—as described in the following—sequentially inserted into the plasmids listed hereafter. Step 1: digestion of the nucleic acid of the promoter obtained by PCR with the enzymes BamHI and BglII and ligation of the thereby obtained nucleic acid into BglII restricted target vectors. Step 2: digestion of the obtained nucleic acid of the BGH polyadenylation signal sequence obtained by PCR with the enzymes BglII and BamHI and ligation of the thereby obtained nucleic acid into the target vectors generated in step 1 and again restricted with BglII. Step 3: digestion of the nucleic acid of the marker (eGFP) obtained by PCR with the enzymes BamHI and BglII and ligation of the thereby obtained nucleic acid into the target vectors generated in step 2 and again restricted with BglII.

With this method 4 different first promoters, the OX40L, the 4.1BBL(V1), the 4.1BBL(V2), the 4.1BBL(V3) and the 4.1BBL(V4) promoter, being specifically inducible in antigen presenting cells by the epitope-specific contact with a T-cell as well as a nucleic acid encoding a marker gene (eGFP) being functionally linked with this first promoter were inserted into the plasmids pcDNA3.1(+), pcDNA3.1(+) dNeo, as well as into the expression vectors listed in the examples 1 to 3, containing a second promoter being constitutive in antigen-presenting cells and containing a nucleic acid being functionally linked to this second promoter. The plasmids which were generated in such a way were denoted by the addition of the denotation of the promoter (OX40L, 4.1BBL(V1), 4.1BBL(V2), 4.1BBL(V3) or 4.1BBL(V4)) to the original name. So for example the plasmid pcDNA3.1(+)-Z/LAMP is denoted pcDNA3.1(+)-Z/LAMP/OX40L (FIG. 5D) after insertion of the nucleic acid for the OX40 ligand promoter, the BGH polyadenylation signal sequence and the marker eGFP.

Potential restriction endonuclease restriction sites which might interfere with the procedure of the cloning steps described in the examples 1 to 4 were deleted by means of a QuickChange Site-Directed Mutagenesis Kit following the manufacturer's (Stratagene) protocol in such a way that the amino acid sequence of the polypeptide and the functionality of the nucleic acid, respectively, stays unchanged. The selection of suitable oligonucleotides for mutagenesis and the performance of the method are established and state of the art. The correctness of the sequence and the orientation of the polynucleotides which were integrated into the respective vectors were confirmed by sequencing.

EXAMPLE 5

Transfection of the Vectors According to the Invention into Populations of Purified APC or Purified PBMC by Means of the Nucleovector™ Technology (Amaxa)

The preparation of peripheral mono-nucleated cells of the blood (PBMC) from whole blood of voluntary donors or patients was performed as described hereafter: freshly extracted whole blood (50 to 100 ml; not older than 8 h) of a healthy test person was spiked with 20 IU/ml heparin. 50 ml-Leukosep-vials with a separating membrane were filled with 15 ml Ficoll-Histopaque (Sigma, Deisenhofen, Germany) and centrifuged for 2 min. at 500×g. Subsequently, the tubes were filled with the heparinised whole blood and mixed 1:1 (vol/vol) with sterile PBS/0.5% BSA. The samples were centrifuged for 30 to 40 min. at 400×g without decelerating the rotor at the end of the spin. The lymphocyte-containing turbid interphase was removed carefully and washed in 3 volumes of T-cell medium (RPMI 1640 medium with 10% heat inactivated (30 min. at 56° C.) human AB serum, 2 mM glutamine and 100 mg/ml kanamycin and gentamycin, respectively, (all components by PanSystem, Aidenbach, Germany)) for three times (200×g; 10 to 15 min. at room temperature) and resuspended with a cell number of $2 \times 10^6$ cells/ml in RPMI 1640 medium (Gibco) with 10% human AB serum, 100 µg/ml streptomycin, 100 U/ml penicillin and 2 mM GlutaMAX (Invitrogen/Live Technologies) and stored in a humidified incubator with 5% $CO_2$ gassing at 37° C. prior to the further purification of defined APC- and T-cell populations. By means of this method from 100 ml whole blood (60% erythrocytes; 40% leukocytes) are extracted about $1 \times 10^7$ to $1 \times 10^8$ PBMCs with an average composition of about 60%-70% T-cells, 5%-10% B-cells, 10%-20% monocytes/macrophages and about 10% of other cells.

The purification of B-cells from freshly prepared PBMCs was performed by a positive selection by means of immunomagnetic CD19 MicroBeats following the manufacturer's protocol (Miltenyi Biotec).

For this, the isolated PBMC were counted and resuspended in a concentration of $10^7$ cells/80 µl MACS buffer (PBS, 0.5% BSA and 2 mM EDTA, degassed). For each $10^7$ PBMC 20 µl MACS CD10 MicroBeats were added and incubated for 15 min. at 6° C. Subsequently, the labelled cell suspension was mixed with 2 ml buffer for $10^7$ PBMC each and centrifuged for 10 min. at 300×g in a Hettich-Rotanta table centrifuge. The supernatant was removed carefully and the cells were resuspended in 500 µl MACS-buffer. Prior to loading on a column, the cells were individualised by filtration through a cell sieve, 70 µm mesh size (BectonDickinson, Heidelberg, Germany). For the positive selection of the magnetically labelled cells, columns of the type XS+ were chosen (max. $10^9$ positive cells) and placed into a MACS separator (Miltenyi Biotec, Germany). The columns were washed once to twice with 10 ml MACS buffer until the flowthrough was clear. Subsequently, the individualised cells were loaded on the prepared column and the negative fraction was eluted. The column was again washed 3× with MACS buffer, withdrawn from the MACS-separator and transferred into a sterile plastic vial. The B-cells were subsequently eluted by the loading of MACS buffer and the exertion of a feeble pressure by a plunger belonging to the column. After this, the cells were stored until transfection with a cell number of $1 \times 10^6$ cells/ml in RPMI 1640 medium (Gibco) with 10% human AB serum, 100 µg/ml streptomycin, 100 U/ml penicillin, and 2 mM GlutaMAX (Invitrogen/Live Technologies) at 37° C. in a humidified incubator with 5% $CO_2$ gassing.

In the same manner $CD3^+$ T-cells were depleted from PBMCs by positive selection using MACS CD3 MicroBeads and the obtained cell suspension was characterised in regard of its composition by means of FACS before the transfer of nucleic acid.

Subsequently, the obtained cell populations were characterised in regard to their composition by means of a FACS device using suitable, dyestuff-labelled antibodies against cell type-specific surface molecules (CDs). By using this method, B-cells could be obtained having a purity of about 83% (see table 1A). Analogously, CD3-positive T-cells were depleted from PBMCs by means of the Miltenyi method following the manufacturer's protocol and the resulting cell populations were characterised by means of FACS analysis. The obtained cell suspension was composed of 3.37% B-cells ($CD19^+$), 58% $CD4^+$-cells (monocytes and remaining T-cells), about 1.55% contaminating T-cells ($CD3^+$); thereof about 0.35% T-helper cells and 1.2% CTL ($CD8^+$) and 58% monocytes ($CD3^-$, $CD4^+$).

Transfection of $CD3^+$ Depleted PBMC and Purified B-Cells, Respectively, with the Vectors According to the Invention.

Exemplarily, the transfection of $CD3^+$ depleted PBMC (FIG. 6A) and the purified B-cells (FIG. 6B), respectively, was performed with the vector pcDNA3.1(+)dNeo-eGFP according to the invention by means of the Nucleovector™ technology using the human B cell Nucleovector™ kit following the detailed manufacturer's protocol (Amaxa, Germany). As controls the cells were treated with the plasmid pcDNA3.1(+). At this 1×10$^7$ to 3×10$^7$ CD3 depleted PBMCs and purified CD19$^+$ B-cells, respectively, per ml were centrifuged (200×g, 10 min. at room temperature) and the sedimented cells were resuspended in the "Human B-Cell Nucleofactor" solution at a concentration of 1×10$^6$ to 3×10$^6$ cells/ml. After this 100 μl of the cell suspension was spiked with 5 μl DNA and the sample was pipetted into a cuvette avoiding air bubbles. Subsequently, the cells were transfected by means of a Nucleofector device using a preset program of the manufacturer (Amaxa, Program U-15). After performed transfection 500 μl of pre-warmed medium (RPMI 1640 medium (Gibco) with 10% human AB serum, 100 μg/ml streptomycin, 100 U/ml penicillin and 2 mM GlutaMAX (Invitrogen/Live Technologies)) were added and the cells were incubated afterwards at 37° C. in a humidified incubator with 5% $CO_2$ gassing. The transfection efficiency was determined at several time points after performed transfection (for example 12 to 72 hours, exemplary for 17 hours (FIGS. 6A, B; tables 2A-D)) by means of a FACS device measuring the number of fluorescent cells (detection of a GFP reporter). For this, the transfected cells were 2× washed with FACS buffer (PBS without bivalent ions, 1% FCS, 0.9 mg/ml acid) and after this resuspended in a density of 5×10$^5$ cells in FACS buffer. Subsequently, the number of fluorescent cells was determined by means of a FACS device (FACS Calibur, BD) by measuring of the fluorescence 1 (FL1) against the forward scatter. These experiments showed that due to the Nucleovector™ Technology (Amaxa) about 13.5% of B-cells and 30% of the monocytes in the mixed population of CD3 depleted PBMCs show a significant eGFP production (table 2A). In populations of high-purity B-cells the transfection rate of B-cells amounted to only about 7.4% in contrast (table 2B). The cells being transfected with a control vector pcDNA3.1 (+) did not show any significant eGFP production in these experiments (tables 2C,D). These analyses substantiate the suitability of the Nucleovector™ Technology of Amaxa for the transfer of the vectors according to the invention into APC.

TABLE 1A

FACS analysis of the composition of the population of CD3$^+$ depleted PBMCs which was obtained by the Miltenyi method for CD3 depletion.

| cell type | % |
| --- | --- |
| CD19$^+$ | 3.37 |
| CD4$^+$ | 58.39 |
| CD3$^+$ | 1.52 |
| CD3$^-$CD4$^+$ | 58.30 |
| CD3$^+$CD4$^+$ | 0.37 |
| CD3$^+$CD8$^+$ | 1.19 |

TABLE 2C

Detection of the fluorescence from different cell populations in CD3 depleted PBMCs by means of FACS analysis of the nucleofection with pcDNA3.1(+) (FIG. 6A, middle)

| fluorescent cells | % |
| --- | --- |
| total | 0.28 |
| CD19$^+$ | 0.70 |
| CD4$^+$/Th | 1.03 |
| CD3$^+$ | 0.88 |
| CD3$^+$CD4$^-$ | 0.27 |

TABLE 2A

Detection of the fluorescence from different cell populations in CD3 depleted PBMCs by means of FACS analysis after nucleofection with pcDNA3.1dNeo-eGFP (FIG. 6A, right)

| fluorescent cells | % |
| --- | --- |
| total | 34.94 |
| CD19$^+$ | 13.48 |
| CD4$^+$/Th | 3.79 |
| CD3$^+$ | 5.01 |
| CD3$^+$CD4$^-$ | 30.06 |

TABLE 1B

FACS-analysis of the composition of the B-cells which were obtained by means of the Miltenyi method for B-cell separation

| cell type | % |
| --- | --- |
| CD19$^+$ | 83.38 |
| CD4$^+$ | 0.96 |
| CD3$^+$ | 5.77 |
| CD3$^+$CD4$^+$ | 1.79 |
| CD3$^+$CD8$^+$ | 1.13 |

TABLE 2D

Detection of the fluorescence in enriched non-purified B-cells by FACS after nucleofection with pcDNA3.1(+) (FIG. 6B, middle)

| fluorescent cells | % |
| --- | --- |
| total | 0.31 |
| CD19$^+$ | 0.43 |

TABLE 2B

Detection of the fluorescence in enriched non-purified B-cells by FACS after nucleofection with pcDNA3.1dNeo-eGFP (FIG. 6B, right)

| fluorescent cells | % |
| --- | --- |
| total | 8.92 |
| CD19$^+$ | 7.39 |

In contrast to this, transfection rates of more than 50% could be achieved by means of the Femtosecond Laser Technology in the case of different purified APC populations (monocytes, B-cells, dendritic cells). For this, 1-5×10$^5$ APC were suspended each in a miniaturised sterile cell chamber in 0.5 ml culture medium and 0.2 μg of the pcDNA3.1(+)dNeo-eGFP plasmid. Subsequently, the cells were treated according to an available protocol (Tirlapur and König, (2001) Nature, 418, 290) and the transfection efficiency was determined as already described by means of a FACS device. This method is presently being developed by the company Jenlab GmbH to series-production readiness but is at present not yet commercially available.

EXAMPLE 6

Enhancement of the Marker Expression in the APC According to the Invention After Contact with Epitope-Specific T-Cells The testing for suitability of the APC according to the invention for the detection of epitope-specific T-cells and for the search for epitopes was performed on the basis of a very well characterised model system. This system is based on the experimental results that all HLA-B8 positive, EBV positive test persons exhibit CD8$^+$ cytotoxic T-cells with a high precursor frequency which recognise a specific epitope (RAK-FKQLL; amino acid 190-197) within the EBV protein BZLF-1 (Bogedain et al., 1995, J. Virol. 69, 4872-4879; Benninger-Döring et al., 1999, Virol. 264, 289-297).

A: Enhanced Expression of a Natural Marker (OX40L) on Transfected APC After Incubation with the Plasmid pcDNA3.1(+)dNeo-Z/LAMP According to the Invention In the case of these examinations, monocytes of an HLA-B8 positive EBV sero-positive donor (SD) and as a control of an HLA-B8 positive, EBV sero-negative donor (SN) were negatively purified using a mixture of antibody-labelled magnetic beads (Miltenyi) according to the manufacturer's protocol, and the purified monocytes were differentiated in RPMI medium (10% FCS) by the addition of 25 ng/ml IL-4 and 800 U/ml GM-CSF to dendritic cells (DC). At this, the medium was changed on day 4 of the incubation and exchanged by a medium containing GM-CSF, IL-4 and 10 ng/ml TNF-α. After culturing for 7 days the cells were transfected with the plasmid pcDNA3.1 (+)dNeo-Z/LAMP and as a control with the plasmid pcDNA3.1(+)dNeo using the Nucleofactor or Femtolaser technology. After further culturing for 12 to 36 hours in RPMI 1640 medium (Gibco) with 10% human AB serum, 100 µg/ml streptomycin, 100 U/ml penicillin and 2 mM GlutaMAX (Invitrogen/Live Technologies) the cells subsequently were incubated in 20 parallel approaches in different ratios (10:1 to 1:10) of DC and T-cells which were modified according to the invention and were derived from the same patients, with a whole cell number of 5×10$^6$ cells in RPMI 1640 medium (Gibco) with 10% human AB serum, 100 µg/ml streptomycin, 100 U/ml penicillin and 2 mM GlutaMAX (Invitrogen/Live Technologies) for 2 to 72 hours at 37° C. in a humidified incubator with 5% CO$_2$ gassing. After this, the expression of the OX40 ligand on the surface of the dendritic cells was determined by means of a FACS analysis using the OX40L-specific antibody 5A8 (Imura et al. (1996), J. Exp. Med. 183:2185). Thereby in the case of about 2 to 20% (dependent on the experimental protocol) of all pcDNA3.1(+)dNeo-Z/LAMP-plasmid treated DC of the HLA-B8 positive EBV sero-positive donor (SD) in comparison to the with the same plasmid treated DC of the HLA-B8 positive EBV sero-negative donor (SN) as well as with the pcDNA3.1(+)dNeo-control vector treated DCs of both donors, a measurably increased surface expression of the OX40L could be observed. This increased surface expression of OX40L was measurable during a time period of 4 to 72 hours. Similar results were obtained in co-cultivation experiments using B-cells and monocytes as APC.

B: Enhanced Expression of a Natural Marker (OX40L) on Transfected APC After Transfection with the Plasmids pcDNA3(+)OX40LAeGFP-Z and pcDNA3.1(+)dNeo-Z/LAMP/OX40L According to the Invention In the case of these analyses, B-cells as well as monocytes of an HLA-B8 positive EBV sero-positive donor (SD) and as control of an HLA-B8 positive EBV sero-negative donor (SN) were positively purified using specific antibody labelled magnetic beads (Miltenyi) following the manufacturer's protocol and were transfected with the plasmids pcDNA3(+)OX40LAeGFP-Z and pcDNA3.1(+)dNeo-Z/LAMP/OX40L and as a control with the vector pcDNA3.1(+)dNeo after a cultivation for 1 to 24 hours using the Nucleofector or Femtolaser technology. After a further cultivation for 12-36 hours in RPMI 1640 medium (10% human AB serum, 100 µg/ml streptomycin, 100 U/ml penicillin and 2 mM GlutaMAX) the cells were subsequently incubated in 20 parallel approaches in different ratios (10:1 to 1:10) of APC (B-cells or monocytes) and T-cells which were modified according to the invention and derived from the same patients, with a total cell number of 5×10$^6$ cells in RPMI 1640 medium (10% human AB serum, 100 µg/ml streptomycin, 100 U/ml penicillin and 2 mM GlutaMAX) for 12 to 72 hours at 37° C. in a humidified incubator with 5% CO$_2$ gassing. After this, the number of eGFP marker-positive APC was determined by means of a FACS device according to the method described in example 5. Hereby, in about 1 to 20% (dependent on the experimental procedure) of the pcDNA3(+)OX40LAeGFP-Z- and pcDNA3.1(+)dNeo-Z/LAMP/OX40L-plasmid transfected APC of the HLA-B8 positive EBV sero-positive donor (SD) in comparison to the with the same plasmid treated DC of the HLA-B8 positive EBV sero-negative donor (SN) as well as with the pcDNA3.1(+)dNeo control vector treated DCs of both donors, a measurable increased marker production could be observed. This increased fluorescence was measurable over a time period of 4 to 72 hours. Similar results were achieved using DC as APC.

EXAMPLE 7

Isolation of Marker-Positive APC by Means of the FACS-Sorting Method and Isolation of Polynucleotides from Selected Cells For the identification of the polypeptides being recognised by the reactive T-cells of the HLA-B8-positive donor (SD) or APC, which showed an increased marker expression, were selected by means of the FACSsort technology, collected, and the total DNA was prepared from these APC. For transformation of the total DNA into bacteria 20 µl of a DH10B bacterial suspension was mixed with the obtained total DNA and electroporated for about 5 msec. at a voltage of 2400V. After this, the bacteria were shortly cooled on ice, and subsequently mixed with 1 ml LB medium and incubated under shaking for 1.5 hours at 37° C. Finally, different amounts of the bacterial suspension were plated on LB$_{AMP}$ selection plates. These were incubated overnight at 37° C. In these experiments a significant number of ampicillin resistant colonies/plate (10-100) could be generated by the transfection of 1 µg total DNA. By PCR analysis of the bacterial clones using suited EBV BZLF-1-specific primers as well as by sequencing of the plasmids obtained from the bacterial clones using suitable sequencing primers, it could be shown that more than 90% of the resistant bacterial clones contained the expression vectors encoding the BZLF-1 protein.

EXAMPLE 8

Detection of Specific Vector-Encoded Polynucleotides from the Genome of Stably Transfected Insect Cells In the early 90ies a very sensitive method was described by Wolff and colleges allowing to detect even episomal plasmids but also plasmids being stably integrated into the genome of the transfected cells (Wolff et al., 1991). This detection method is based on the observation that plasmids which are episomally present inside the cell but not plasmids which have integrated stably into the genome of a host cell lead to the formation of antibiotics-resistant colonies after the extraction of the total DNA and a subsequent electroporation of the DNA into bacteria. For this the plasmid has to contain a bacterial origin of replication and a selectable bacterial resistance gene.

In control experiments a transformation efficiency of about $10^8$ colonies per µg of transfected plasmid DNA could be determined after electroporation of 1 pg, 5 pg and 10 pg of the plasmid pAM-HBsAg encoding the small coat protein (HbsAg) of the hepatitis B virus (Deml et al., J. Virol. Methods (1999), 79:191-203). A comparable electroporation efficiency was observed when the plasmid DNA was applied together with 1 µg of chromosomal DNA from drosophila Schneider-2 (DS-2) cells. Therefore, the electroporation efficiency of plasmids is not affected by the presence of chromosomal DNA. In contrast, by electroporation of the respective linearised plasmid DNA only very view ampicillin-resistant bacterial colonies could be generated.

In order to test if the plasmid pAM-HbsAg, which has been transfected into DS-2 insect cells by lipofection, is present extra-chromosomal or integrated into the genome of the cells, the total DNA was prepared from three independent samples of this cell line and transfected into bacteria. As a control, bacteria were transformed with total DNA from non-transfected DS-2 cells. In both cases only very view ampicillin-resistant bacterial colonies could be generated by the transfection of 1 µg total DNA. By PCR analysis using HBsAg-specific primers it could be shown that none of these resistant bacterial clones contained the HBsAg gene. Therefore, it can be deduced from these experiments that the total DNA which was prepared from stably transfected DS-2 cells did not contain any detectable amounts of episomally present pAM-HBsAg DNA.

Further electroporation studies were to show that the plasmid DNA is present integrated into the genome of the stably transfected clonal DS-2 cell line. For this purpose, total DNA was obtained from the stably transfected DS-2 cell line and non transfected DS-2 cells, restricted with selected restriction enzymes, re-ligated and transfected into bacteria. By this procedure the integrated copies of the expression plasmid pAM-HBsAg should be turned into extra-chromosomal plasmids which can be detected after electroporation into bacteria by facilitating an ampicillin-resistance. The restriction enzyme EcoRV, which was used for the restriction of the total DNA, singularly cuts the plasmid pAM-HBsAg in the region between the Mtn promoter and the reading frame for the HbsAg reporter gene. By digestion of the chromosomal DNA of the stably with pAM-HBsAg transfected DS-2 cells with EcoRV, re-ligation and electroporation into *E. coli* more than 200 ampicillin-resistant colonies could be obtained. More than 80% of the established bacterial clones proved HBsAg-positive in the PCR. For the further characterisation of these clones the plasmid DNA was prepared from *E. coli* and digested with EcoRV. Most of these bacterial clones contained the "input" plasmid pAM-HBsAg in the original size of about 8.2 kbp. These plasmids having an unchanged size as compared to pAM-HBsAg, probably result from plasmids that integrated in multiple copies to an integration spot within the genome of the host cell. About 15% of the analysed HBsAg-positive bacterial clones contained plasmids that showed a size differing from the co-expression plasmid pAM-HBsAg. These plasmids were probably excised from the genome at border regions of chromosomal DNA and the integrated plasmid DNA whereby besides the plasmid-encoded, another genomic EcoRV restriction site was used being located in proximity to the integrated plasmid. After transfection of bacteria with equally treated chromosomal DNA from non-transfected DS-2 cells 22 ampicillin-resistant bacterial colonies could be generated. All of them proved HBsAg-negative in the PCR analysis.

Comparable results were obtained after electroporation of total DNA from the stably transfected DS-2 cell line and from non-transfected DS-2 cells after digestion with the restriction endonuclease EcoRI. EcoRI cuts the plasmid pAM-HBsAg at two sites thereby producing two fragments of about 4.7 kbp and 3.5 kbp. Besides the coding region for the metallothionein (Mtn) promoter and the HBsAg-reporter construct the bigger fragment contains also the bacterial origin of replication and ampicillin resistance and thus all important components for the generation of ampicillin-resistant bacteria after re-ligation and transformation. In contrast, the smaller 3.5 kbp fragment contains no sequences which are necessary for the formation of ampicillin-resistant bacterial clones. After the re-ligation and electroporation of the DNA after digestion with EcoRI 295 bacterial colonies could be counted on ampicillin-containing LB-plates. By analysis of the purified plasmid DNA using EcoRI restriction digest it could be shown that 43 of 46 tested HBsAg-positive clones contained a 4.7 kbp DNA-fragment. After an EcoRI digest, 4 of the 46 extracted plasmids corresponded to the band pattern of the EcoRI restricted pAM-HBsAg plasmid. After the analytic restriction enzyme digest with EcoRI in the case of some plasmid preparations smaller DNA fragments could be detected in addition to the 4.7 kbp fragment. These fragments could be derived from chromosomal sequences which were cleaved out of chromosomal DNA during the EcoRI digestion and re-ligated with the 4.7 kbp fragment to a bigger plasmid. About 5% of the analysed HBsAg-positive bacterial clones contain exclusively 1 plasmid which includes the coding sequence of HBsAg but which differs in size from the 4.7 kbp fragment. These plasmids are probably again derived from the border region between chromosomal DNA and the plasmid DNA which recombined in multiple copies at an integration spot within the genome of the host cell. The generated ampicillin-resistant bacterial colonies which were generated after transfection of chromosomal DNA from non-transfected DS-2 cells proved HBsAg-negative in the PCR analysis with specific primers. These analyses show that the described method is excellently suited for the isolation and characterisation of any nucleic acids being present episomal or integrated into the genome of cells and therefore can also be used for the isolation and characterisation of nucleic acids from marker-positive cells.

The invention claimed is:

1. A method for the detection of a T-cell specific for a selected epitope comprising the following steps:
   a) isolating antigen presenting cell (APC)-containing and CD4+ T-cell-containing body fluids, said APC being selected from the group consisting of a dendritic cell, a monocyte, a macrophage and a B-cell,
   b) transducing the APC-containing body fluid with a gene transfer vector comprising (i) a first promoter which is specifically inducible in antigen presenting cells by epitope-specific contact with said CD4+ T-cell, (ii) a nucleic acid encoding a marker gene functionally linked to said first promoter, (iii) a second promoter which is constitutive in antigen presenting cells and (iv) a nucleic acid encoding the selected CD4+ T-cell epitope which is functionally linked to said second promoter, wherein said first inducible promoter is selected from the group consisting of a OX40L promoter, a 4.1BBL(V1) promoter, a 4.1BBL(V2) promoter, a 4.1BBL(V3) promoter and a 4.1BBL(V4) promoter,
   c) incubating the body fluid containing the transduced APC with the body fluid containing the CD4+ T-cell; and
   d) detecting marker-expressing APC,
   wherein the presence of a marker-expressing APC indicates the presence of said T-cell specific for said selected epitope.

2. A method for the detection of an epitope-specific CD4+ T-cell specific for a selected epitope comprising the following steps:
   a) isolating antigen presenting cell (APC)-containing and CD4+ T-cell-containing body fluids, said APC being selected from the group consisting of a dendritic cell, a monocyte, a macrophage and a B-cell,
   b) transducing the APC-containing body fluid with a promoter ($P_2$) which is constitutive in said APC, and a nucleic acid encoding the selected epitope which is functionally linked to said $P_2$ promoter,
   c) incubating the body fluid containing the transduced APC with the body fluid containing the CD4+ T-cell; and
   d) detecting marker-expressing APC, wherein the marker is encoded by a nucleic acid functionally linked to a controllable genomic promoter induced in said antigen presenting cells by epitope-specific contact with said CD4+ T-cell, said controllable genomic promoter being selected from the group consisting of a OX40L promoter, a 4.1BBL(V1) promoter, a 4.1BBL(V2) promoter, a 4.1BBL(V3) promoter and a 4.1BBL(V4) promoter,
   wherein the presence of a marker-expressing APC indicates the presence of said epitope-specific T-cell for said selected epitope.

3. The method according to claim 1, wherein said APC-containing body fluid in step b) is blood, a purified PBMC-population or a separated APC-population.

4. The method according to claim 1, wherein said step b) takes 0.5 to 168 hours.

5. The method according to claim 1, wherein said marker in step d) is a polypeptide which is naturally measurably induced or reduced in its expression after an epitope-specific recognition of an APC by a CD4+ T-cell.

6. The method according to claim 1, wherein said step b) takes 0.5 to 2, 2 to 6, 6 to 12, 12 to 36 or 36 to 168 hours.

7. The method according to claim 2, wherein said step b) takes 0.5 to 168 hours.

8. The method according to claim 7, wherein said step b) takes 0.5 to 2, 2 to 6, 6 to 12, 12 to 36 or 36 to 168 hours.

9. The method according to claim 2, wherein said APC-containing body fluid in step b) is blood, a purified PBMC-population or a separated APC-population.

10. The method according to claim 2, wherein said marker in step d) is a polypeptide which is naturally measurably induced or reduced in its expression after an epitope-specific recognition of an APC by a CD4+ T-cell.

* * * * *

UNITED STATES PATENT AND TRADEMARK OFFICE
CERTIFICATE OF CORRECTION

| | | |
|---|---|---|
| PATENT NO. | : 7,659,058 B2 | Page 1 of 1 |
| APPLICATION NO. | : 10/495843 | |
| DATED | : February 9, 2010 | |
| INVENTOR(S) | : Ludwig Deml | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 508 days.

Signed and Sealed this
Twenty-ninth Day of March, 2011

David J. Kappos
*Director of the United States Patent and Trademark Office*